(12) United States Patent
Call et al.

(10) Patent No.: US 6,887,710 B2
(45) Date of Patent: May 3, 2005

(54) ROBUST SYSTEM FOR SCREENING MAIL FOR BIOLOGICAL AGENTS

(75) Inventors: Charles J. Call, Albuquerque, NM (US); Eric Hanczyc, Renton, WA (US); Andrew Kamholz, Seattle, WA (US)

(73) Assignee: MesoSystems Technology, Inc., Albuquerque, NM (US)

(*) Notice: Subject to any disclaimer, the term of this patent is extended or adjusted under 35 U.S.C. 154(b) by 0 days.

(21) Appl. No.: 10/066,404

(22) Filed: Feb. 1, 2002

(65) Prior Publication Data

US 2002/0124664 A1 Sep. 12, 2002

Related U.S. Application Data

(63) Continuation-in-part of application No. 09/775,872, filed on Feb. 1, 2001, now Pat. No. 6,279,196, which is a continuation-in-part of application No. 09/265,619, filed on Mar. 10, 1999, now Pat. No. 6,267,016, and a continuation-in-part of application No. 09/265,620, filed on Mar. 10, 1999, now Pat. No. 6,363,800, application No. 10/066,404, which is a continuation-in-part of application No. 09/955,481, filed on Sep. 17, 2001, now Pat. No. 6,695,146, which is a continuation-in-part of application No. 09/494,962, filed on Jan. 31, 2000, now Pat. No. 6,290,065, and a continuation-in-part of application No. 09/191,980, filed on Nov. 13, 1998, now Pat. No. 6,062,392.

(60) Provisional application No. 60/337,674, filed on Nov. 13, 2001.

(51) Int. Cl.[7] .......................... G01M 3/02; G01N 33/00; G01N 1/14

(52) U.S. Cl. .......................... 436/53; 436/104; 436/106; 436/110; 436/174; 422/83; 422/88; 73/23.2

(58) Field of Search .................. 422/83, 88; 436/52, 436/53, 104, 106, 110, 139, 173, 174; 340/603; 73/23.2, 864, 864.33

(56) References Cited

U.S. PATENT DOCUMENTS

| | | | |
|---|---|---|---|
| 3,997,297 A | 12/1976 | Jenkins et al. | ............ 23/232 E |
| 4,111,049 A | 9/1978 | Lerner et al. | ......... 73/421.5 R |
| 4,580,440 A | 4/1986 | Reid et al. | ...................... 73/23 |
| 4,820,920 A | 4/1989 | Bather | ........................ 250/282 |
| 5,299,141 A | 3/1994 | Hungerford et al. | ........ 364/510 |
| 5,585,575 A | 12/1996 | Corrigan et al. | ......... 73/863.71 |
| 5,760,314 A | 6/1998 | Bromberg et al. | ....... 73/863.21 |
| 6,125,845 A * | 10/2000 | Halvorsen et al. | ..... 128/200.24 |
| 6,235,002 B1 * | 5/2001 | Carver et al. | ............... 604/183 |
| 6,324,927 B1 | 12/2001 | Ornath et al. | ............ 73/863.11 |
| 6,334,365 B1 | 1/2002 | Linker et al. | ............ 73/864.81 |
| 6,573,836 B1 * | 6/2003 | Gitis et al. | ................... 340/603 |
| 2004/0028561 A1 * | 2/2004 | Daugherty et al. | ........... 422/99 |

* cited by examiner

Primary Examiner—Lyle A. Alexander
(74) Attorney, Agent, or Firm—Ronald M. Anderson

(57) ABSTRACT

Items of mail are rapidly processed in a mail sampling system to determine if the mail is contaminated with a chemical or biological agent. The mail sampling system maintains a negative pressure in a containment chamber and includes a triggering sampler that makes a threshold determination regarding possible contamination, and a detecting sampler that obtains a sample for more detailed analysis in response to a signal from the triggering sampler. A sample of particulates collected from an item of mail is either removed for analysis or analyzed in the system to identify a contaminating agent. Optionally, the system includes an archiving sampler, which archives samples for subsequent processing and analysis, and a decontamination system, which is activated to decontaminate the mail if needed.

88 Claims, 37 Drawing Sheets

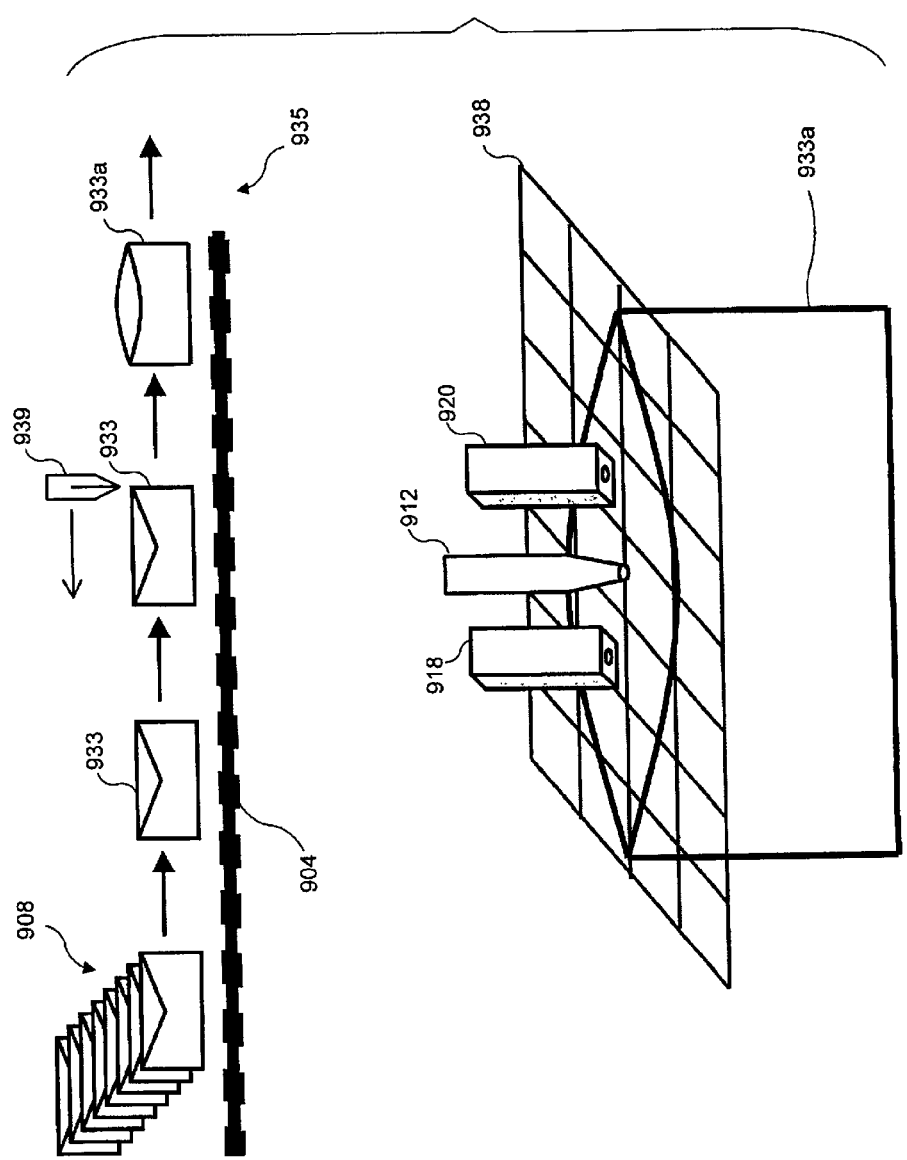

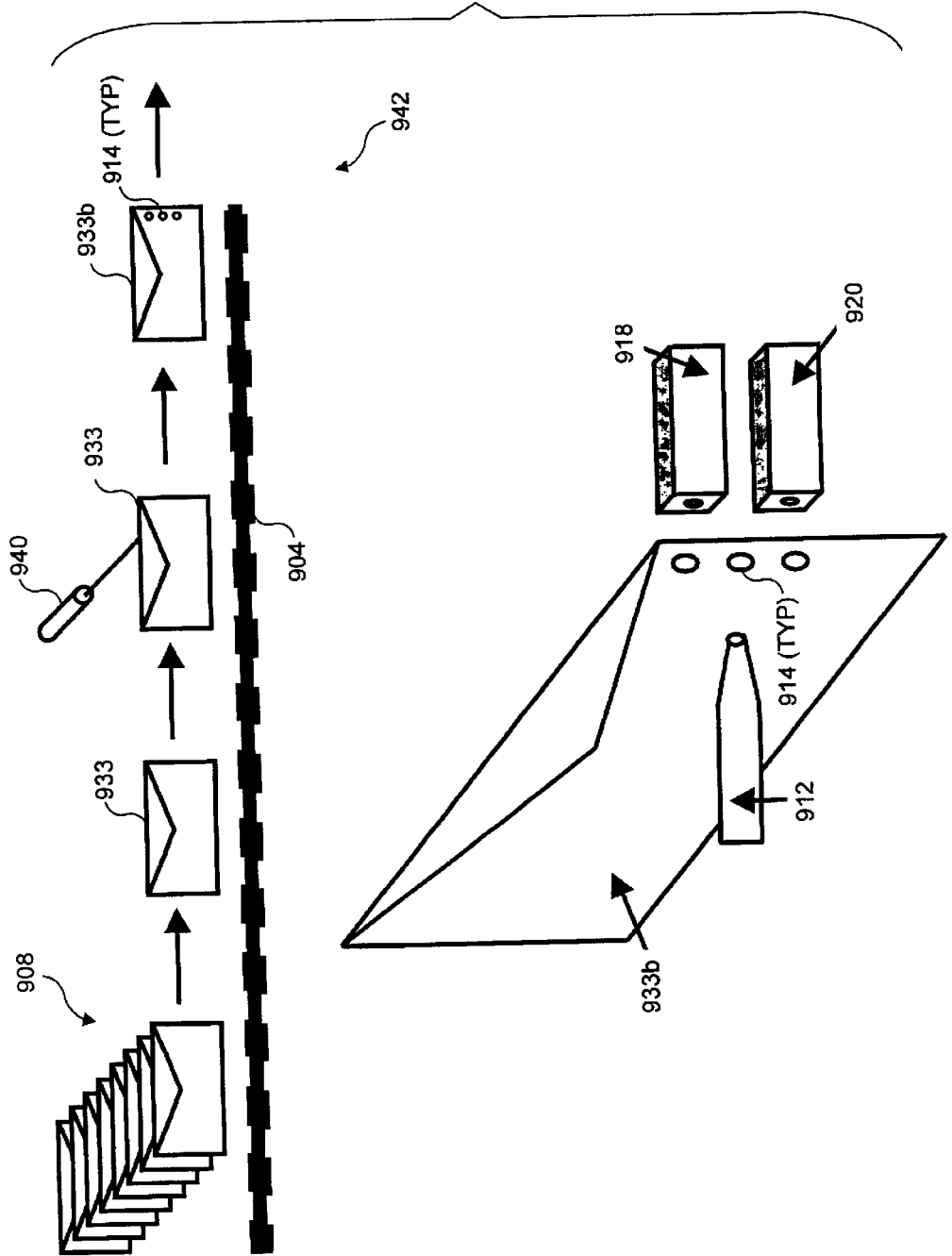

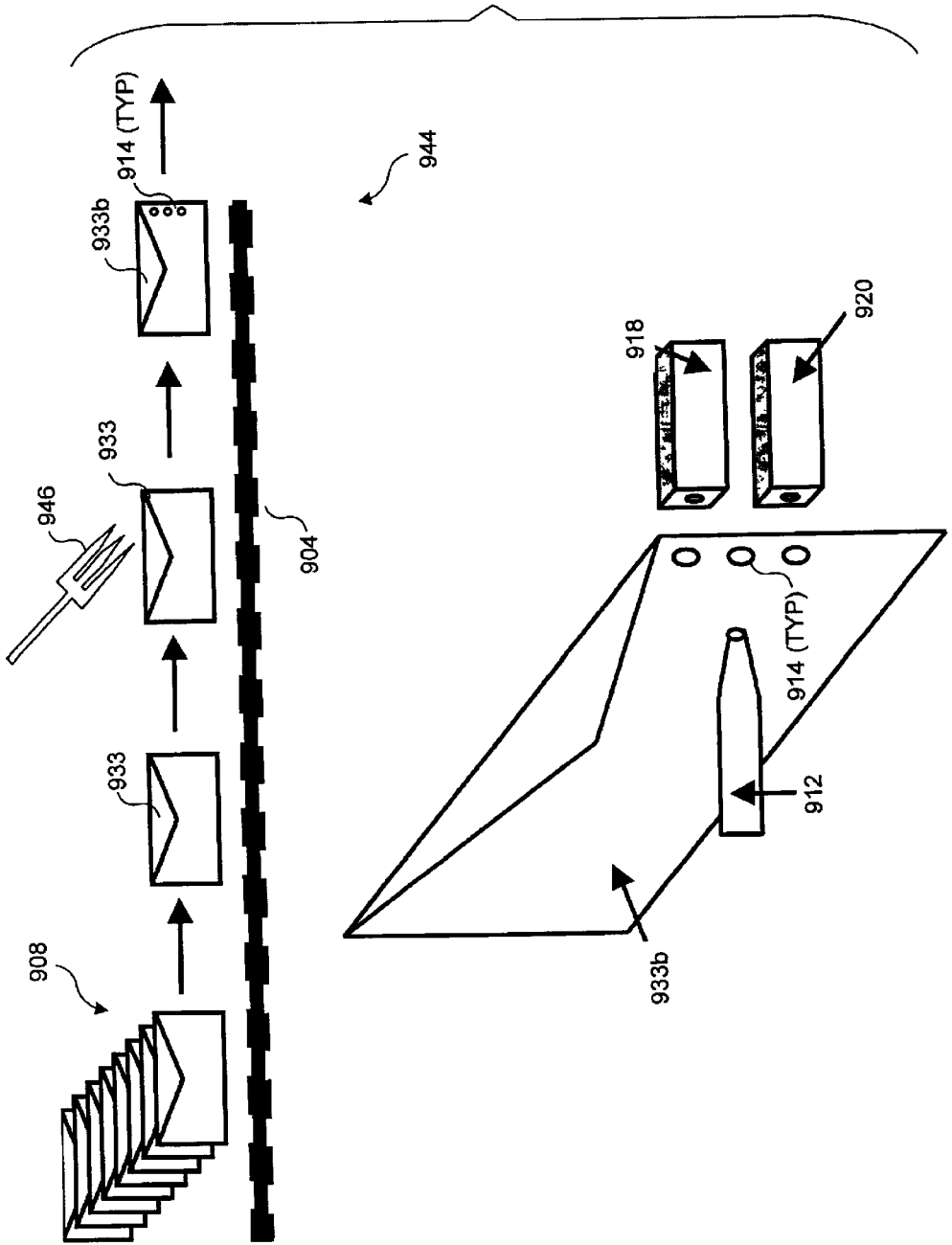

FIG. 3A

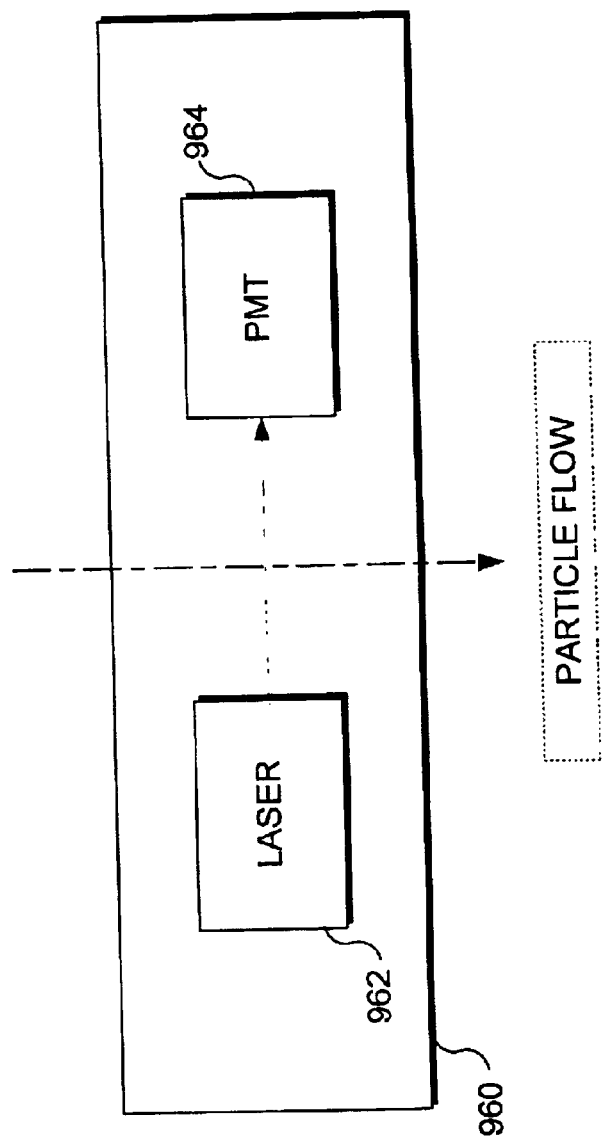

FIG. 4A

```
AEROSOLIZED CLOUD (916) → FAN/BLOWER (953) → VIRTUAL IMPACTOR (954)
                                                    ↓
                            MAJOR FLOW (958) → RINSE FLUID (959) → VENT TO HEPA FILTER (962) → HEPA FILTER (926)
                            MINOR FLOW (956) → RADIAL ARM COLLECTOR → WET SAMPLE COLLECTOR (966) → LAB (924) → ALARM (934)
                                                    ↑ (957)
                                              CONTROL (936)
```

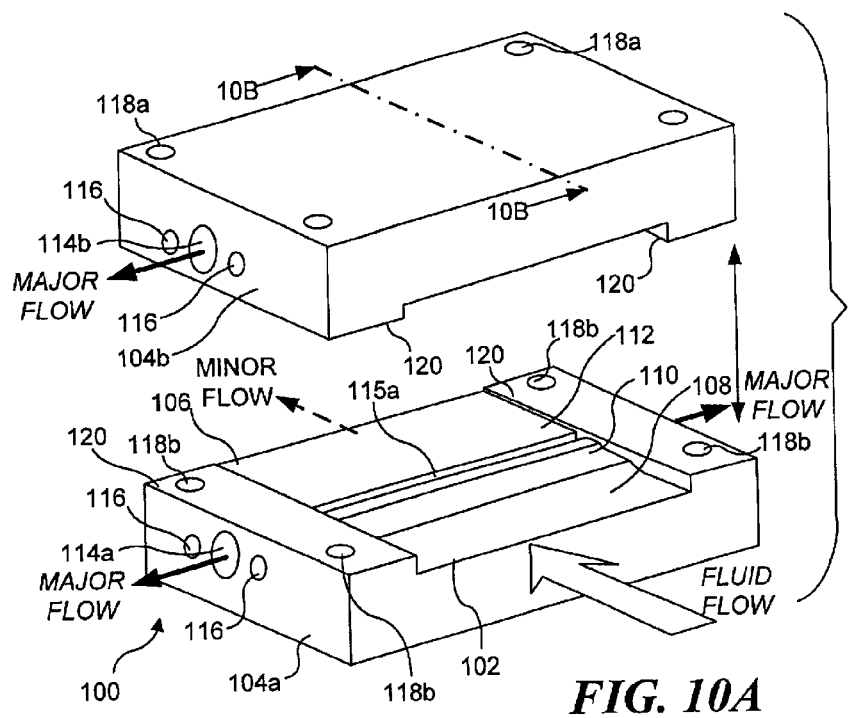
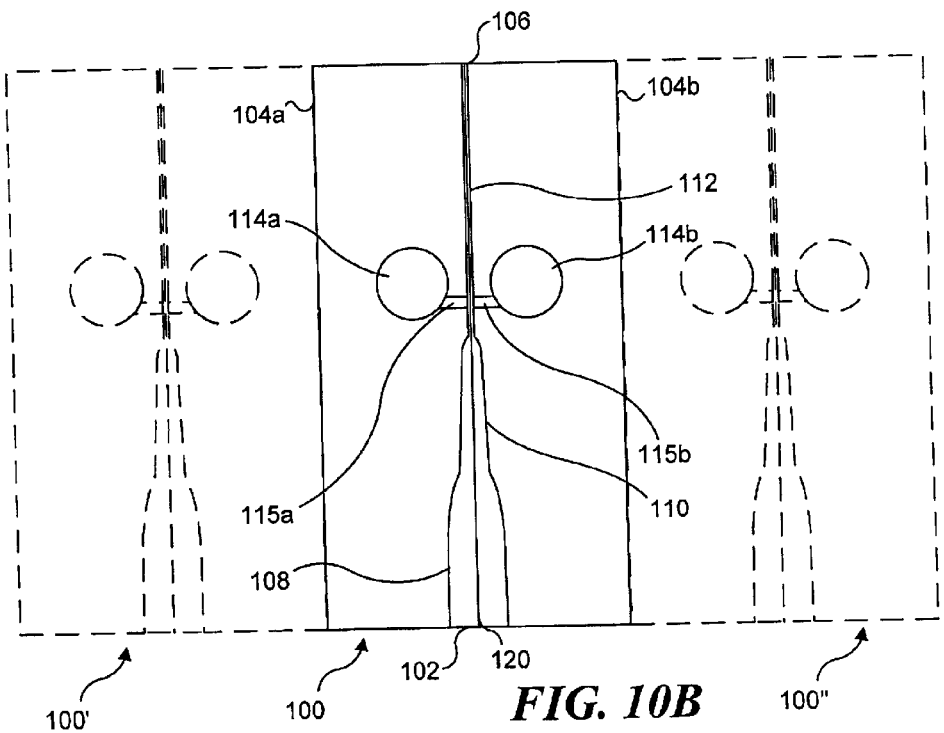

ROBUST SYSTEM FOR SCREENING MAIL FOR BIOLOGICAL AGENTS

RELATED APPLICATIONS

This application is based on prior copending U.S. Provisional Patent Application Ser. No. 60/337,674, filed on Nov. 13, 2001, the benefit of the filing date of which is hereby claimed under 35 U.S.C. § 119(e). The present application is a continuation-in-part of prior U.S. patent application Ser. No. 09/775,872, filed on Feb. 1, 2001, now U.S. Pat. No. 6,729,196, which itself is a continuation-in-part of U.S. Pat. No. 6,267,016, and of prior U.S. patent application Ser. No. 09/265,620, both filed on Mar. 10, 1999, now U.S. Pat. No. 6,363,800, the benefit of the filing dates of which are hereby claimed under 35 U.S.C. § 120. Further, the present application is a continuation-in-part of prior U.S. patent application Ser. No. 09/955,481, filed on Sep. 17, 2001, now U.S. Pat. No. 6,695,146, which itself is a continuation-in-part of Ser. No. 09/191,980, now U.S. Pat. No. 6,062,392 (filed on Nov. 13, 1998) and Ser. No. 09/494,962, now U.S. Pat. No. 6,290,065 (filed on Jan. 31, 2000), the benefit of the filing dates of which are hereby claimed under 35 U.S.C. § 120.

FIELD OF THE INVENTION

This invention generally relates to methods for aerosolizing and collecting particles from items of mail, and more specifically, to methods for collecting, identifying, and archiving such particles during high speed mail processing.

BACKGROUND OF THE INVENTION

Letters contaminated with weapons-grade *Bacillus anthracis* (anthrax) spores passed through the United States Postal Service (USPS) after Sep. 11, 2001. Over 16 cases of documented infections and several deaths have been directly attributed to such letters. By November 2001, over 32,000 individuals in the United States were taking antibiotics prescribed by physicians specifically as a prophylactic measure to combat a potential exposure to anthrax contaminated mail. Multiple mail processing facilities, and the equipment within those facilities, were contaminated by exposure to what appears to have been a statistically small number of intentionally contaminated letters.

It should be noted that the USPS relies heavily on automation to process over 550 million pieces of mail every day. Numerous advanced machines are thus employed for the handling of postal mail by both the USPS and businesses. One well-known manufacturer of such devices is Pitney Bowes (www.pitneybowes.com). Machines designed for processing mail have a range of envelope-handling capabilities, including stuffing, sealing, franking, and opening. The scope of such mail processing equipment ranges from desktop versions designed for use in a small office to very large industrial versions intended for use in a major corporate setting, or in a governmental postal facility. With respect to the anthrax contaminated letters mailed within the United States during September 2001, it appears that such mail processing equipment may have contributed to the cross-contamination spread of anthrax spores to mail received by many others than just the intended recipient of an intentionally anthrax-laced letter.

It appears that the very small size of the anthrax spores enabled at least some spores to escape from envelopes during mail processing, even while the envelopes remained sealed. Postal grade envelopes are not intended to be airtight, and processing such anthrax laced envelopes with mail handling equipment appears to have applied sufficient pressure to force spores out of such envelopes, so that the anthrax spores were released during mail processing, rather than only when the anthrax-laced mail was actually opened at its intended destination. The released anthrax spores then contaminated the mail processing equipment, and apparently cross-contaminated additional items of mail.

At the present time, there exists no mail processing equipment with the capability to screen mail for anthrax contamination, or other types of biological or chemical contaminants. Unfortunately, anthrax is not the only agent of concern. It has been suggested that the smallpox virus, which has been virtually eradicated in the natural environment, could be cultivated and used as an agent of terror in much the same fashion as the anthrax mailings were. Extremely toxic chemical agents such as ricin, might also be disseminated through the mail.

To address these issues, it has been suggested that all items of mail should be exposed to levels of radiation sufficient to kill such biological agents before the mail is otherwise processed and distributed, thus eliminating the danger posed by such biological agents.

While the techniques for mail irradiation are fundamentally similar to those used for the irradiation of certain agricultural products to reduce spoilage and kill pests, and can remove the danger presented by such biological agents, the equipment used for irradiation cannot detect the presence of such agents. From a security and law enforcement perspective, it is highly desirable to know of the occurrence of such events, even if irradiation has reduced or eliminated the threat. For example, early detection of intentionally contaminated mail will greatly aid law enforcement agencies in any investigation into the source of such contamination. While contaminated mail can be detected when it is opened at its ultimate destination, it is clearly much more preferable to detect and remove such mail from the postal system, even if irradiation has eliminated or reduced the risk of harm caused by the contamination.

It would therefore be desirable to provide a method and apparatus to identify mail within the postal system that is contaminated with anthrax spores, or other biological agents. While analytical devices and methods are available for detecting anthrax spores, such equipment and methods are not readily adapted for incorporation into high volume mail processing equipment.

Air monitoring equipment can be used in detecting contaminants. For example, a handheld, portable air monitoring system is described in commonly assigned U.S. patent application Ser. No. 09/775,872, filed on Feb. 1, 2001 and entitled BIOLOGICAL INDIVIDUAL SAMPLER. The application describes a device that can detect trace amounts of contamination within a volume of air that is sampled by the device. The device rapidly obtains a sample that can then be tested using analytical techniques appropriate to the suspected contaminant. For suspected anthrax contamination, the sample can either be taken to a lab for analysis, or can immediately be tested using commercially available (albeit somewhat less sensitive) "test strips." Such a system, however useful for air monitoring of a room or a disaster area, is not nearly as useful for detecting anthrax or other contaminant agents within mail. While a sample of air from or around a specific piece of mail could indeed be collected and tested with the device, the sheer volume of mail passing through the USPS makes widespread use of such equipment inadequate for testing the majority of the mail passing through the USPS to detect the presence of biological agents.

It would thus be desirable to provide a method and apparatus for detecting potentially harmful biological agents within the USPS that can achieve the following objectives:

1. The system should effectively process very high volumes of mail daily (i.e., from tens to hundreds of thousands of pieces of mail per day);

2. The system should be effective in detecting contaminated or suspect letters. Most important is the ability to detect anthrax, but the system should also be able to detect other biological and chemical agents;

3. The system must have an extremely low rate of false negatives (i.e., ideally, the system should not "miss" ANY contaminated letters);

4. The system should also have an extremely low rate of false positives (i.e., even one false positive in 500 million letters processed may be unacceptably high, given the disruption a positive indication of biological contamination is likely to generate);

5. The system should be relatively low in cost, resulting in a minimal increase in postal rates, preferably on the order of a penny per letter or less; and 6. The system for screening mail must be compatible with existing mail processing technology and operations and must protect personnel and facilities from contamination.

The prior art does not provide a system for simultaneously processing and analyzing high volumes of mail to detect biological threats that is capable of achieving even a few of the above objectives. Clearly, there is an immediate need for such a system to protect workers in the USPS and to protect all of the citizens of this country who depend upon and use the USPS.

SUMMARY OF THE INVENTION

One embodiment of the present invention is a method and a sampling system for automatically screening incoming mail to detect potential chemical and biological threats. It should be noted that while it is anticipated that the present invention will be very useful for sampling mail, that other types of packages, such as luggage, can also be sampled using the principles of the present invention. Thus the detailed description of the mail sampling embodiment described below should be considered to represents a preferred embodiment, and not the only embodiment. Those of ordinary skill in the art will appreciate that the elements of the present invention are also applicable to the screening of a plurality of different types of closed packages, such as but not limited to mail, luggage, shipping cartons, consumer goods, and the like.

The mail sampling embodiment includes a plurality of subsystems, including means for accessing a portion of the air within an parcel (so that the presence of potential chemical and biological threats in the air that is sampled can be detected), means for aerosolizing any particulates contained within the portion of air removed, a triggering sampler that determines if a threat may exist in the sample based upon the relative number of particulates contained in the sample or upon a quality of the particulates, and a detecting sampler that processes the sample to identify a threat. Optional additional subsystems include an archiving sampler that retains a solid sample of the particulates for archival purposes, one or more identification units for processing a sample to determine if the particulates are a specific chemical or biological agent, and a decontamination system for decontaminating an parcel identified as a potential threat.

Further preferred subsystems include a controller for automated control of the mail sampling system, an alarm to notify personnel of potential threats, virtual impactors for separating an air sample into a major flow with few particulates of greater than a predetermined size and a minor flow with significantly more particulates greater than the predetermined size, and rotating arm impact collectors for removing particulates from a fluid flow. Preferably, the system is equipped with high efficiency particle air (HEPA) filters and operates under negative pressure to reduce a risk of spreading any contaminants beyond the system.

Access to air within an parcel can be achieved by one of several different approaches. Although a piece of mail can be contaminated both on the outer faces and on the inside, intentionally contaminated mail will more likely contain contaminants inside an envelope or other enclosure. It is therefore necessary to gain access to the interior of a parcel. One way of accessing the interior of mail (specifically envelopes), employs a conventional mail splitting machine that is designed to handle large numbers of envelopes, sort them, convey them on a belt in single file, and split them open with a blade. Another means for accessing the interior of a parcel is perforating the parcel with one or more orifices using either a mechanical perforator or a laser beam. The orifices can range in diameter from about 100 microns up to about 1 cm, and can be located anywhere on the parcel. Additional means for accessing particulates contained in the interior of a parcel involves applying pressure to the parcel sufficient to expel particles out of the parcel.

Once access to the interior of a parcel is achieved, an air stream can be impinged onto the exposed portions of the parcel to aerosolize any particulate matter proximate to the exterior of the parcel. Similarly, an air stream impinging on the outer faces of the parcel can aerosolize any particulate matter disposed thereon. An air blower, properly synchronized with the means for accessing the interior of a parcel, represents a preferred aerosolizing means. Note that if pressure is employed as the mean for accessing, additional aerosolizing means may not be required.

The triggering sampler is disposed to receive the aerosolized particles. The air proximate the parcel is continually analyzed for particulate content. Preferably, the triggering sampler is capable of distinguishing between biological and non-biological particles based on laser induced autofluorescence of nicotinamide adenine dinucleotide (NAD) based compounds, which are present in almost all biological cells.

When a sudden increase in the number of particulates is observed, the detecting sampler is activated. Otherwise, all the sampled air is exhausted through the HEPA filter. Preferably, the increase in the quantity of particulates must exceed a predefined threshold value, for either biological, or both biological and non-biological particulates, before the detecting sampler is activated (to reduce false positives). Also preferably, if the detecting sampler is activated, the movement of items of mail through the mail sampling system is halted, so that the contaminated parcel does not leave the mail sampling system. If desired, an alarm can be actuated to notify an operator that a potential mail contamination threat has been detected.

The detecting sampler is designed to obtain a sample that can be analyzed to identify the nature of particulates detected by the triggering sampler. In at least one embodiment, the detecting sampler prepares a liquid sample for analysis in situ by an identification unit. In another embodiment, the detecting sampler prepares a liquid sample that must be removed from the mail sampling system for analysis elsewhere. In at least one embodiment, the detecting sampler includes a disposable collection unit that obtains a dry sample, which can then be rinsed to obtain a wet sample after the disposable collection unit is removed. In general, the detecting sampler is an impact collector, in which a flow of air including entrained particulates is directed toward an impaction surface, upon which at least some of the particles are retained for collection and subsequent analysis.

Several different technologies can be included to provide an integrated particulate identification unit in a mail sampling system, so that a liquid sample obtained by the detecting sampler can be analyzed in situ. While expensive devices such as a gas chromatograph coupled to an infrared spectrophotometer or a mass spectrophotometer could be incorporated into a system in accord with the present invention, it is clear that simpler and less costly systems will be preferable. It should be noted that while a gas chromatograph coupled to an infrared spectrophotometer or a mass spectrophotometer can generally be used to quickly identify many different compounds, simpler systems can generally only determine whether a particulate is a specific compound, or a member of a particular class of compounds. Thus, it might be desirable to include several different identification units in a mail sampling system, such as a unit adapted to detect anthrax, and another one or more units adapted to identify a different specific threat (such as smallpox, botulism, plague, ricin, explosives, narcotics, radioactives, etc.). One preferred technology employs a polymerase chain reaction and access to a related computer database for corresponding possible data results to quickly identify a variety of biological compounds. In another approach, a technician who has removed a liquid sample from the detecting system can test the sample with immunoassay strips that can detect the presence of anthrax or other contaminant substances.

An optional but very desirable subsystem is the archiving sampler. The purpose of the archiving sampler is to produce an archival solid sample of the particulate matter collected from the parcel. Such a sample is of great utility in a forensic analysis of contaminated mail. For example, upon discovering that a number of contaminated items of mail have passed through the USPS, it would be extremely useful to provide a permanent record comprising archived samples that can be consulted to determine the history of one or more contamination incidents. The archiving sampler preferably includes an impact collection surface that is coupled to a prime mover. Each time a new sample is collected, the prime mover ensures that a fresh portion of the impact collection surface is available for accepting a new sample. The movement of the impact collection surface is carefully tracked, so that the specific location of each sample collected is known, enabling any specific sample to be retrieved at a later time. Each sample represents a very small spot of deposited particulates, and a large number of such archival samples can be stored on a small archival surface.

Preferably, each sampler subsystem (triggering sampler, detecting sampler, and archiving sampler) uses a virtual impactor to concentrate the amount of particulates in a minor flow that is directed into the sampler subsystem. A virtual impactor performs the dual roles of drawing in air via a fan and concentrating the particulate matter via inertial flow splitting into the minor flow. Note that a virtual impactor is not strictly required, as less sophisticated embodiments could simply use a fan or other suitable means to draw air into the sampling subsystems. Thus, particulate concentration is a preferred, but nonessential aspect of the present invention. The increased concentration of particulates in a sample offers the advantages of providing the detector a sample with a higher concentration of potential threatening contaminants, thereby lowering the threshold for detection of such contaminants. Also, employing a high volumetric flow rate of air enables the mail sampling system to operate at a negative pressure, thereby ensuring that any particulates remain within the system and are not released to the outside ambient environment within a facility.

While many different types of virtual impactors are available, there are several preferred embodiments of virtual impactors usable in the present invention. In a first such embodiment, the virtual impactor includes a separation plate for separating particles from a fluid stream. The plate has a first surface and an opposing second surface, and the first surface includes plural pairs of a nozzle and a virtual impactor. Each nozzle has an inlet end and an outlet end. The virtual impactor includes a pair of fin-shaped projections tapering from the inlet end to the outlet end. Each projection has a convex outer wall and an inner wall. The inner walls of the pair of fin-shaped projections face each other and are spaced apart to define an upstream minor flow passage therebetween. The convex outer walls of the pair of fin-shaped projections cooperatively present a convex surface defining a virtual impact void, which in turn defines an inlet end of the upstream minor flow passage. The convex surface faces the outlet end of each nozzle, such that the nozzle and the upstream minor flow passage are generally aligned with each other.

In another embodiment, the virtual impactor includes a separation plate for separating particles from a fluid stream, and the separation plate has a first surface and an opposing second surface. The first surface includes plural pairs of a nozzle and a virtual impactor. The nozzle has an inlet end and an outlet end. Tapering from the inlet end to the outlet end, the virtual impactor is generally haystack-shaped, having a convex surface facing the outlet end of each nozzle. The convex surface defines a virtual impact void, which in turn, defines a terminal end of a minor flow passage that communicates between the first and second surfaces.

In yet another embodiment, the virtual impactor includes a separation plate employed for separating a fluid stream into a major flow and a minor flow, the major flow including a minor portion of particles that are above a predetermined size and the minor flow including a major portion of the particles that are above the predetermined size. The separation plate includes a block in which is defined a laterally extending passage having an inlet disposed on one edge of the block and an outlet disposed on an opposite edge of the block. The passage has a length extending between the inlet and the outlet and a lateral dimension extending along opposed surfaces of the passage in a direction that is orthogonal to the length and to a transverse dimension extending between the opposed surfaces. The lateral dimension is substantially greater than the transverse dimension of the passage, and the opposed surfaces of the passage between which the transverse dimension of the passage is defined generally converge toward each other within the block, so that the outlet has a substantially smaller cross-sectional area than the inlet. The virtual impactor also includes a transverse, laterally extending slot defined within the block, which is in fluid communication with a portion of the passage that has the substantially smaller cross-sectional area. A major flow outlet port is defined in the block and is in fluid communication with the transverse, laterally extending slot. The major flow enters the slot and exits the block through the major flow outlet port, while the minor flow exits the block through the outlet of the passage. The major flow carries the minor portion of the particles and the minor flow carries the major portion of the particles that are above the predetermined size.

Still another embodiment of a virtual impactor also includes a block. The block has a front and a rear, and a laterally extending passage is formed within the block and extends between an inlet at the front and an outlet at the rear of the block. The passage converges to a receiving nozzle located between the inlet and the outlet. The inlet has a substantially greater height than the outlet, but the height of the inlet into the passage is substantially less than a width of the passage. This virtual impactor also includes an elongate slot extending transverse to the passage and disposed distally of the receiving nozzle. A major flow orifice is formed within the block and intersects the slot. The major flow orifice provides a fluid path for the major flow to exit the block after changing direction. The minor flow continues on and exits the outlet of the passage, so that the major portion of the particles above the predetermined size are carried with the minor flow through the outlet of the passage, while the minor portion of the particles above the predetermined size are carried with the major flow through the major flow orifice.

A preferred impact collector for use in the detecting sampler is a rotating (or radial arm) impact collector. This impact collector can also be included in the triggering sampler, but its use therein is less beneficial. Because the rotating impact collector typically has a low flow rate (low flow rates are generally insufficient to test a very large volume of air in a short time period), it is therefore preferable to include, upstream to the rotating arm collector, a virtual impactor collector, such as described above.

A preferred radial arm collector includes a prime mover having a drive shaft that is drivingly rotated, an impeller that is mechanically coupled to the drive shaft and rotated thereby, and a housing for the impeller. The housing defines a fluid passage for conveying the gaseous fluid in which the particles are entrained to the impeller. The impeller includes vanes that draw the gaseous fluid into the housing so that the particles entrained in the gaseous fluid are separated from the gaseous fluid when impacted by the vanes of the impeller.

The optional decontamination subsystem is particularly useful if an in situ identification unit is provided to verify the existence of a chemical or biological agent. A decontamination fluid can be sprayed onto the contaminated parcel. An example of a suitable decontamination fluid is cetylpyridinium chloride, a highly effective anti-microbial that is so safe for humans it has been widely used in mouth rinses for over 40 years. Preferably, when the identification unit verifies the presence of a biological or chemical agent, the system control activates the decontamination subsystem and the decontamination fluid is applied as a spray to the contaminated parcel and the containment chamber (which may have been contaminated by aerosolized particles). Preferably, during decontamination (generally requiring only a few minutes of time) airflow into and out of the mail sampling system is halted, preventing any release of the contamination into the environment due to the escape of aerosolized chemical or biological agents. Note that timing is critical for decontamination to be effective. It is important that the contaminated parcel not exit the system before a positive identification of any contamination threat is achieved.

In at least one embodiment, a prefilter is used before each sampler in order to remove large paper fibers and other unwanted particles from the air. The prefilter could also be a virtual impactor. Preferably, a virtual impactor prefilter will separating particles entrained in a flow of fluid into a fluid flow containing particles over 30 microns in size (likely to represent large paper fibers) and a fluid flow containing particles less than 30 microns in size (likely potential contaminants and small paper fibers).

In yet another embodiment incorporates means to remove small paper fibers from the sampling systems. Preferably such means will remove such non-target fiber particles from impact collection surfaces, especially radial arm collectors. One embodiment of such means involves employing an enzyme such as cellulase in the rinse fluid. In embodiments in which a rinse fluid is continually flushed over the collection surface, the presence of cellulase in the rinse fluid will tend to catalyze paper fibers deposited on its surfaces, producing glucose, a soluble product of the enzymatic reaction, that is readily solubilized and rinsed away.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is a block diagram showing the components of a preferred embodiment of a system for detecting biological contaminants in mail;

FIG. 2A schematically illustrates a method for obtaining an air sample from a sealed enveloped by employing an envelope splitter;

FIG. 2B schematically illustrates a method for obtaining an air sample from a sealed enveloped with a laser beam;

FIG. 2C schematically illustrates a method for obtaining an air sample from a sealed enveloped with a mechanical perforator;

FIG. 2D schematically illustrates obtaining an air sample from a sealed enveloped by employing pressure to force the sample out of the envelope;

FIG. 3A is a block diagram showing the components of a preferred embodiment of a triggering sampler in accord with the present invention;

FIG. 3B is a block diagram showing the components of a preferred embodiment of a particle counter for use in the triggering sampler of FIG. 3A;

FIG. 4A is a block diagram showing the components of a first embodiment of a detecting sampler, in which the rotating arm collector is an integral (i.e., non-disposable) component of the detecting sampler;

FIG. 4B is a block diagram showing the components of a second embodiment of a detecting sampler, in which the rotating arm collector is a disposable component of the detecting sampler;

FIG. 5 is a block diagram showing the components of an archiving sampler in accord with the present invention;

FIG. 6A is a schematic view of a virtual impactor;

FIG. 6B is a plan view of a separation plate employed in the present invention;

FIG. 6C is a cross-sectional view of the separation plate taken along line 6C—6C of FIG. 6B;

FIG. 6D is an enlarged view of a nozzle and a virtual impactor from FIG. 6B;

FIG. 6E is an enlarged view of another configuration of a nozzle and a virtual impactor;

FIG. 7A is a schematic cross-sectional view of a virtual impact collector that includes another configuration of a separation plate in accord with the present invention;

FIG. 10A is an isometric view of yet another alternative embodiment of a separation plate in accord with the present invention;

FIG. 10B is a cross-sectional view of the separation plate of FIG. 10A, taken along section line 10B—10B, showing additional separation plates arrayed on each side in phantom view;

DESCRIPTION OF THE PREFERRED EMBODIMENT

Overview

Figure 1:
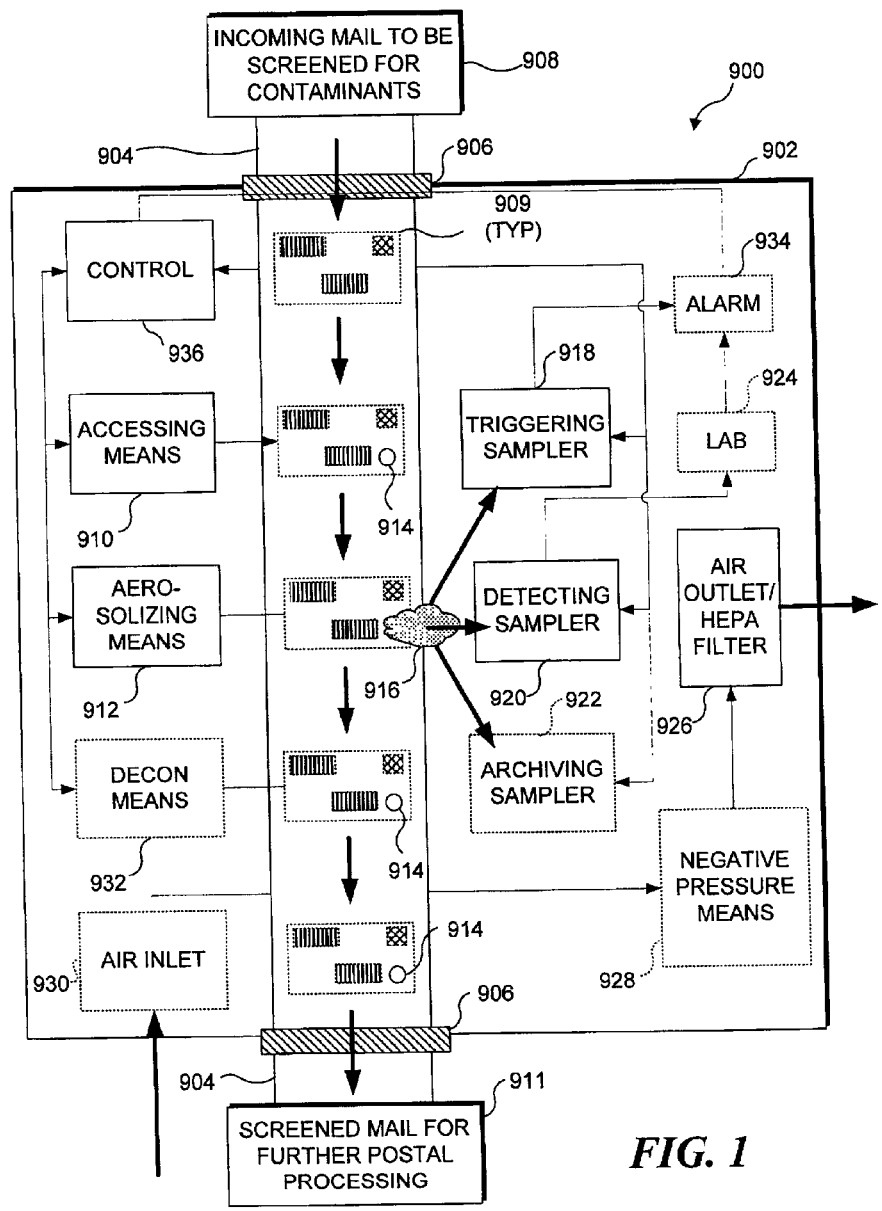

The present invention relates to a method and apparatus for rapidly analyzing containers to determine if such containers are contaminated with chemical or biological agents.

It should be noted that the preferred embodiments described below are particularly well adapted to screen items of mail for chemical or biological agents. Thus while a preferred embodiment of the invention, described in detail below, refers to screening items of mail, it should be understood that other items can also be screened for chemical or biological agents using the present invention. For examples, private delivery companies specializing in delivering packages more rapidly than the USPS could use the principles of the present invention to screen packages they accept for delivery. Similarly, freight companies that transport packaged goods over the road may also employ the concepts described herein to screen packages they accept for delivery. Clearly, the principles of the present invention can be applied to screening of non-mail items as well, and it should be understood that the present invention is not limited to only being useful for screening mail.

In the description and the claims that follow, the term "parcel" has been employed to describe an item that is screened for the presence of chemical or biological agents. It should be understood that the term parcel encompasses traditional items of mail, such as envelopes of various sizes and styles, postcards, magazines, and packages (such as boxes, padded envelopes), as well as other types of containers not generally shipped through the USPS, such as packages provided by or delivered by private delivery services, as well as other containers fashioned out of materials such as fiber products, plastics, composites, metal, and wood. It is anticipated that the present invention will be utilized to screen luggage.

With respect to the types of contaminants that the present invention can screen for, it should be understood that if a detection method exists for identifying a specific chemical or biological compound, then some embodiment of the present invention can be employed to screen a parcel to determine if that specific contaminant is associated with the parcel. As will be described in detail below, some embodiments of the present invention obtain a sample that is to be analyzed separately, and some embodiments incorporate means for performing analysis to determine if a specific contaminant is present. While it is anticipated that embodiments of the present invention will be useful in screening parcels to detect the presence of chemical agents such as toxins and explosives, and biological agents such as infectious and disease causing organisms, it should be clear that the present invention, used in conjunction with or incorporating suitable detection means, can be employed to screen for other types of chemical and biological agents as well. For example, systems in accord with the present invention can be furnished with detectors capable of detecting narcotics, so parcels can be non-invasively screened for narcotics. If it is determined that radioactive agents represent a threat, then detectors capable of detecting radioactivity, particularly alpha and low energy beta radiation, can be included in systems in accord with the present invention. While gamma radiation and high-energy beta radiation can likely be detected by using conventional detection equipment (i.e. Geiger counters) to scan the surface of a parcel, less energetic radiation (low energy beta, and particularly alpha radiation) can be effectively blocked by even thin layers of paper, and likely will not be detected by scanning the surface of a parcel. The present invention can be employed to obtain a sample associated with the interior of a parcel, and such a sample can then be tested for such low energy radioactive material.

The phrase "particles associated with a parcel" is employed to refer to particles (possibly chemical or biological agents) that are either contained within a parcel, or are deposited on an outer surface of a parcel. Particles that are contained within a parcel can be adhered to an interior surface of the parcel itself, adhered to an interior surface of an object that is itself contained within the parcel, freely dispersed within the parcel, entrained within a fluid (such as air) contained within the parcel, or any combination thereof.

In the following description, an overview of the entire system is first provided. Then, the individual components of the system and the processes implemented in the overall method are discussed in greater detail.

A preferred embodiment of the present invention includes: a containment chamber, preferably operating under a negative pressure, in which individual parcels are sampled; means for obtaining a quantity of air from within (and/or from the surface of) each parcel; a triggering sampler that makes a threshold determination as to whether a more detailed analysis of a parcel is required; and, a detecting sampler that obtains a sample for more detailed analysis. In one embodiment, the sample is removed and taken out of the system for analysis, preferably at the location of the system, but alternatively, at another site. In another embodiment, additional components are included to provide real time analytical capability within the system. Also optionally included is a decontamination system, which is triggered once a detection sample has been obtained. An archiving sampler can be beneficially optionally included in the mail analysis system of the present invention, to provide forensic samples that can be stored for additional testing at a later time. Such an archiving sampler will concentrate, collect, and deposit "spots" of particulates collected from a mail item and carried in a fluid onto a solid, archival quality medium. This archive, which can retain many spots collected at different known temporal intervals, will enable investigations (based on an analysis of the collected particulates) to be conducted when desired, at a future time.

Because certain materials can be dangerous even at low levels of concentration, the present invention preferably includes components that facilitate concentrating the particulates drawn from a mail item into a smaller volume of air, thus providing a more concentrated sample that facilitates easier and more reliable analysis. As will be described in detail below, virtual impactors can be used to provide such concentrated samples. Because the likely contaminants in parcels such as mail are expected to be in the form of particulates, particle impact collectors, with or without specialized coatings, are preferably employed to collect samples of the particulates from the air that is drawn from each parcel. Collected particles can include, but are not limited to, viruses, bacteria, bio-toxins, and pathogens. Those of ordinary skill in the art of detecting such contaminants will recognize that collected samples can be analyzed using a variety of known analytical techniques, including, but not limited to, mass spectrophotometry. In at least one embodiment, the present invention preferably includes a control unit, such as a computing device or hard wired logic device, that executes sample protocols to enable the system and process to be automated for efficiency.

Additional optional components, described in more detail below, include prefilters to remove particles larger than a suspected contaminant from air streams being directed to one of the sampling systems (triggering sampler, detecting sampler, or archiving sampler), and means for removing small fiber particles from the sampling systems, to prevent undesirable buildup of such particles on the collection surfaces.

In the following description of virtual impactors useful in the present invention, the prefix "micro" is generally applied to components that have submillimeter-size features. Micro-components are fabricated using micromachining techniques known in the art, such as micromilling, photolithography, deep ultraviolet (or x-ray) lithography, electro-deposition, electro-discharge machining (EDM), laser ablation, and reactive or nonreactive ion etching. It should be noted that micromachined virtual impactors provide for increased particulate collection efficiency and reduced pressure drops. Also as used herein, and in the claims that follow, the following terms shall have the definitions set forth below.

Particulate—any separately identifiable solid, semi-solid, liquid, aerosol, or other component entrained in a fluid stream that has a greater mass than the fluid forming the fluid stream and which is subject to separation from the fluid stream and collection for analysis. For the purposes of the present description, the mass density of particulates is assumed to be approximately 1 gm/cm$^3$. It is contemplated that the particulates may arise from sampling air and may include inorganic or organic chemicals, or living materials, e.g., bacteria, cells, or spores. Note that the term "particle" as used herein is interchangeable with the term particulate.

Fluid—any fluid susceptible to flow, including liquids and gases, which may entrain foreign particulates. Unless otherwise noted, the term "fluid" as used herein shall mean an ambient fluid, such as air, containing unconcentrated particulates that are subject to collection, and not the fluid into which the particulates are concentrated after collection or capture.

Spot—an aggregate of particulates deposited upon an archival surface in a relatively small area, so that individual particulates are aggregated together to form a larger spot, which can be readily observed under magnification or with the naked eye.

Mail Sampling System Components

A preferred embodiment of the present invention is shown in FIG. 1. Mail sampling system 900 is expected to be disposed in a room through which mail items received by the USPS are brought for initial processing. It is contemplated that mail sampling system 900 will be used in existing mail processing facilities. When possible, it is preferable for mail sampling system 900 to be positioned in a room separate from the rest of a post office facility, so that in the event a contaminated parcel is discovered, mail sampling system 900 is easily isolated from other mail processing activities. While mail sampling system 900 has features designed to prevent chemical or biological agents from a contaminated parcel being dispersed into the ambient environment surrounding the system, isolating mail sampling system 900 from other postal operations is prudent. Furthermore, in the event a contaminated parcel is detected, mail sampling system 900 might itself require decontamination, and the decontamination is facilitated if mail sampling system 900 is in an isolated location.

Preferably mail sampling system 900 is installed in a room that has an active air intake fan in operation, and in which all outgoing air is filtered before release into the outdoor ambient. Incoming mail to be analyzed for contamination is preferably stored inside the room until processed by the present invention. Mail sampling system 900 preferably includes a containment chamber 902, in which all mail sampling occurs. Mail to be screened for contaminants enters containment chamber 902 via a feeder 904 (generally a conveyor belt similar to those employed in conventional mail processing rooms and baggage handling systems in airports). Feeder 904 moves incoming mail 908 through a first seal 906 into containment chamber 902. The mail passes through the width of containment chamber 902 and out through a second seal 906. Screened mail 911 that has passed through the system is then available for further processing. Feeder 904, and other conventional equipment necessary to sort and manipulate mail to enable items of mail to be individually fed into containment chamber 902 are well known in the art; such equipment is hereinafter referred to as "the incoming mail handler."

Seals 906 substantially isolate containment chamber 902 from the rest of a post office or other mail processing facility. Note that seals 906 do not completely isolate containment chamber 902 from the environment, but do substantially reduce the amount of air exchange in and out of containment chamber 902. This reduction in air exchange can be achieved using a plurality of flexible elastomeric panels, e.g., fabricated from plastic strips, that substantially block the openings into containment chamber 902 except when deflected by items of mail. While a parcel is moving through one of seals 906, these flexible panels deflect sufficiently to allow the parcel to pass through the opening into or out of containment chamber 902, while simultaneously minimizing the amount of air exchanged between the ambient environment and the interior of containment chamber 902. Such flexible panels are often found in the freight loading bays of warehouses and in supermarkets, generally where a significant temperature difference exists between two locations thus separated, but where the movement of items between the two locations precludes the use of a solid door to isolate the locations from one another.

While a seal that is able to completely isolate the interior of containment chamber 902 from the ambient environment would enhance the ability of mail sampling system 900 to prevent any chemical or biological contamination in the interior of containment chamber 902 from being released, such airlocks would significantly reduce the movement of mail that passing into and out of containment chamber 902 in any period of time, making the system too inefficient. Because sampling system 900 must be capable of processing large volumes of mail rapidly, such airlocks would be unduly limiting. In any event, because containment chamber 902 includes HEPA filters to filter air released into the environment from inside the chamber, and because the interior of the containment chamber is maintained at a negative pressure (as will be described in more detail below), there is minimal risk of contamination escaping containment chamber 902 via seals 906, even if seals 906 do not block all movement of air into and out of the chamber. As long as the negative pressure environment exists within containment chamber 902, airflow past seals 906 will only be in one direction (into the containment chamber), and contaminants should not escape the containment chamber through seals 906.

The incoming mail handler separates the mail into individual envelopes or packages, which enter into containment chamber 902 in single file. If desired, a single containment chamber can include parallel processing lines, each line being provided a separate feeder to carry the mail through the system. As each parcel 909 enters containment chamber 902, it is exposed to means for accessing 910, and to aerosolizing means 912. In general, means for accessing 910 enables access to an interior of a parcel, so that particles inside a parcel can sampled, and aerosolizing means 912 ensures that any particulates removed from the parcel are substantially aerosolized, which aids in the sampling procedures discussed below. Note that when particles are adhered to the exterior surfaces of a parcel, aerosolizing means 912 itself provides access to the particles, and in that case could be considered as means for accessing the particles associated with a parcel. Means for accessing 910 can carry out one of several different approaches to access particles in a parcel, including using a laser to generate openings in a parcel, using a blade to split open an envelope, using a mechanical perforator to form openings in a parcel, and applying pressure to a parcel. Such means are discussed in more detail below. Most often (except when the means for accessing applies pressure), one or more openings 914 are formed in the parcel; i.e., in the envelope or wrapping of a parcel.

Aerosolizing means 912 preferably comprise a blower or other fluid moving device that directs a jet of fluid toward the parcel from which particles have been extracted by means for accessing 910. If a parcel includes any chemical or biological particulates within the parcel (or particles are adhered to an outer surface of the parcel), an aerosolized cloud 916 is formed as the jet of fluid contacts the particulates associated with the parcel.

The present invention employs at least two, and potentially three different sampling systems to analyze aerosolized cloud 916. A triggering sampler 918 operates continuously to determine if a concentration of particulates in the aerosolized cloud is above a threshold or to determine if the particulates have a predefined quality indicative of a potential threatening contamination. A detecting sampler 920 and an optional archiving sampler 922 operate intermittently, in response to the determination made by the triggering sampler.

The triggering sampler rapidly counts the number (i.e., density) of particulates in aerosolized cloud 916. If the count is sufficiently high, detecting sampler 920 is activated, and a sample of the particulates in aerosolized cloud 916 is obtained for analysis. As described in more detail below, detecting sampler 920 preferably obtains a liquid sample to facilitate the analysis of the collected particulates. In one embodiment of the present invention, the sample is retrieved for analysis outside of mail sampling system 900, while in another embodiment, the sample is directed to an identification unit 924 (labeled "LAB" in FIG. 1). Additional details of several useful identification units 924 are discussed below.

Optional archiving sampler 922 is likewise activated when the triggering sampler detects a sufficient number, or a rapid increase in the number of particulates in the aerosolized cloud relative to the aerosolized cloud sample obtained from other items of mail, or a number of particulates of a predefined quality (e.g., particulates comprising cells or spores). The archiving sampler 922 collects particulates from aerosolized cloud 916, and stores those particulates as a spot at a known location on an archival surface. At some later time, those archived particulates can be collected for analysis. Specific details of the archiving sampler are provided below.

Any airflow vented from these sampling systems (or from any other component in the interior of containment chamber 902) passes through a HEPA filter 926 to remove any traces of chemical or biological material from the airflow reaching the room ambient environment. Preferably, the room in which mail sampling system 900 is installed also has such a HEPA filter to filter air exhausted to the outside environment, to prevent the spread of contamination if any of the mail introduced into mail sampling system 900 is indeed contaminated. Preferably, negative pressure means 928 maintains the interior of containment chamber 902 at a lower than ambient pressure to ensure that air from containment chamber 902 does not flow into the ambient environment past seals 906. An optional restricted flow air inlet 930 can be included to allow additional air into containment chamber 902 as needed, although it is anticipated that sufficient air will enter into containment chamber 902 past seals 906, so that the inlet will not normally be needed. Negative pressure means 928 comprises an appropriately configured air blower, such as a centrifugal fan or a propeller blade fan (not specifically shown). Note that air exhausted by negative pressure means 928 into the ambient environment passes through HEPA filter 926.

The interior of containment chamber 902 will tend to accumulate particles. While such particles might be biological or chemical in nature, it is more likely that they will simply be other debris carried into the chamber with mail. Therefore, it may be necessary to occasionally pause the incoming mail handler so that air can cycle through the compartment. The HEPA filter will remove these particles on a continual basis. Occasional manual cleaning of the interior of the containment chamber may also be required.

If desired, a decontamination system 932 can be incorporated into mail sampling system 900. Decontamination system 932 can be configured to be activated in response to various different conditions. In one embodiment, decontamination system 932 is activated anytime triggering sampler 918 determines that the number of particles that have been counted exceeds a predetermined threshold at which the detecting sampler 920 should be activated. Another embodiment will provide for activating decontamination system 932 only if identification unit 924 positively identifies a collected particulate as being a chemical or biological agent of concern.

Preferably, mail sampling system 900 includes an alarm 934 (audible and/or visual), so that when triggering sampler 918 activates detecting sampler 920, the alarm alerts an operator that a potentially contaminated parcel has been detected, and mail sampling system 900 temporarily stops moving mail through the system. In embodiments that do not include identification unit 924, the operator retrieves the sample collected by detecting sampler 934, and the parcel from which the sample was collected. It is important that the movement of any individual parcel within containment chamber 902 be accurately tracked, so that potentially contaminated mail can be positively identified and removed. Once the contaminated mail is retrieved, mail sampling system 900 can then be reactivated. In embodiments that do include identification unit 924, alarm 934 is not activated, and mail sampling system 900 is not shut down unless a chemical or biological agent is actually detected in a sample.

Mail sampling system 900 also preferably includes a control 936. While each individual component could either include hardwired controls, or individual programmed control units, the use of a single control 936 for the entire system is preferred. In the following description, certain individual components, such as the rotating arm collector, are discussed as incorporating a separate control. It should be understood that such separate control is preferably eliminated when using control 936 to manage the functionality of all of the controllable components in mail sampling system 900.

Once passed through mail sampling system 900, screened mail 911 can be processed by conventional mail handler machines, such as conventional systems that automatically read address information from each piece of mail, and route the mail to the appropriate location. It is contemplated that mail sampling system 900 might also be integrated into other mail processing hardware.

In summary, this embodiment of the present invention conveys mail to be analyzed for chemical and biological agents into a negative pressure containment chamber, which includes a HEPA filtration system, a mechanism for opening letters or other items of mail, and pressurized air jets for aerosolizing any particulates that might be on the surface or contained within the items of mail. A triggering sampler continuously monitors the level of particulates (or quality of particulates) within the sampled air stream, and when required, a detection sampling system takes a wet sample of the particulates for detailed analysis. If desired, an archiving sampler is provided to collect and archive dry samples for later analysis, such as to facilitate a forensic investigation.

Optionally, a decontamination fluid is sprayed inside the containment chamber by decontamination means to decontaminate the interior of the chamber, if potentially threatening contamination is detected in a parcel being processed.

Integration of the optional identification unit, archiving sampler, and decontamination means are optional, but highly desirable. Without them, a mailroom must be immediately shut down and evacuated until the wet sample from the detection sampler can be removed by trained hazardous materials personnel, and results determined by an approved laboratory. This step might typically take several days. Risk to personnel in the room where the mail sampling system is installed is likely to be higher without automatic decontamination of the system.

The key components of the mail sampling system of the present invention are described in separate sections below. While not specifically discussed above, it should be noted that each of the samplers preferably include a concentrator that takes an air sample and separates that sample of air into two streams, a first stream having a relatively high concentration of particulates and a second stream having a relatively low concentration of particulates above a predetermined threshold size. This concentration is preferably achieved using virtual impactor technology, which is described in detail below.

By selecting suitable components, mail sampling system 900 can be optimized for detection of a specific perceived threat. For example, the system can be optimized to detect a specific biological agent, such as anthrax. As will be described below, a specific triggering sampler designed to count only biological particles can be coupled with an integrated identification unit designed to determine if a collected biological particulate is anthrax. Other mail sampling systems could employ a triggering sampler that counts all particulates (not just biological particles), and a detecting sampler that provides a wet sample for removal and analysis offsite to check for a number of different potential contaminants. The latter type of mail sampling system could be used to detect items of mail that have been contaminated with any of a relative wide variety of different chemical and biological agents, not just anthrax.

Mail Handling and Feeder

The incoming mail handling equipment associated with incoming mail 908, feeder 904, and outgoing mail handling equipment associated with screened mail 911 are generally conventional and well known in the art. Mail handling system 900 is preferably adapted to easily integrate into an existing mail processing facility. There are many existing systems for separating mail into individual pieces and orienting the items on a conveyer belt. Preferably, feeder 904 is a conventional component selected to meet the dimensions of containment chamber 902. Note that if non mail items are to be screened, that feeder systems specifically adapted for use with the types of parcel to be screened can be employed.

Means for Accessing

To access particles from within a parcel, any of several different means can be employed. For example, existing mail splitting machines are designed to handle large numbers of envelopes, sort them, convey them on a belt in single file, and split them open with a blade. Other techniques that are suitable for carrying out this function include perforating the parcel with one or a plurality of holes, ranging in size from about 100 microns up to 1 cm and preferably located adjacent to an edge of the parcel. It is possible to perforate the parcel by burning holes with a laser or by using a mechanical perforator. It is further contemplated that air from within a parcel can be accessed simply by compressing the parcel, either using mail processing equipment or with a mechanism having two opposed surfaces (not shown) that are moved toward opposite sides of a parcel to expel particles contained within the parcel.

FIG. 2A illustrates an envelope splitter system 935. This system can be employed with parcels that are envelopes. Incoming mail 908 is separated into individual envelopes 933 using conventional mail handling equipment (not separately shown). As described above in conjunction with FIG. 1, feeder 904 is employed to bring each parcel into the containment chamber, where the means for accessing is utilized to sample air from within each parcel. As shown in FIG. 2A, means for accessing 910 can comprise envelope splitter system 935, which employs an envelope splitter 939 to open each envelope. Each open envelope 933a is then directed to aerosolizing means 912 (preferably an air blower), which directs a jet of air toward the opened envelope. Note that as shown in the enlarged, lower portion of FIG. 2A, triggering sampler 918 and detecting sampler 920 are disposed immediately adjacent to aerosolizing means 912, so that any particulates aerosolized from the open envelope will be collected by the detectors.

Also shown in FIG. 2A is a grill 938, such as a nylon or wire mesh screen, that is employed to prevent non-particulate contents of an opened envelope (i.e., a folded letter) from being drawn from the envelope. Grill 938 can be fabricated from any material similar to nylon or wire mesh that can provide structural stability sufficient to withstand the force of the aerosolizing means. System 935 is most suited to handling mail for large organizations, such as corporations or governmental agencies, at a point close to the final destination of the mail. Clearly, an envelope that has been slit open is not suitable to be reintroduced into the postal system. Such envelopes can be readily directed to appropriate offices at a location. It should also be understood that system 935 is generally limited to use with envelopes, rather than other items of mail, such as packages, magazines and postcards.

A different accessing system is shown in FIG. 2B, which illustrates a laser based accessing system 942. Incoming mail 908 is separated into individual parcels, such as envelopes 933, using conventional mail handling equipment (not separately shown). Once again, feeder 904 is employed to bring each parcel into the containment chamber, where a laser 940 is employed to form at least one opening 914 in each envelope. Each open envelope 933b with opening(s) 914 is then directed to aerosolizing means 912, which directs a jet of air toward openings 914. Once again, triggering sampler 918 and detecting sampler 920 are disposed immediately adjacent to aerosolizing means 912 (see the enlarged portion of FIG. 2B), so that any particulates coming from the openings in the envelope are aerosolized so that they can be collected by the samplers. As shown in FIG. 2B, aerosolizing means 912 is disposed adjacent one side of open envelope 933b, as compared to triggering sampler 918 and detecting sampler 920. Because openings 914 pass entirely through open envelope 933b, the jet of air from aerosolizing means 912 is also able to pass completely through the envelope to reach the samplers disposed on the opposite side.

Because openings 914 are so small (from about 100 microns up to about 1 cm) and may be located anywhere on the envelope, it is anticipated that system 914 can be employed to process mail that will be reintroduced into the postal system for delivery to its intended destination. It is further anticipated that openings could be formed by laser 940 in packages and magazines, as well as envelopes, however such openings may not pass completely through a package or magazine. In such cases, aerosolizing means 912, triggering sampler 918 and detecting sampler 920 are preferably disposed on the same side as the parcel being analyzed.

A very similar accessing system that employs a mechanical perforator rather than a laser is shown in FIG. 2C, which illustrates accessing system 944. Once again, feeder 904 is employed to bring each parcel into the containment chamber, where the means for accessing is utilized to obtain access to air from within each parcel. In system 944, a mechanical perforator 946 is employed to form at least one opening 914 in each parcel. Aerosolizing means 912 is disposed adjacent a side of the parcel opposite to the side at which triggering sampler 918 and detecting sampler 920 are disposed. Also as noted above, if system 944 is used to form perforations in packages and magazines, such perforations will not likely pass completely through a package or magazine, and in such cases, aerosolizing means 912, triggering sampler 918 and detecting sampler 920 are preferably disposed on the same side as the parcel being analyzed.

Figure 2D:
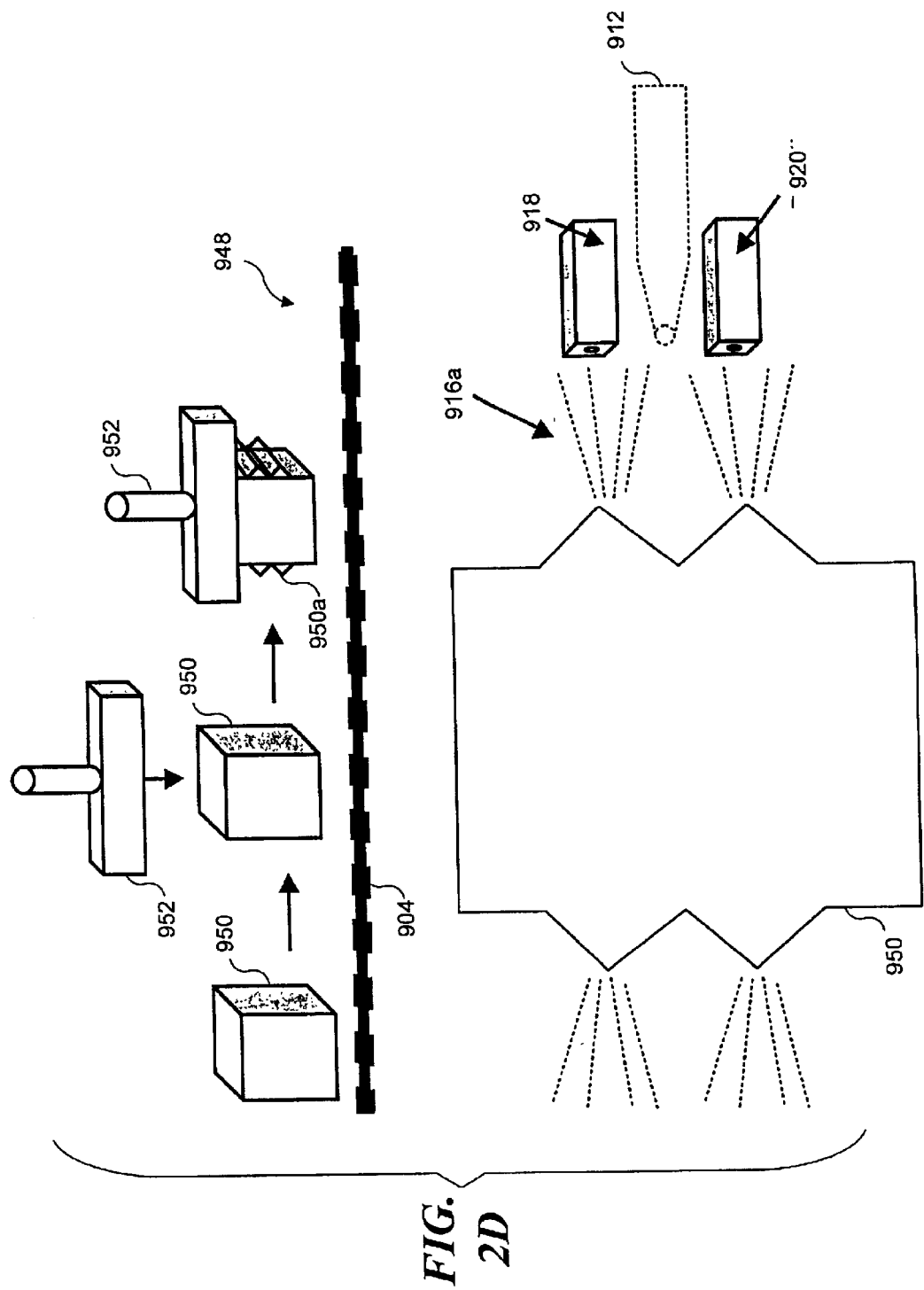

FIG. 2D illustrates an accessing system 948 that compresses a parcel 950 to force particulates within the parcel to be expelled. Because system 948 likely will also force air, as well as particulates out of parcel 950, that air itself should aerosolize any particulates from within the parcel, and aerosolizing means 912 may not be required. As described above, feeder 904 is employed to bring each parcel into the containment chamber, where the means for accessing is utilized to obtain air and any particulates from within each parcel. In FIG. 2D, means for accessing 910 is provided by a mechanical press 952 that rapidly applies pressure to the parcel, thereby forcing air out of the parcel.

As can be seen in the enlarged portion of FIG. 2D, triggering sampler 918 and detecting sampler 920 are disposed immediately to one side of, and immediately adjacent to the parcel (i.e., parcel 950) that has just been compressed by mechanical press 952, so that air 916a forced out of the parcel is directed toward the samplers. If desired, aerosolizing means 912 can also be included, though air 916 is already likely to contain aerosolized particulates. Note that as shown in FIG. 2D, air 916a is forced out of two sides of a parcel. It should be understood that air actually would be forced out of each side of a parcel not in contact with feeder 904 or mechanical press 952. Thus, triggering sampler 918 and detecting sampler 920 do not need to be disposed adjacent to each other, but instead must just be disposed adjacent to the parcel being pressed.

If an archiving sampler is incorporated into mail sampling system 900, then the archiving sampler should be disposed to access the air and any particulates accessed from the parcel in the same manner as triggering sampler 918 and detecting sampler 920. That is, the archiving sampler should be disposed so that air forced from a parcel (or the resulting aerosolized cloud 916), by any of the means described above is also directed toward the archiving sampler.

Aerosolizing Means

As discussed above, aerosolizing means 912 preferably comprises a blower or fan that directs a jet of air toward the parcel from which particulates have been extracted by means for accessing 910. If the ambient air used to produce the jet contains a high level of particulates, the ambient air should be filtered upstream of the jet of air. Such particulates might introduce background particulates that can be read by the particulate counter of triggering sampler 918. If desired, a source of prefiltered air or a filtered substantially inert gas (such as nitrogen) can be provided to produce the aerosolized cloud, such as from a compressed gas cylinder.

Virtual Impactor Technology

Because particulates of interest are often present in quite small concentrations in a volume of fluid, it is highly desirable to concentrate the mass of particulates (released from a parcel) into a smaller volume of fluid. As will be discussed in greater detail below with respect to the specific preferred embodiments of a triggering sampler, detecting sampler, and archiving sampler, an adequate concentration of any sampled particulate is expected to be very important in achieving rapid and accurate mail sampling. In one embodiment of the present invention, each sampler includes its own virtual impactor. In an alternate embodiment, a single virtual impactor feeds portions of a sample to all of the sampling systems. The following section provides details on virtual impactors in general, as well as describing several specific embodiments of virtual impactors that can be beneficially used in the mail sampling system of the present invention.

Virtual impactors can achieve a desired concentration of particulates without actually removing the particulates of interest from the flow of fluid. As a result, the particulate-laden fluid flow can be passed through a series of serially connected virtual impactors, so that the fluid flow exiting the final virtual impactor has a concentration of particulates that is two to three orders of magnitude greater than in the original fluid flow input to the first virtual impactor. The concentrated particulates can then be more readily counted by a particle counter, deposited on a collection surface, or analyzed.

Figure 6A:
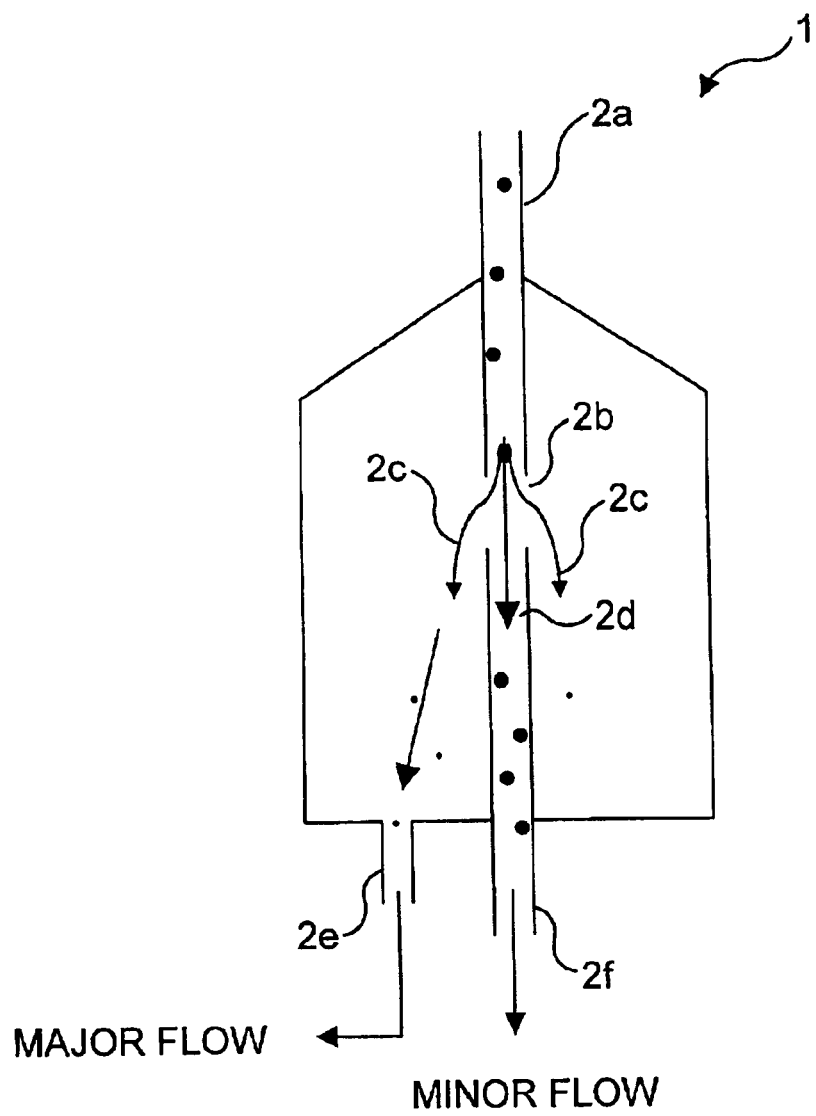

A virtual impactor uses a particle's inertia to separate it from a fluid stream that is turned, and a basic virtual impactor can be fabricated from a pair of opposing nozzles. Within a virtual impactor, the intake fluid coming through the inlet flows out from a nozzle directly at a second opposed nozzle into which only a "minor flow" is allowed to enter. This concept is schematically illustrated by a virtual impactor 1 shown in FIG. 6A. Fluid carrying entrained particulates flows through a first nozzle 2a. The flow from nozzle 2a then passes through a void 2b that separates nozzle 2a from a nozzle 2f. It is in void 2b that the flow of fluid is divided into a major flow 2c, which contains most of the fluid (e.g., 90%) and particles smaller than a cut (predetermined) size, and a minor flow 2d. Minor flow 2d contains a small amount of fluid (e.g., 10%) in which particulates larger than the cut size are entrained. Note that major flow 2c exits via opening 2e, and minor flow 2d exits via opening 2f.

As a result of inertia, most of the particulates that are greater than the selected cut size are conveyed in this minor flow and exit the virtual impactor. Most of the particulates smaller than the virtual impactor cut size are exhausted with the majority of the inlet air as the major flow. The stopping distance of a particle is an important parameter in impactor design. The cut point (size at which about 50% of the particles impact a surface, i.e., flow into the second nozzle) is related to the stopping distance. A 3 micron particle has nine times the stopping distance of a 1 micron particle of similar density.

For the present invention, several types of virtual impactors and their variants are suitable for use in collecting samples as spots for archiving purposes. Because any particular design of the minor flow nozzle can be optimized for a particular size of particle, it is contemplated that at least some embodiments of the present invention may include multiple nozzles, each with a different geometry, so that multiple particle types can be efficiently collected.

In at least one embodiment, when a virtual impactor is incorporated into one of the triggering sampler, the detecting sampler, and the archiving sampler, two virtual impactors are aligned in series, such that a concentration of particulates entrained in the minor flow of fluid exiting the second virtual impactor is approximately 100 times the original concentration. It should be noted that each time a virtual impactor is employed, a fan or blower is required to drive the fluid through the virtual impactor. Preferably, each sampler subsystem (i.e. the triggering sampler, the detecting sampler, and the archiving sampler virtual impactor) utilizes a virtual impactor dedicated to that sampler subsystem. However, it is contemplated that two or more sampler subsystems could share a virtual impactor (and the associated fan/blower), by splitting the concentrated particulates that are output from the virtual impactor.

Figure 6B:
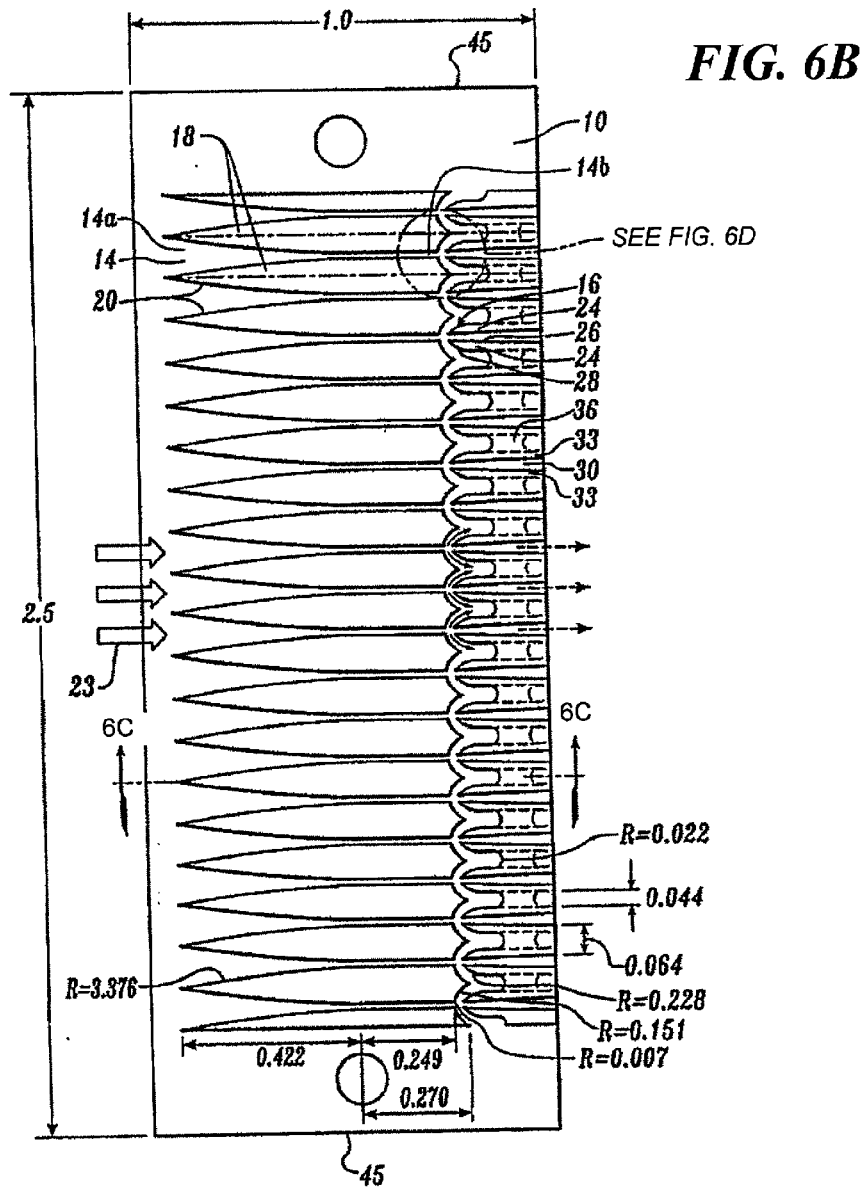
Figure 6C:
Figure 6D:
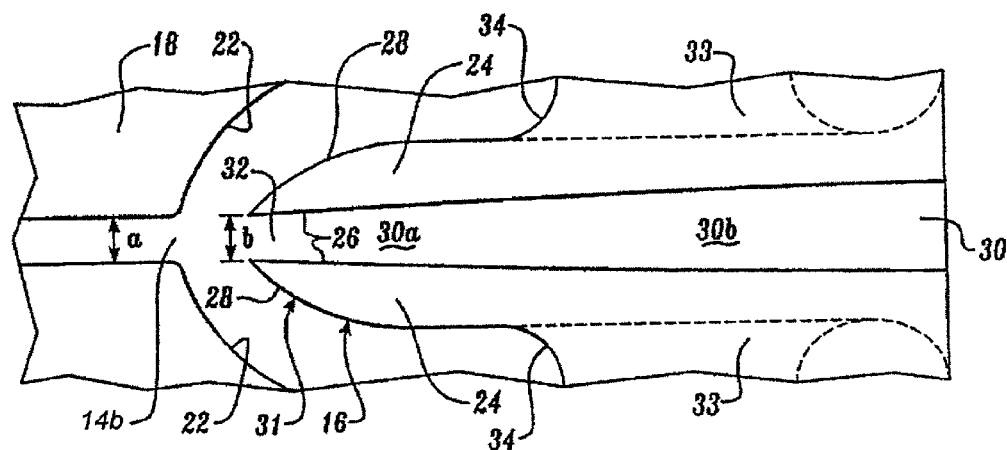

FIGS. 6B, 6C, and 6D illustrate an embodiment of a virtual impact separation plate 10 formed in accordance with the present invention. Separation plate 10 may be formed of various materials suitable for micromachining, such as plastics and metals. The separation plate includes a first surface 10a and an opposing second surface 10b. First surface 10a includes plural pairs of a nozzle 14 and a virtual impactor 16 (see FIG. 6D). Each nozzle 14 includes an inlet end 14a and an outlet end 14b and is defined between adjacent nozzle projections 18 having a height "H" (see FIG. 6C). Two nozzle projections 18 cooperate to define one nozzle 14. Each nozzle projection 18 includes two side walls 20 that are configured to define one side of a nozzle 14, which comprise a telescoping design that generally tapers from inlet end 14a to outlet end 14b. Nozzle projection 18 further includes two generally concave walls 22 at its downstream end that are positioned to provide nozzle projection 18 with a tapered downstream "tail." In contrast to a tapered downstream tail, another of the embodiments described below that is actually more preferred includes stepped transitions that reduce the size of the passage at its outlet. Throughout this description, the terms "upstream" and "downstream" are used to refer to the direction of a fluid stream 23 flowing through the separation plate.

Each virtual impactor 16 comprises a pair of generally fin-shaped projections 24 having height "H." Each fin-shaped projection 24 includes an inner wall 26 and a generally convex outer wall 28. Inner walls 26 of fin-shaped projections 24 (for a pair) are spaced apart and face each other to define an upstream minor flow passage 30a therebetween. Convex outer walls 28 of the pair of fin-shaped projections 24 cooperatively present a generally convex surface 31 facing the fluid flow direction. Referring specifically to FIG. 6D, an inlet end 32 of upstream minor flow passage 30a defines a virtual impact void through convex surface 31, where "virtual" impaction occurs as more fully described below. A width of outlet end 14b of nozzle 14 is defined as "a," and a width of inlet end 32 of upstream minor flow passage 30a is defined as "b."

First surface 10a of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30b therebetween. Upstream and downstream minor flow passages 30a and 30b are aligned and communicate with each other to form minor flow passage 30. As illustrated in FIGS. 6B, 6C, and 6D, fin-shaped projections 24 of adjacent virtual impactors 16 and virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downwardly and downstream through separation plate 10 to second surfaces 10b. As more fully described below, orifices 34 and passageways 36 are provided merely as one example of a major flow outlet and, thus, may be replaced with any other suitable major flow outlet.

In operation, particulate-laden fluid stream 23 is caused to enter inlet ends 14a of nozzles 14. Nozzles 14 aerodynamically focus and accelerate particulates entrained in fluid stream 23. In this telescoping design, the aerodynamically focused fluid stream 23 exiting outlet end 14b of nozzle 14 advances to convex surface 31 of virtual impactor 16. A major portion (at least 50%, and preferably at least about 90%) of fluid stream 23 containing a minor portion (less than about 50%) of particulates above a certain particulate diameter size, or cut size, hereinafter referred to as a "major flow," changes direction to avoid the obstruction presented by convex surface 31. Concave walls 22 of nozzle projections 18 and convex outer walls 28 of fin-shaped projections 24 cooperate to direct the major flow toward the upstream end of virtual impactor bodies 33. Bodies 33 prevent the major flow from continuing in its current direction. Orifices 34 are provided through bodies 33, so that the major flow enters orifices 34 and travels through passageways 36 to second surface 10b of separation plate 10, where it exits. A minor portion (less than 50%, and preferably less than about 10%) of fluid stream 23 containing a major portion (at least about 50%) of particulates above the cut size, exits as the minor flow and is collected near a "dead" zone, i.e., a zone of nearly stagnant air, created adjacent to the convex surfaces 31 of virtual impactors 16. The major portion of the particulates entrained in the minor flow "virtually" impacts the virtual impact voids at inlet ends 32 of upstream minor flow passages 30a and enters minor flow passages 30. The minor flow travels through and exits minor flow passages 30, enabling the particulates entrained therein to be collected for analysis and/or further processing.

Nozzles 14 contribute very little to particulate loss because they have a long telescoping profile, which prevents particulate deposition thereon. The long telescoping profile of the nozzles 14 also serves to align and accelerate particulates. Focusing the particulates before they enter the minor flow passage using the telescoping design may enhance the performance of the virtual impactor, since the particulates in the center of the nozzle are likely to remain entrained in the minor flow. Thus, as used herein, the term "aerodynamic focusing" refers to a geometry of a particulate separator that concentrates particulates toward the center of a central channel through the particulate separator. Because nozzles 14 aerodynamically focus and accelerate particulates in a fluid stream, virtual impactors 16 placed downstream of nozzles 14 are able to separate particulates very efficiently. By improving the particulate separation efficiency of each of virtual impactors 16, the present invention enables only one layer or row of virtual impactors 16 to carry out the particulate separation, which eliminates the chances of particulates being lost due to impact on surfaces of additional layers or rows of virtual impactors. Further reduction of particulate loss on inner surfaces of minor flow passages is achieved by enabling minor flows to advance straight through the minor flow passages upon virtual impaction, without having to change their flow direction.

A separation plate 10 configured in accordance with the dimensions (all in inches) shown in FIGS. 6B and 6C is designed to have a cut size of about 1.0 microns at a flow rate of 35 liters per minute (1 pm). It should be understood that those of ordinary skill in the art might readily optimize separation plate 10 to meet a specific cut size requirement at a predefined flow rate. For example, the cut size of a separation plate may be modified by scaling up or down the various structures provided on the separation plate. Larger nozzles with proportionally larger virtual impactors are useful in separating larger particulates, while conversely, smaller nozzles with proportionally smaller virtual impactors are useful in separating smaller particulates. The cut size of a separation plate may also be modified by adjusting a flow rate through the separation plate.

With reference to FIG. 6D, for particulates having from about 1 to about 3 micron diameters, it has been found that making the dimension "a" greater than the dimension "b" generally reduces recirculation of a minor flow upon entering minor flow passage 30, which is preferable for efficiently separating a minor flow from a major flow. For larger particulates, it may be preferable to make "b" larger than "a" to reduce pressure drop.

Figure 6E:
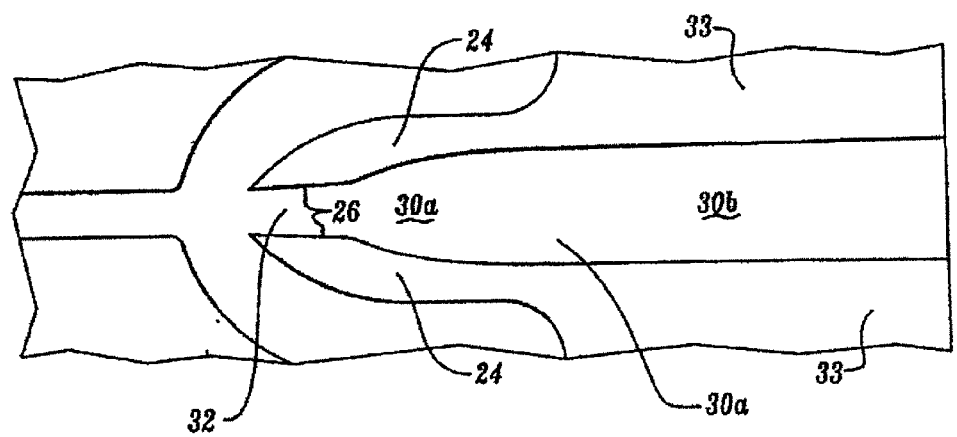

FIG. 6E illustrates modified configurations of a nozzle 14 and a virtual impactor 16, wherein inner walls 26 of fin-shaped projections 24 include a generally concave surface. Accordingly, the width of upstream minor flow passage 30a expands from inlet end 32 toward downstream minor flow passage 30b, which is defined between the external walls of adjacent virtual impactor bodies 33. This configuration is advantageous in reducing particulate loss onto inner walls 26.

A separation plate may be easily modified to process virtually any volume of fluid stream at any flow rate, by varying the number of nozzles 14 and virtual impactors 16 provided on the separation plate. Furthermore, the throughput of separation plate 10 may be almost indefinitely modified by increasing or decreasing height "H" of nozzles 14, virtual impactors 16, and virtual impactor bodies 33. It should be noted that height "H" of a separation plate could be freely increased without a significant increase in particulate loss. This capability is made possible by the design of this virtual impactor that allows minor flows to advance straight through without experiencing any deflected path.

Figure 7A:
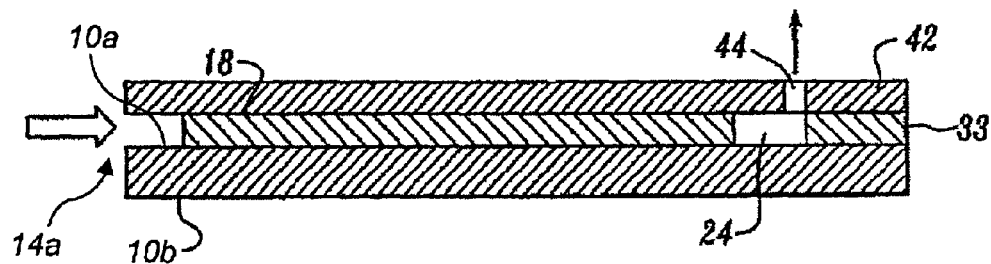
FIG. 7B is a schematic perspective view of an alternative configuration of a virtual impact collector in accord with the present invention.

Separation plate 10 may be readily incorporated into various particulate separation/concentration apparatus for use in the present invention. Referring to FIG. 7A, for example, a virtual impact collector may be formed by placing a cover plate 42 over projections 18, fin-shaped projections 24, and virtual impactor bodies 33 provided on first surface 10a. Cover plate 42 and first surface 10a cooperatively define a chamber. Inlet ends 14a of the nozzles provide an inlet through which a particulate-laden fluid stream may enter the chamber. Minor flow passages 30 (see FIG. 6B) provide an outlet through which a minor flow may exit the chamber; however, an outlet through which a major flow may exit the chamber may be provided in various other ways. For example, as in FIGS. 6B and 6C, the plurality of orifices 34 defining terminal ends of passageways 36 may be provided through virtual impactor bodies 33. Alternatively, as in FIG. 7A, cover plate 42 may include a plurality of orifices 44 that extend therethrough. Orifices 44 are configured and arranged so that when cover plate 42 is mated with separation plate 10, orifices 44 are disposed between virtual impactors 16 and adjacent to the upstream end of virtual impactor bodies 33, to exhaust major flows flowing around virtual impactors 16 (see FIG. 6B) that are blocked by bodies 33, as indicated by the arrow.

Figure 7B:
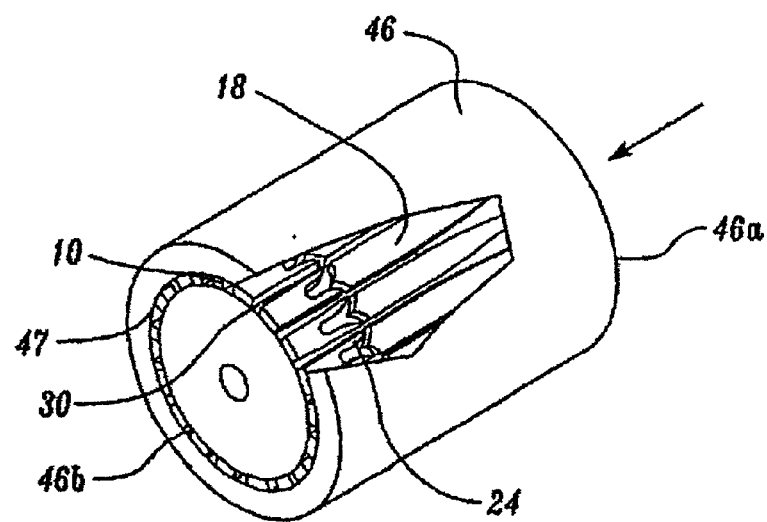

A further example of a virtual impact collector suitable for use in the mail sampling system is schematically illustrated in FIG. 7B. In this embodiment, separation plate 10 of FIG. 6B is joined at its opposing edges 45 to form a cylinder. The second surface of separation plate 10 forms the inner surface of the cylinder. Cylindrical separation plate 10 is coaxially slid into a tube 46 having two open ends 46a and 46b to form an annular chamber 47 therebetween. As before, a suitable major flow outlet (not shown) is provided. In operation, particulate-laden fluid streams enter chamber 47 through the inlet ends of the nozzles defined between nozzle projections 18, adjacent to open end 46a. Minor flow passages 30 provide an outlet through which a minor flow exits chamber 47. A suitably provided major flow outlet deflects a major flow to either or both of the inner surfaces of the cylindrical separation plate 10 and/or the outer surface of tube 46.

Figure 8A:
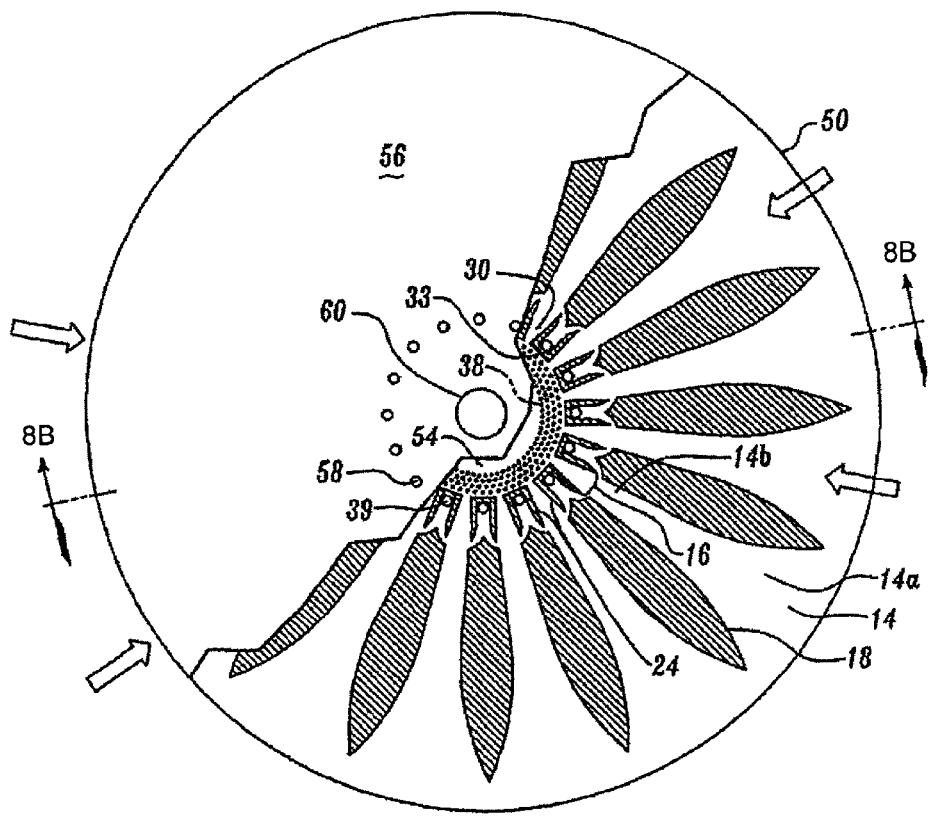
FIG. 8A is a plan view of a virtual impact collector incorporating plural pairs of a nozzle and a virtual impactor arranged radially.
Figure 8B:
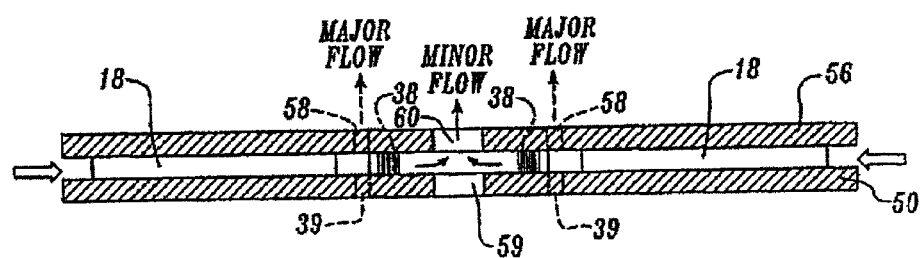
FIG. 8B is a cross-sectional view of the virtual impact collector taken along section line 8B—8B of FIG. 8A.

FIGS. 8A and 8B schematically illustrate a radial virtual impact collector including a separation plate 50 and a cover plate 56. Separation plate 50 includes plural pairs of nozzles 14 and virtual impactors 16; the virtual impactors are disposed radially inward of nozzles 14. As before, nozzle 14, which has an inlet end 14a and an outlet end 14b, is defined between adjacent nozzle projections 18. Virtual impactor 16 comprises a pair of fin-shaped projections 24 disposed downstream and radially inward of outlet end 14b of each nozzle 14. As before, fin-shaped projections 24 in each pair are spaced apart and define minor flow passage 30 therebetween. Also as before, a plurality of virtual impactor bodies 33 in the form of a wall extend between the downstream ends of fin-shaped projections 24 of adjacent virtual impactors 16. A plurality of orifices 39 are provided through separation plate 50 radially outward of virtual impactor bodies 33 and between fin-shaped projections 24 of adjacent virtual impactors 16. Virtual impactors 16 and bodies 33 together define a central minor flow collection portion 54. A plurality of impactor pillars 38 are disposed radially inward and downstream of minor flow passages 30, within central minor flow collection portion 54. Impactor pillars 38 are employed to receive a minor flow and to collect particulates thereon, as more fully described below. A minor flow outlet 59 is provided through separation plate 50 near the center of central minor flow collection portion 54. Separation plate 50, which is described above, may be combined with cover plate 56 to form the virtual impact collector. Cover plate 56 is configured to mate with separation plate 50 to define a chamber therebetween. Cover plate 56 optionally include holes 58 that are configured and arranged so that when separation plate 50 and cover plate 56 are combined, holes 58 are aligned to coincide with holes 39 defined through separation plate 50. Optionally, cover plate 56 may include a minor flow outlet 60 defined therethrough. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particulate-laden fluid streams enter nozzles 14 through inlet ends 14a and advance radially inward. When aerodynamically focused fluid streams advance toward virtual impactors 16, they are separated into a minor flow and a major flow, as described above. The major flow flows around virtual impactors 16, is redirected by bodies 33, and is exhausted through either or both of holes 39 in separation plate 50 and/or holes 58 in cover plate 56. The minor flow advances through minor flow passages 30 into central minor flow collection portion 54. When impactor pillars 38 are provided, some of the particulates entrained in the minor flow may impact and become deposited on impactors 38. The particulates collected on impactor pillars 38 may be subsequently collected, for example, by washing impactor pillars 38 with a small amount of liquid to capture the particulates therein. An example of impactors suitable for use in conjunction with the present invention can be found in U.S. Pat. No. 6,110,247, filed Nov. 13, 1998, concurrently with a parent case hereof, and assigned to the same assignee, the disclosure and drawings of which are expressly incorporated herein by reference. The minor flow may be exhausted from central minor flow collection portion 54 through either or both of minor flow outlets 59 and 60.

When both minor flow outlets 59 and 60, and both holes 39 and 58 are provided, as illustrated in FIG. 8B, a plurality of the virtual impact collectors described above may be stacked together to process a large fluid volume. The stacked virtual impact collectors include a common minor flow exhaust conduit comprising minor flow outlets 59 and 60, and a common major flow exhaust conduit comprising holes 39 and 58.

Figure 9A:
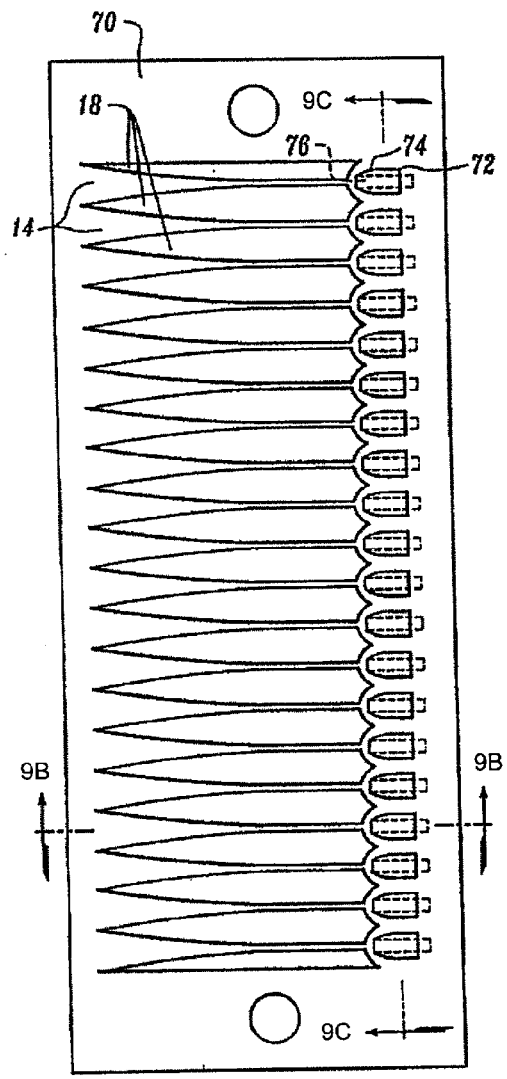
FIG. 9A is a plan view of another configuration of a separation plate in accordance with the present invention.
Figure 9C:
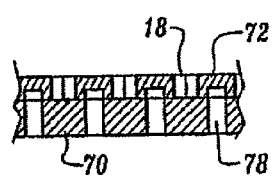
FIG. 9C is a cross-sectional view of the separation plate taken along section line 9C—9C of FIG. 9A.
Figure 9B:
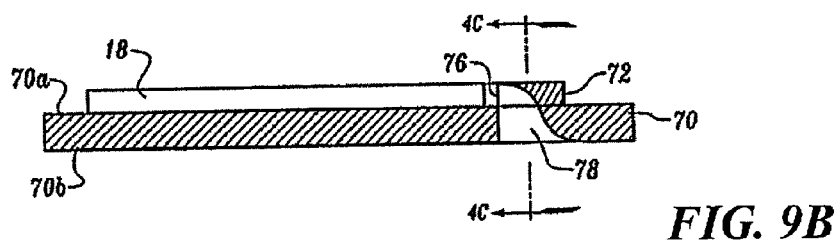
FIG. 9B is a cross-sectional view of the separation plate taken along line 9B—9B of FIG. 9A.

FIGS. 9A, 9B, and 9C illustrate another embodiment of a separation plate 70. As in the first embodiment, separation plate 70 includes a first surface 70a and an opposing second surface 70b. First surface 70a is provided with a plurality of nozzle projections 18 that define nozzles 14 therebetween. As before, nozzle 14 tapers from an inlet end 14a to an outlet end 14b. Downstream of each outlet end 14b is provided a generally haystack-shaped virtual impactor projection 72. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70b of separation plate 70. Alternatively, minor flow passage 78 and virtual impact void 76 may be formed by drilling a hole through separation plate 70, so that minor flow passage 78 passes through separation plate 70 at an acute angle and the minor flow containing a major portion of particulates will avoid sharp changes in direction upon entering virtual impact void 76. It should be noted that the longer minor flow passage 78, the more particulates may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 are to be determined based partly on the limitations imposed by the available micromachining methods. An angle of between approximately 15° and 45°, which is possible with currently available micromachining methods, should provide satisfactory results.

In operation, particulate-laden fluid streams flow along first surface 10a through nozzles 14 and advance toward convex surfaces 74 of virtual impactor projections 72. Major flows continue around projections 72 to avoid obstruction presented by convex surfaces 74, and flow along first surface 10a. Minor flows are collected in a zone of stagnant fluid created near convex surfaces 74, and enter virtual impact voids 76 defined through convex surfaces 74. The minor flows travel through minor flow passages 78 to second surface 70b, where they can be collected, and analyzed or processed after being archived, as discussed herein. Thus, unlike separation plates 10 and 50 of the previous embodiments, separation plate 70 of the present embodiment separates a particulate-laden fluid stream into a minor flow on the second surface, and a major flow on the first surface.

Another embodiment of a separation plate 100 is illustrated in FIGS. 10A and 10B. A separation plate 100 includes a central passage 102 that extends laterally across the length of the separation plate and through its width. The passage is defined between plates 104a and 104b and is machined within the facing surfaces of these two plates, which preferably comprise a metal such as steel, aluminum, titanium, or another suitable material such as plastic. Alternatively, the passage can be formed by molding or casting the plates from metal, or another suitable material, such as plastic. Passage 102 is readily formed in the surfaces of each of plates 104a and 104b by conventional machining techniques. Since the surfaces are fully exposed, the desired telescoping or converging configuration of the passage is readily formed. The passage extends from an inlet 108, which is substantially greater in cross-sectional area due to its greater height compared to that of an outlet 106. The outlet is disposed on the opposite side of the separation plate from the inlet. Inlet 108 tapers to a convergent nozzle 110, which further tapers to the opening into a minor flow portion 112 of passage 102.

In this preferred embodiment of separation plate 100, one-half of the thickness of passage 102 is formed in plate 104a, and the other half of the thickness of the passage is formed in plate 104b. However, it is also contemplated that the portions of the passage defined in each of plates 104a and 104b need not be symmetrical or identical, since a desired configuration for passage 102 can be asymmetric relative to the facing opposed surfaces of the two plates.

Immediately distal of the point where minor flow portion 112 of passage 102 begins, slots 115a and 115b are defined and extend transversely into the plates relative to the direction between the inlet and the outlet of passage 102 and extend laterally across separation plate 100 between the sides of the passage. Slots 115a and 115b respectively open into major flow outlet ports 114a and 114b in the ends of plates 104a and 104b, as shown in FIG. 10A. Threaded fastener holes 116 are disposed on opposite sides of each of major flow outlet ports 114a and 114b and are used for connecting a major flow manifold (not shown) that receives the major flow of fluid in which the minor portion of the particulates greater than the cut size is entrained.

Fastener holes 118a are formed through plate 104b adjacent to its four corners and do not include threads. Threaded fasteners (not shown) are intended to be inserted through holes 118a and threaded into holes 118b, which are formed at corresponding corner positions on plate 104a. The threaded fasteners thus couple edge seals 120 on the two plates together, sealing the edges of passage 102 and connecting plates 104a and 104b to form separation plate 100. Although not shown, a manifold may also be connected to the back surface of separation plate 100 overlying outlet 106 to collect the minor flow of fluid in which the major portion of particulates exceeding the cut size is entrained. In FIG. 10A, the flow of fluid entering inlet 108 of passage 102 is indicated by the large arrow, the major flow exiting major flow ports 114a and 114b is indicated by the solid line arrows, and the minor flow exiting outlet 106 of passage 102 is indicated by the dash line arrow. The cross-sectional profile of passage 102 as shown in FIG. 10B focuses the particulate-laden fluid flow entering inlet 106 for delivery to the receiving nozzle and thus performs in much the same way as the profile used in the previous embodiments of virtual impactors.

The desired flow through the separation plate will determine the width of passage 102, as measured along the longitudinal axis of the separation plate, between sealed edges 120. Additional fluid flow can also be accommodated by providing a plurality of the separation plates in an array, which will also avoid using extremely long and thin structures that may not fit within an available space. FIG. 10B illustrates two such additional separation plates 100' and 100", stacked on each side of separation plate 100, so that the fluid enters the inlets of the stacked separation plates and is separated in the major flow and the minor flow exiting the separation plates, as described above.

Figure 11A:
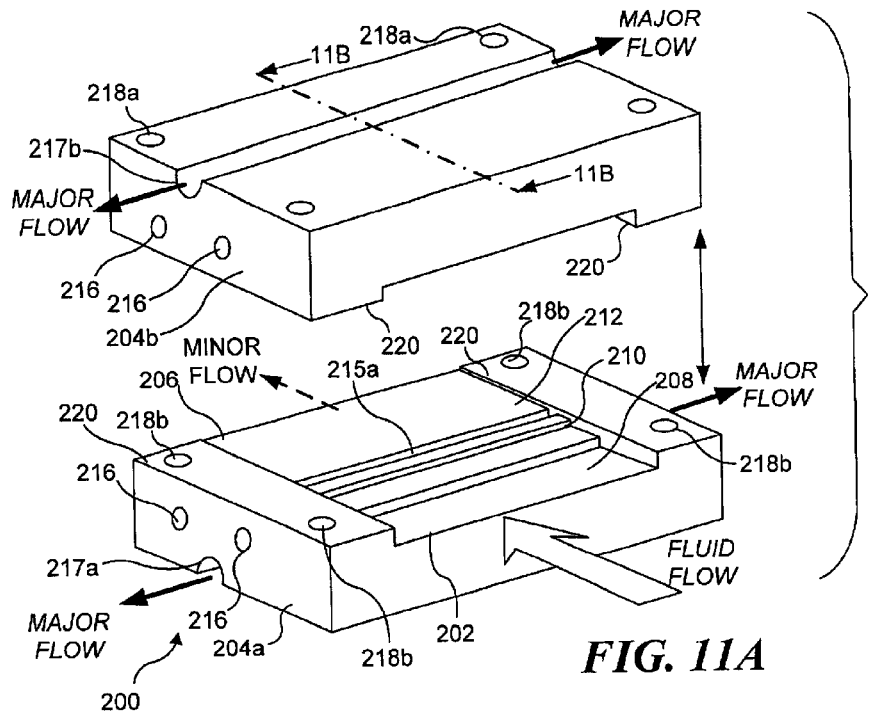
FIG. 11A is an isometric view of still another alternative embodiment of a separation plate in accord with the present invention.
Figure 11B:
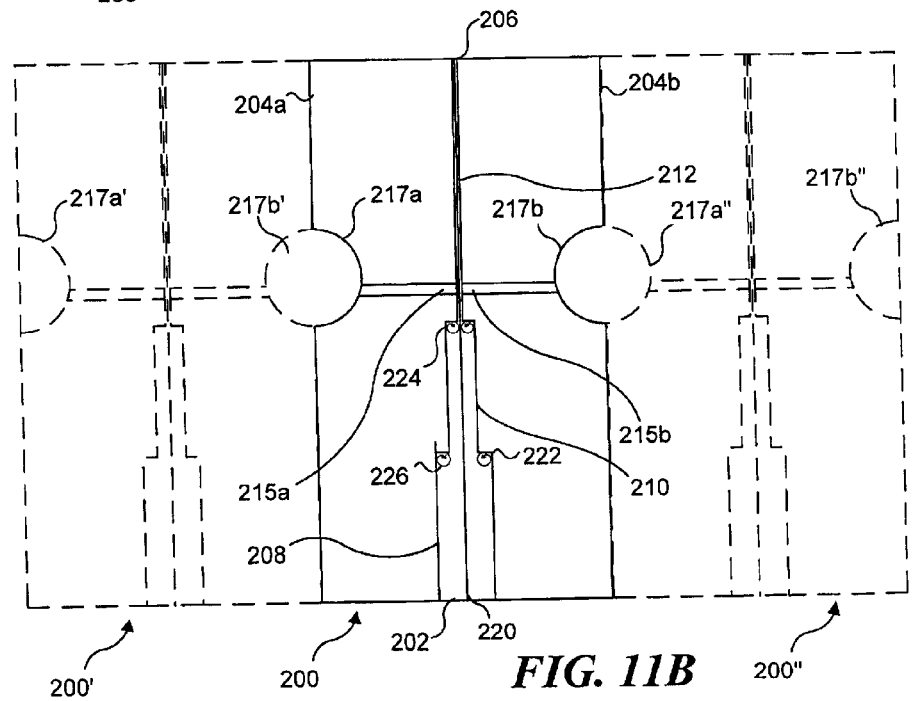
FIG. 11B is a cross-sectional view of the separation plate of FIG. 11A, taken along section lines 11B—11B, showing additional separation plates arrayed on each side in phantom view.

FIGS. 11A and 11B illustrate still another embodiment of a separation plate 200 that is similar to separation plate 100, which was discussed above in regard to FIG. 10. Separation plate 200 differs from separation plate 100 in at least two significant ways, as will be apparent from the following discussion. To simplify the following explanation of separation plate 200, the reference numbers applied to its elements that are similar in function to those of separation plate 100 are greater by 100. Thus, like central passage 102 in separation plate 100, separation plate 200 includes a central passage 202 that extends laterally across the length of the separation plate and through its width. The passage is defined between plates 204a and 204b and is machined within the facing surfaces of these two plates, which also preferably comprise a metal such as steel, aluminum, or titanium formed by machining or by molding the plates from metal, or another suitable material such as a plastic. The passage extends from an inlet 208, which is substantially greater in cross-sectional area due to its greater height, to an outlet 206 disposed on the opposite side of the separation plate from the inlet. Unlike inlet 108 of the previous embodiment, which tapers to a convergent nozzle 110 and then to a minor flow portion 112 of passage 102, the central passage in separation plate 200 does not taper to smaller cross-sectional sizes. Instead, the central passage in separation plate 200 changes abruptly to a smaller cross-sectional size at a step 222, continuing through a section 210, and then again decreases abruptly to a smaller minor flow outlet 212, at a step 224. At each of steps 222 and 224, a swirling flow or vortex 226 of the fluid is produced. It has been empirically determined that these vortexes tend to focus the particulates toward the center of the passage, thereby providing a substantial improvement in the efficiency with which the particulates smaller than the cut size are separated from the particulates larger than the cut size.

In this preferred embodiment of separation plate 200, one-half the thickness of passage 202 is formed in plate 204a, and the other half of the thickness of the passage is formed in plate 204b, just as in the previous embodiment. And again, it is contemplated that the portions of the passage defined in each of plates 204a and 204b need not be symmetrical or identical, since a desired configuration for passage 202 can be asymmetric relative to the facing opposed surfaces of the two plates.

Immediately distal of the point where minor flow portion 212 of passage 202 begins, slots 215a and 215b are defined and extend transversely into the plates relative to the direction between the inlet and the outlet of passage 202 and extend laterally across separation plate 200 between the sides of the passage, just as in separation plate 100. Slots 215a and 215b respectively open into major flow outlet ports 217a and 217b, which are open to the ends and outer surfaces of plates 204a and 204b, as shown in FIG. 11A. In this embodiment, separation plate 200 is designed to be stacked with other similar separation plates 200' and 200", as shown in FIG. 11B, so that adjacent separation plates cooperate in forming the passage for conveying the major flow into an overlying major flow manifold (not shown). It is also contemplated that separation plate 100 can be configured to include major flow outlet ports similar to those in separation plate 200. The last plate disposed at the top and bottom of a stack of separation plates configured like those in FIG. 11B would include major flow outlet ports 114a and 114b, respectively. Threaded fastener holes 216 are disposed on opposite sides of each of major flow outlet ports 217a and 217b and are used for connecting a major flow manifold (not shown) that receives the major flow of fluid in which the minor portion of the particulates greater than the cut size is entrained.

Fastener holes 218a are formed through plate 204b adjacent to its four corners and do not include threads. Threaded fasteners (not shown) are intended to be inserted through holes 218a and threaded into holes 218b, which are formed at corresponding corner positions on plate 204a. The threaded fasteners thus couple edge seals 220 on the two plates together, sealing the edges of passage 202 and connecting plates 204a and 204b to form separation plate 200. Although not shown, a manifold may also be connected to the back surface of separation plate 200 overlying outlet 206 to collect the minor flow of fluid in which the major portion of particulates exceeding the cut size is entrained, for use in creating an archive of the samples thus collected as explained below. In FIG. 11A, the flow of fluid entering inlet 208 of passage 202 is indicated by the large arrow, the major flow exiting major flow outlet ports 217a and 217b is indicated by the solid line arrows, and the minor flow exiting outlet 206 of passage 202 is indicated by the dash line arrow.

Separation plates 100 and 200 cost less to manufacture than the other embodiments discussed above. As was the case with separation plate 100, the desired flow through the separation plate will determine the width of passage 202 along the longitudinal axis of the separation plate, between sealed edges 220, and additional fluid flow can also be accommodated by providing a plurality of the separation plates in an array configured to fit within an available space. FIG. 11B illustrates two additional separation plates 200' and 200", stacked on opposite sides of separation plate 200, so that the fluid enters the inlets of the stacked separation plates and is separated in the major flow and the minor flow exiting the separations plates, as described above.

Figure 12:
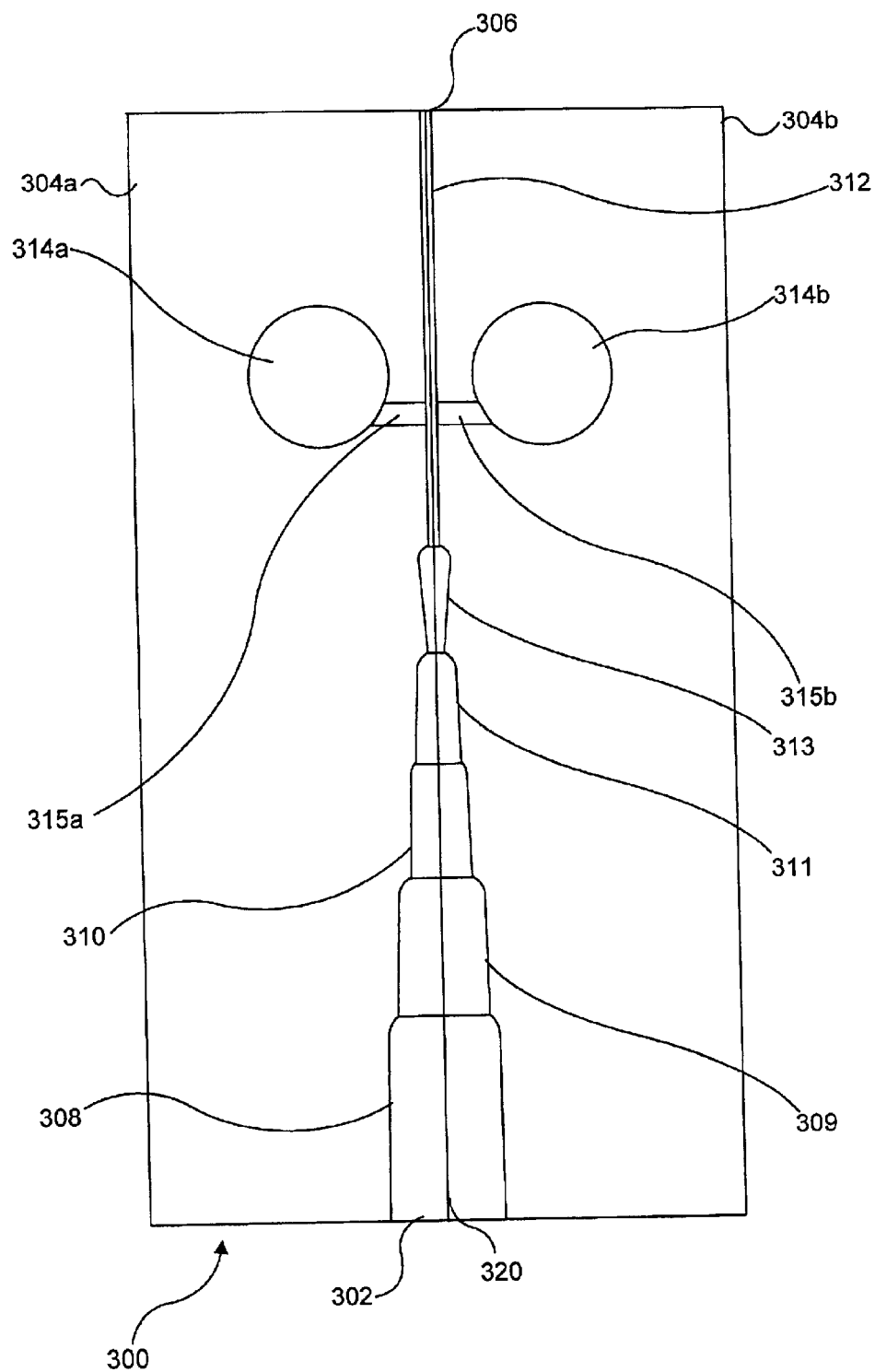
FIG. 12 is a cross-sectional view of a separation plate like that shown in FIGS. 10A and 10B, but having a slightly modified passage through which the fluid flows to optimize the efficiency of separation over a broader range of particulate sizes.

Finally, a separation plate 300 is illustrated in FIG. 12. Separation plate 300 is also similar to separation plate 100, which is shown in FIGS. 10A and 10B, but includes a central passage 302 that differs from central passage 102 in separation plate 100. Again, to simplify the following explanation, reference numbers applied to the elements of separation plate 300 that are similar in function to those of separation plate 100 are greater by 200. It will thus be apparent that central passage 102 in separation plate 100 corresponds to central passage 302 in separation plate 300 and that central passage 302 extends laterally across the length of separation plate 300 and through its width. The passage is defined between plates 304a and 304b and is machined within the facing surfaces of these two plates, preferably from a metal such as steel, aluminum, or titanium formed by machining, or by molding the plates from metal, or another suitable material such as a plastic. As described above, fasteners can be employed to couple edge seals 320 on the two plates together, sealing the edges of passage 302 and connecting plates 304a and 304b to form separation plate 300. The passage extends from an inlet 308, which is substantially greater in cross-sectional area due to its greater height, to an outlet 306 disposed on the opposite side of the separation plate from the inlet. Central passage 302 comprises a telescoping section that performs aerodynamic focusing of the particulates so as to achieve a further optimization in maximizing the efficiency of the separation plate over a wider range of particulate sizes, compared to the other embodiments. The focusing is accomplished in this embodiment by using a combination of contracting and diverging sections. Specifically, an inlet 308 tapers slightly at its distal end to a more convergent section 309, which again tapers to a convergent nozzle 310, which further tapers at its distal end to another convergent section 311. The distal end of convergent section 311 tapers into the proximal end of a divergent section 313, and its distal end then tapers into a minor flow portion 312 of central passage 302. Distal of the point where minor flow portion 312 of central passage 302 begins, slots 315a and 315b are defined and extend transversely into the plates relative to the direction between the inlet and the outlet of central passage 302 and extend laterally across separation plate 300 between the sides of the passage. Major flow outlet ports 314a and 314b can be used for connecting to a major flow manifold (not shown) that receives the major flow of fluid in which the minor portion of the particulates greater than the cut size are entrained.

As will be apparent from the preceding description, a number of less abrupt steps are used in the central passage of separation plate 300 than in the preceding embodiments of FIGS. 10A and 10B, and 11A and 11B, to improve the efficiency of separating larger particulates (i.e., approximately 5□ to 10□ in size); larger particulates tend to have greater wall losses due to impaction on the "steps" of the telescoping profile. The less abrupt steps will not focus the small particulates as well as in the other embodiments, however, the outward expansion provided by diverging section 313, followed by a final steep step into minor flow passage 312 to focus the small particulates seems to improve the efficiency of the separation (at least in simulations). The flow of larger particulates does not expand out much in diverging section 313, and is thus less likely to impact on the final step into minor flow passage 312.

In all other respects, separation plate 300 operates like separation plate 100, and can be modified to collect the major flow like separation plate 200. It will also be apparent that a plurality of separation plates 300 can be stacked, just as in the previous embodiments, to increase the volume of fluid processed.

Prefilters

Figure 3A:
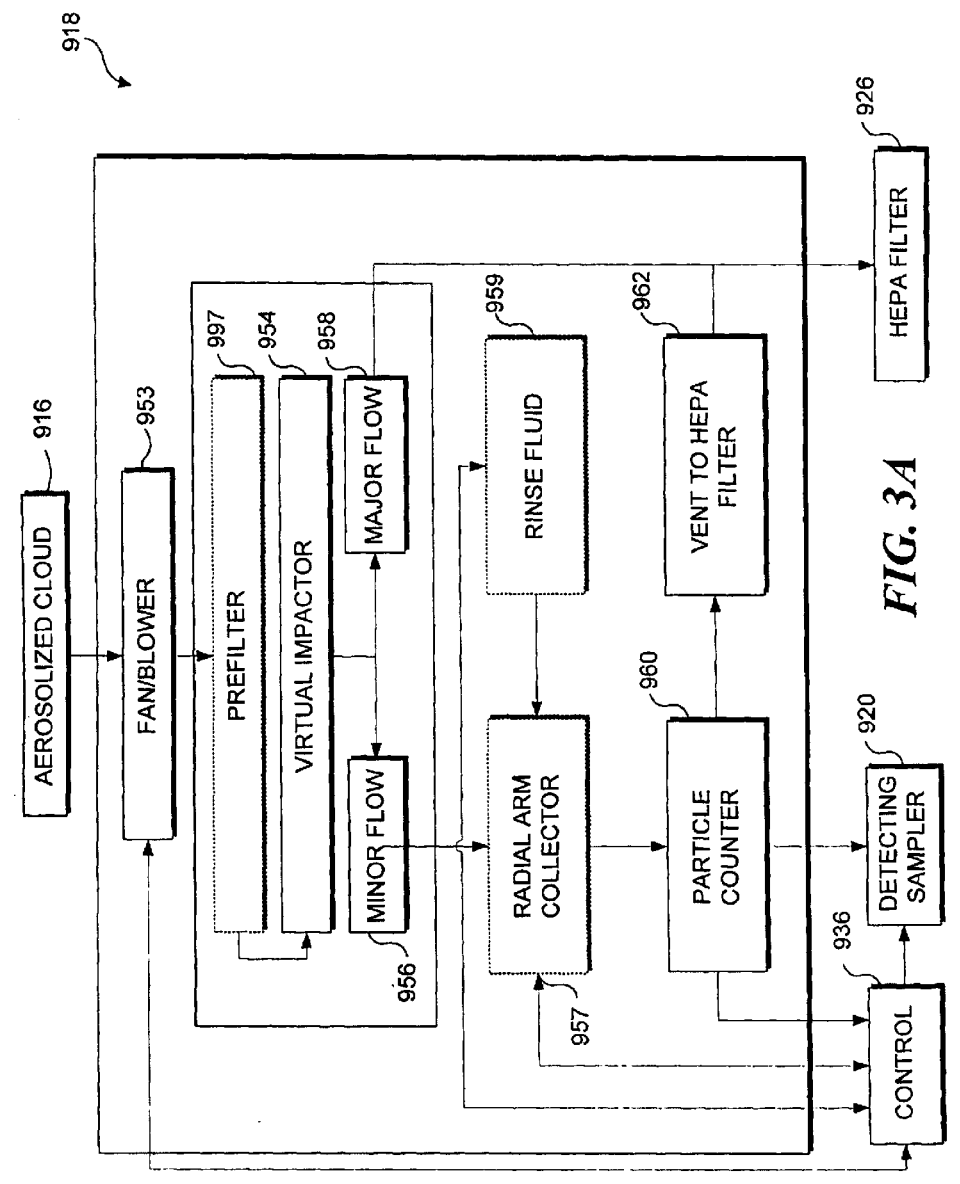

An optional, but preferred component, is a prefilter employed to remove large fiber particles from the air directed into the samplers. A prefilter is preferably used before each sampler in order to remove large paper fibers and other unwanted particles from the air. To ensure that the prefilter does not remove much, if any, of the chemical or biological agents being screened for, the prefilter must be selected based on the size of the anticipated contaminant, to ensure that the anticipated contaminant is readily able to pass through the prefilter. The prefilter can be purely passive, such as a filter or a series of sieves. Any conventional air filter, such as a fiber or polymer filter, can be employed, as long as the filter enables the contaminants to pass. Note that if fiber filters are employed, such filters should themselves not be an additional source of fiber particles. The prefilter could also be a virtual impactor. As described in detail above, virtual impactors separate particles entrained in a flow of fluid into a fluid flow containing particles over a certain cut size (such as large paper fibers) and a fluid flow containing particles less than the cut size (such as potential contaminants and small paper fibers). When employed as a prefilter, a virtual impactor would separate the air to be sampled into a first stream containing large paper fibers and little or none of the contaminant, and a second stream containing smaller fiber particles and the contaminant (if present). The first stream is exhausted through the HEPA filter, and the second stream is delivered to the sampler (in some cases, the second stream is delivered to the inlet of an additional virtual impactor servicing the sampler, as described above. When employed as a prefilter, it is anticipated that a 30 micron cut size will be preferred, and the when employed to concentrate particles into a fluid stream to be sampled, that a preferred cut size will be 1–5 microns. A prefilter 997 is illustrated in FIG. 3A. While not shown in conjunction with other sampling systems, it should be understood that prefilters can be employed with any or all of the sampling systems described below (triggering samplers, detecting samplers, and archiving samplers).

Triggering Sampler

The air in immediate proximity to the opened mail (or compressed package) is continually analyzed for particle content. In one embodiment, particle count alone is monitored, while in at least one other embodiment, the triggering sampler is able to differentiate biological particles from particles of non-biological origin. As discussed above with respect to FIG. 1, the triggering sampler is preferably electrically coupled to an integrated controller, such as a processor and a controlling algorithm, which receives telemetry from the particle counter. If a particle count threshold is reached, or a positive determination of the presence of any biological particle occurs, the controller activates the detecting sampler system (and optionally, the archiving sampler system). As noted above, if the controller is not incorporated into the mail sampling system, then the triggering sampler can be directly coupled to the detecting sampler (and archiving sampler if desired), so that once a particle count threshold is met, or a threshold number of biological particles are counted, the detecting sampler (and archiving sampler if desired) are activated by a signal received from the triggering sampler.

The term "triggering sampler" is indicative of the function of this component, in that the triggering sampler is used to "trigger" or activate the operation of the second air sampling system (the detecting sampler). The triggering sampler is designed to continuously monitor the level of particles in the air within the containment chamber, and when a predefined threshold value or count is exceeded, the triggering sampler causes the second sampler system to obtain a sample of the particles. The second sample can then be analyzed within the mail sampling system (if it is equipped with detectors capable of such analysis) or the sample can be removed for analysis.

The triggering sampler, the detecting sampler, and the archiving sampler (if employed) each preferably include a virtual impactor to concentrate the particulates in the minor flow of the virtual impactor. As described above, virtual impactors enable even small amounts of particulates to be more easily counted and analyzed, by providing a more concentrated sample. Virtual impactor collector technology enables sampling of a much higher volume of air, and isolates the majority of particles in a low flow rate stream. The typical concentration factor is 10, although it will be apparent to those skilled in the art that multiple virtual impactor collectors could be arranged in series to produce a concentration factor of 100 or more. The virtual impact collector technology performs the dual roles of drawing in air via a fan and concentrating the particulate matter via inertial flow splitting.

Simpler embodiments could use a fan or other fluid moving apparatus to draw air into the sampler (triggering, detecting, or archival). Particulate concentration is preferred but not essential in determining whether mail is contaminated. An increased concentration of particulates in the fluid processed by each sampler offers two advantages. The first advantage is that increasing the particle concentration also increases the concentration seen by the sampler, thereby lowering the limit of detection. The second advantage is more profound in the context of the present invention, since it enables a much higher volumetric flow rate of air to be sampled.

FIG. 3A is a block diagram illustrating the components of triggering sampler 918. An optional prefilter 997, described in more detail below, can be employed to remove particles (such as paper fibers) that are significantly larger in size than the anticipated biological or chemical particles of interest. While only shown in FIG. 3A, it should be understood that prefilters could be incorporated into other embodiments of samplers (i.e. triggering, detecting and archiving samplers). As noted above, a virtual impactor 954 separates a fluid flow (with entrained particulates) into a minor flow 956 and a major flow 958. As described above with respect to virtual impactors, such virtual impactor can be designed to achieve a significant concentration (based on particle mass) of particles of a targeted mass in the minor flow. Preferably, the major flow is directed to HEPA filter 926 to remove any particulates that might be entrained in the major flow, before that fluid (air) is vented from the containment chamber. It should be understood, as is shown in FIG. 1, that triggering sampler 918 is entirely contained within containment chamber 902. As shown in FIG. 3A, a fan/blower 953 is used to draw air from the containment chamber and force it into virtual impactor 954. An inlet for fan/blower 953 is disposed to draw the air from aerosolized cloud 916, which is generated by aerosolizing means 912.

The minor flow, containing the majority of the particulates of a desired mass/size, is directed to a particle counter 960, which operates continuously to determine a relative number of particles contained in the minor flow, i.e., a relative indicator of the number of particulates per volume of air sampled. Preferably particle counter 960 is designed to ignore particle counts below a predetermined level. The predetermined level is empirically determined to avoid too many samples being collected by the detecting sampler, resulting in too many false positives. An increased number of particles in the background (i.e., particulates that are not contaminants) is particularly likely if the parcel has been punctured via a mechanical perforator, which is likely to produce envelope particulates that could be counted by particle counter 960. Furthermore, because most chemical and biological agents likely to be sent in the mail are particulate in nature (for example, anthrax spores), a contaminated parcel is likely to generate a very substantial increase (spike) in the particle count, relative to the previous background level. It is such a substantial increase that the increase is the best indication of a contaminated parcel, not the detection of a specific number of particles. Preferably, a threshold value will be obtained by processing a large volume of mail that is known to be uncontaminated through mail sampling system 900, with the particle counter of triggering sampler 918 set to continuously record the particle count within the containment chamber during processing of mail. It is likely that dirt and dust associated with the volume of mail processed will indeed result in a measurable number of particulates. The results obtained by particle counter 960 can then be used to set a threshold value for processing mail that is likely to be contaminated. Alternatively, the threshold can be defined as a percentage deviation relative to the average count for a batch of mail currently being processed.

Once particulates have been detected by particle counter 960 (preferably in a quantity that exceeds the threshold value as discussed above), a signal is provided to activate the detecting sampler, so that a sample of the potentially suspect particulates can be obtained. Once such a sample is obtained, the particulates are analyzed to determine if a chemical or biological agent is present. In one embodiment, particle counter 960 sends a signal to control 936 indicating that the threshold level has been exceeded, which in turn sends a signal to detecting sampler 920, to activate it. Alternatively, particle counter 960 sends a signal directly to detecting sampler 920 to activate it response to the threshold level being exceeded. After passing through particle counter 960, the minor flow of fluid that might include particulates is directed to HEPA filter 926 to remove any particulates entrained in the minor flow, before the fluid (air) is vented from the containment chamber.

Also shown in FIG. 3A are an optional radial arm collector 957, and a rinse fluid reservoir 959. Radial arm collector 957 will be discussed in greater detail below. Empirical data indicate that radial arm collectors are very efficient at removing particles entrained in a flow of fluid. In this device, a flow of fluid having entrained particles is directed at a rotating radial arm (driven by a prime mover drivingly coupled to the rotating radial arm). The particulates impact on the radial arm, and a significant number of the impacted particulates are deposited on the radial arm. After a defined sampling period elapses, a rinse fluid is directed onto the radial arm and the deposited particulates are rinsed off the arm and collected. Generally, the rinse fluid is an inert liquid, such as sterilized water. While particle counters do not require a liquid sample, many other analytical devices do. Because particle counters do not require a liquid sample, radial arm collector 957 and rinse fluid reservoir 959 are optional components of triggering sampler 918. However, it is anticipated that the inclusion of radial arm collector 957 and rinse fluid reservoir 959 will enhance the efficiency with which particles can be collected and counted, and then subsequently analyzed. While not shown, it should be understood that a conventional power supply is required to energize fan/blower 953, radial arm collector 957, and particle counter 960. Note that as illustrated in FIG. 3A, a separate prime mover is not shown. It should be understood that the prime mover required to drive the radial arm is part of radial arm collector 957, as will become clear in the section below which describes the radial arm collector in greater detail.

The signal produced in response to the detection of particulates exceeding a threshold value by the triggering sampler can be used not only to activate the detecting sampler, but also to activate alarm 934 (see FIG. 1) as well. It is contemplated that alarm 934 could be coupled directly to the particle counter, or alternatively, coupled to control 936, which in turn is coupled to particle counter 960. Alarm 934 is particularly useful in embodiments of mail sampling system 900 that do not include identification unit 924 (FIG. 1). Such embodiments require an operator to retrieve the sample collected by detecting sampler 920 for analysis outside of mail sampling system 900. The alarm thus notifies the operator that a sample needs to be retrieved and analyzed. Preferably, mail sampling system 900 is idled so that mail stops moving through it, until such a sample is analyzed. At that time, a contaminated parcel can be retrieved and mail sampling system 900 decontaminated, or if the results indicate a non-threatening particulate, mail sampling system 900 can be restarted.

Particle counters are well known in the art, and there are many examples of such devices commercially available. In one type of product particularly well-suited for use in the present application, a laser is used to simultaneously count particles while probing them for fluorescence. If a particular type of fluorescence is detected, the particle is properly classified as biological. Use of such a particle counter provides a real time value for both particle count, and biological particle detection and count. Preferably, at the triggering sampler, if the overall particle count exceeds a predetermined threshold value, or if the biological particle count exceeds a biological particle threshold value, the detecting sampler is activated to perform analysis. In at least one embodiment of the present invention, the archiving sampler is activated each time the detecting sampler is activated, to create an additional archived sample.

Preferably, biological particulates are identified in response to a laser-induced autofluorescence of nicotinamide adenine dinucleotide hydrogen (NADH) and nicotinamide adenine dinucleotide phosphate hydrogen (NADPH). NADH is necessary for thousands of biochemical reactions and is found naturally in every living cell. NADH plays a key role in the energy production of cells. The more NADH a cell has available, the more energy it can produce to perform its process efficiently. NADH, which is referred to by biologists as coenzyme 1, is the reduced form of nicotinamide adenine dinucleotide (NAD), with an additional hydrogen (H) atom and provides energy to cells. Note that viable biological agents such as anthrax can be detected and counted using laser-induced autofluorescence of NADH. NADPH is the reduced form of nicotinamide adenine dinucleotide phosphate (NADP), which functions similarly to NAD, and is structurally similar except for the addition of a phosphate group.

In one preferred embodiment shown in FIG. 3B, particle counter 960 comprises a nano-ultraviolet (nano-UV) diode pumped solid state laser 962, emitting light having a wavelength of about 355 nm (near the absorption peak of NADH) and mini photomultiplier tube (PMT) optical detectors 964 for collection of particle fluorescence and elastic scatter information. This type of particle counter can detect as few as 25 biological particles per liter of air in real-world environments, and even fewer in HEPA filtered environments. Similar UV lasers, having an emission wavelength of approximately 370 nm, can also be beneficially employed. It is further anticipated that other types of photon sensors (besides PMTs) can be beneficially employed. Photodiode technology is improving, and photodiodes may soon be readily available with sensitivities low enough to enable them to replace PMTs.

In at least one embodiment, control 936 is coupled to fan/blower 953 to ensure that the fan/blower is energized whenever mail sampling system 900 is operating. Control 936 is also preferably employed to control the operation of radial arm collector 957 and rinse fluid reservoir 959, when these components are included in the system.

Detecting Sampler

As described above, triggering sampler 918 continually monitors the air in the immediate proximity to the opened mail (or stressed package) for particle content. The triggering sampler preferably sends a signal (either directly to detecting sampler 920, or to detecting sampler 920 via control 936) if a particle count threshold, or a biological particle count threshold, is reached. While it would be possible not to employ a threshold level so that the detecting sampler is triggered by any particle count, such an embodiment would likely result in too many false positives. However, this more aggressive embodiment may be acceptable if identification unit 924 is included, and if mail sampling system does not stop or sound an alarm until identification unit 924 determines that a specific threat is present.

Figure 4B:
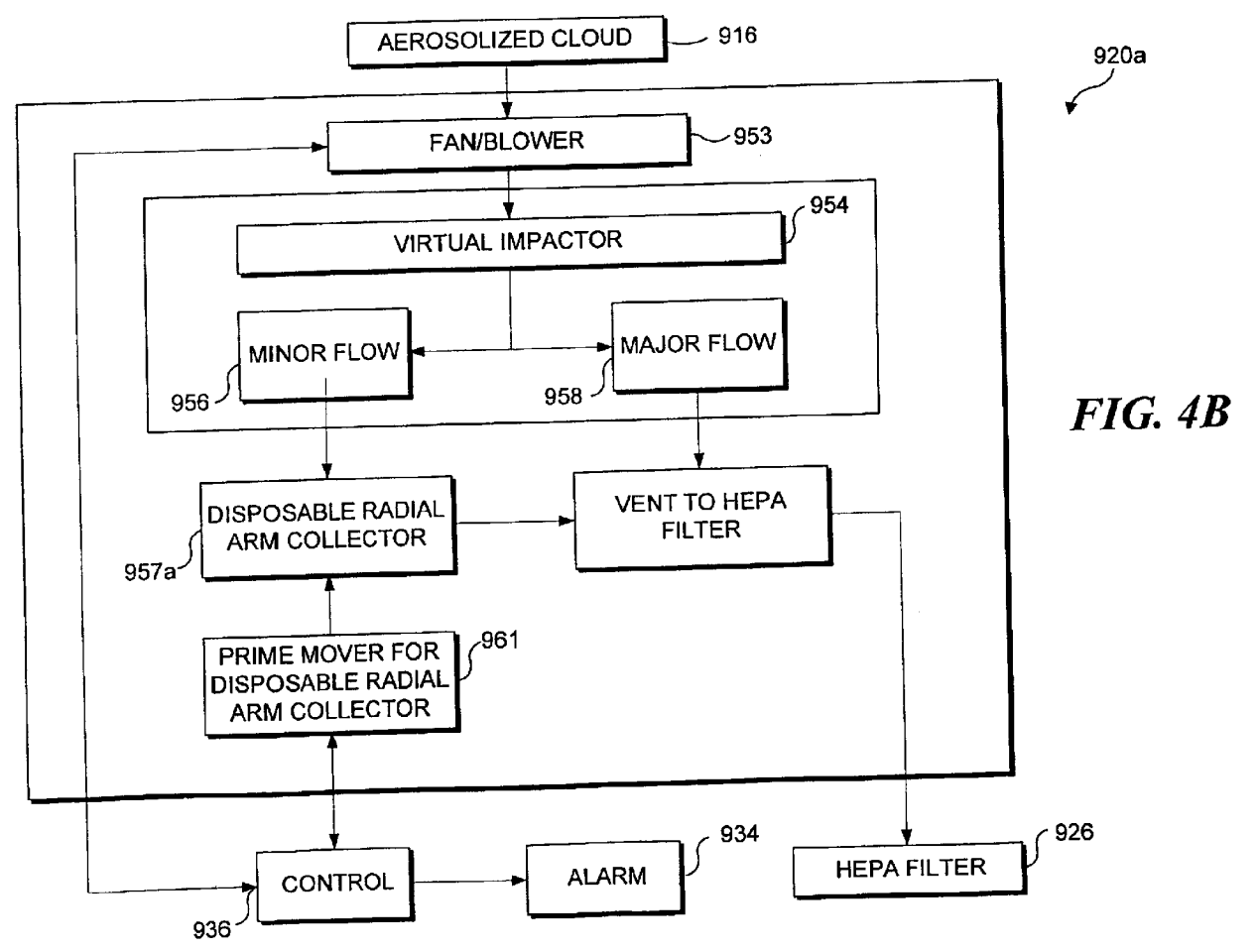

FIG. 4A illustrates a first embodiment of a detecting sampler in which the rotating arm collector is a non-disposable component. FIG. 4B, which is discussed in detail below, illustrates a second embodiment of a detecting sampler in which the rotating arm collector is a disposable component. Referring now to FIG. 4A, once the detecting sampler receives an activation signal from the triggering sampler, fan/blower 953 servicing the detecting sampler is energized, and particulate laden air begins to flow through virtual impactor 954. As described above, the major flow is directed to HEPA filter 926, and the minor flow is directed toward radial arm collector 957.

Because a wet sample (i.e., a sample of the particulates collected in a liquid) is likely to be required to identify the particulates, detecting sampler 920 includes radial arm collector 957 and rinse fluid reservoir 959. However, if analytical technology is developed that does not require a wet sample, then radial arm collector 957 and rinse fluid reservoir 959 need not be included. Radial arm collector 957 is energized at the same time fan/blower 953 is. As the minor flow is directed into radial arm collector 957, particulates impact and are deposited on the radial arm. After a defined sampling period elapses, a rinse fluid is directed onto the radial arm, and the deposited particulates are rinsed off and collected with the rinse liquid. It should be understood that there are many possible ways in which radial arm collector 957 and rinse fluid reservoir 959 can be controlled. For example, the rotation of radial arm collector 957 can terminate before the radial arm collector is rinsed, or the radial arm collector can be rinsed during rotation. Furthermore, different types of rinse fluids can be employed, and if desired, a sterilizing rinse can be employed following each time that the detecting sampler is activated to prevent cross contamination of samples. Additives can be added to the rinse fluid, such as detergents (to reduce surface tension, and enhance particulate recovery), or nutrients to maintain a viable environment for any collected biological particles. Such embodiments are discussed in more detail below.

The fluid used to rinse the radial arm collector is collected in a wet sample collector 966. Wet sample collector 966 is preferably a small vial or bottle that is manually removed from mail sampling system 900. However, the collected liquid sample can instead be diverted to identification unit 924 for analysis within mail sampling system 900. Identification unit 924 is generally not capable of identifying more than one specific substance because it is optimized to identify and verify the presence of a specific target material, such as anthrax. Of course, additional identification unit, capable of detecting different target substances could also be included in mail sampling system 900. Detecting sampler 920 would then need to be operated for a sufficient time to generate a sample adequate in volume so that a liquid sample might be provided to each identification unit employed.

It should be noted that triggering sampler 918 could be used to determine the identification unit that should be employed, if more than one identification unit is included. For example, as described above, particle counters are available that can discriminate between biological and non-biological particulates. A mail sampling system could be equipped with a first identification unit adapted to detect anthrax (a biological particulate), and a second identification unit adapted to detect cyanide (a non-biological chemical toxin). If a large number of biological particles are counted by the particle counter, the liquid sample provided by detecting sampler 920 would be diverted to the first identification unit. Conversely, if a small number of biological particles are counted, the liquid sample provided by detecting sampler 920 might be diverted to the second identification unit. Those of ordinary skill in the art will recognize that valves, under the control of control 936, could be used to divert the liquid sample to the appropriate one (or more) of a plurality of different identification units.

As noted above, alarm 934 can be activated each time that the detecting sampler is activated, or only when an identification unit determines that a specific chemical or biological threat is present in a sample that has been collected. As will be described in more detail below, radial arm collector 957 can be coated with different materials to enhance its ability to collect and retain particles.

As noted above with respect to FIG. 4B, in which the radial arm collector is a disposable component, there is no rinse fluid reservoir 959 or wet sample collector 966. In this embodiment, once a sample is collected, the alarm sounds and the disposable radial arm collector is removed from the mail sampling system and replaced with a fresh unit. Once removed, the disposable radial arm collector is rinsed in a rinse station to provide a wet sample for analysis. This embodiment is described in greater detail below.

Radial Arm Collector Technology

A radial arm collector is an optional component of the triggering sampler, and a preferred component of the detecting sampler. The structure and operation of radial arm collectors are described below. In order to remove impacted particles from the surface of a radial arm collector, rinse fluid is periodically introduced. Particles become entrained in the rinse fluid, which can then be analyzed.

Figure 13:
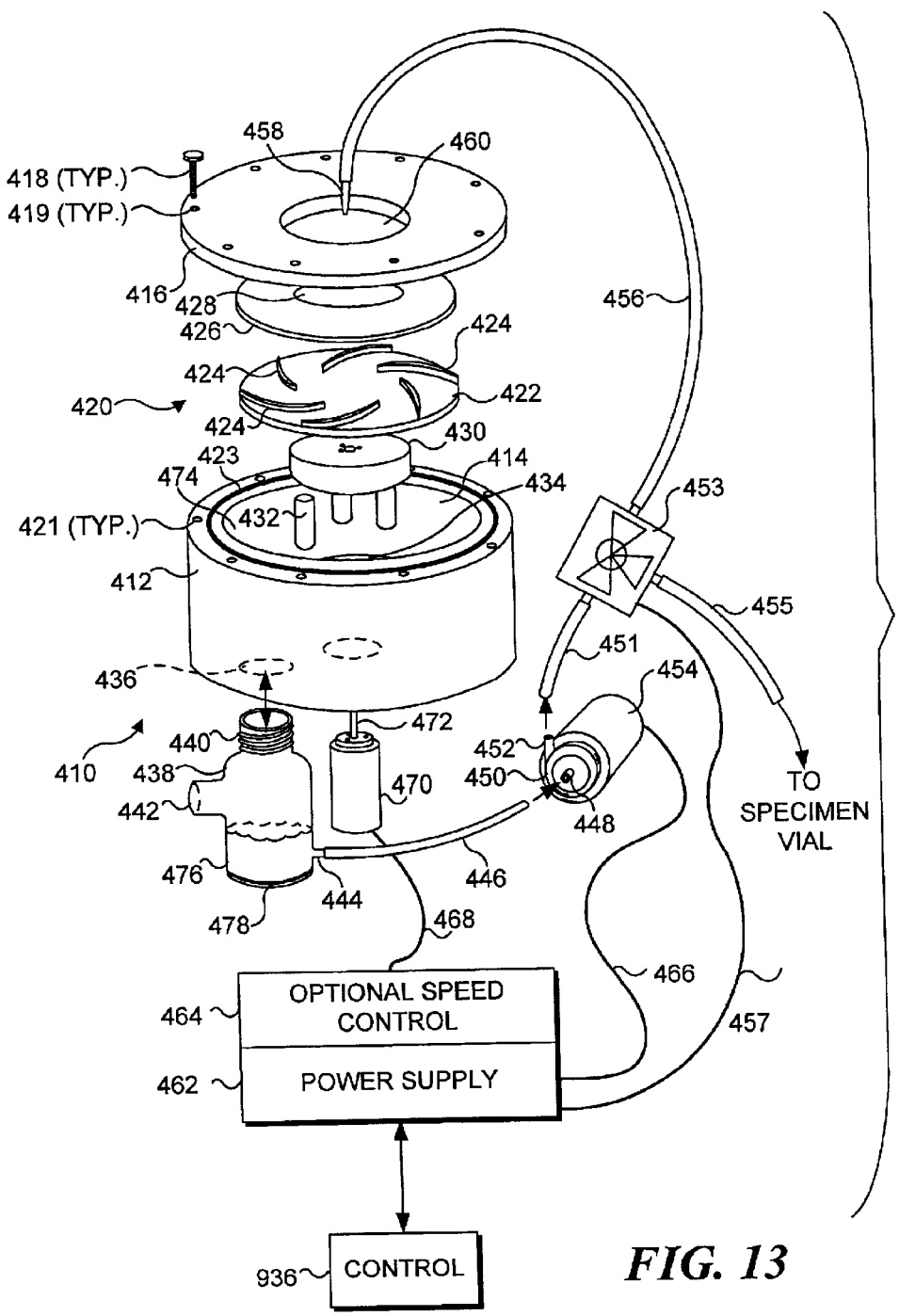
FIG. 13 is an exploded isometric view of a first embodiment of a particle impactor in accord with the present invention.
Figure 14:
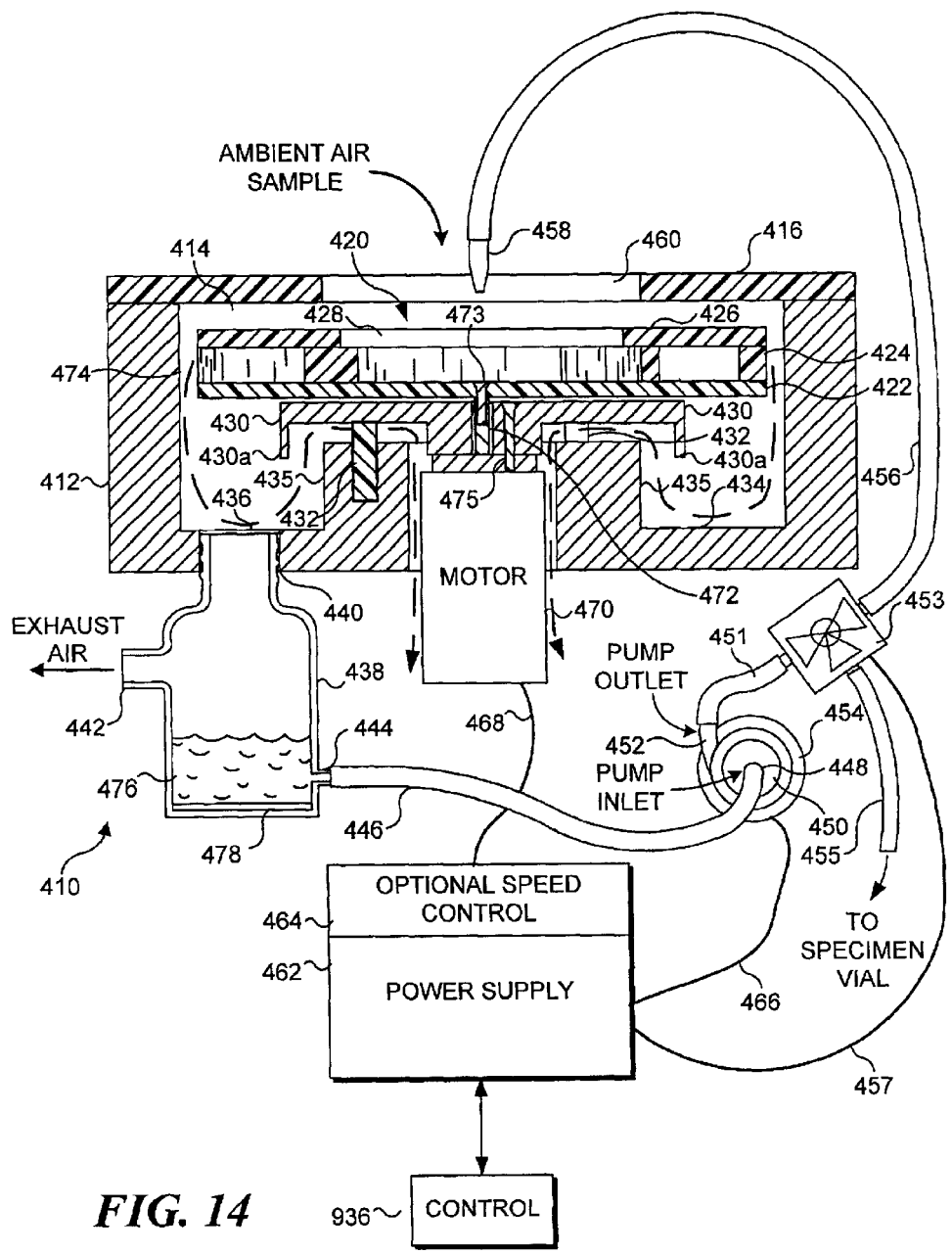
FIG. 14 is a cross-sectional elevational view of the first embodiment the particle impactor shown in FIG. 13.

A first embodiment of a radial arm collector comprising a particle impactor 410 is illustrated in FIGS. 13 and 14. Particle impactor 410 includes a cylindrical shaped housing 412 formed from a metal, or alternatively, molded or otherwise formed from a relatively lightweight polymer material. Housing 412 defines an internal cylindrical cavity 414. Cavity 414 is covered with a plate 416 that is held in place by a plurality of threaded fasteners 418, which pass through orifices 419 in plate 416 and are then threaded into blind threaded openings 421. Openings 421 are spaced apart around the top surface of the underlying cylindrical portion of housing 412. An O-ring 423 is seated in this top surface adjacent to blind threaded openings 421 and provides a seal against the under surface of plate 416.

A combined impact collector and fan 420 is rotatably mounted within cavity 414. Combined impact collector and fan 420 includes a round plate 422 on which are formed a plurality of impeller vanes 424, spaced apart around the top surface of plate 422 and disposed at an angle so as to serve both as a centrifugal fan that moves air into cavity 414 from an external ambient environment surrounding impact collector 410, and as an impactor on which particulates are separated from the air drawn into the cavity. Impeller vanes 424 are thus curved, so that when plate 422 is rotated, the impeller vanes draw air through an opening 428 formed in an annular plate 426 that is affixed over the top of impeller vanes 424, moving the air in which particulates are entrained from the ambient environment into cavity 414 and collecting the particulates. Specifically, in addition to drawing air (or other gaseous fluid) into cavity 414, impeller vanes 424 also impact against particulates, thus separating the particulates from the air drawn into the cavity by at least temporarily retaining the particulates on the surfaces of the impeller vanes on which the particulates have impacted. Furthermore, particulates are also collected on other surfaces within the cavity on which the particulates impact, including for example, the surfaces of plate 422, annular plate 426, and an inner surface 474 of cavity 414. Clearly, the greater the mass of the particulates, the more likely it will be that they will be separated from air or another gaseous fluid by the impact collector. However, even submicron particulates (including solids or semi-solids) can be separated from a gaseous fluid with the present invention, for the reasons explained below.

It should be pointed out that no additional fan or device is required to cause air or other fluid in which particulates are entrained to move into cavity 414 (though if a virtual impactor is used upstream of the combined impact collector and fan to provide a minor flow with a concentrated amount of particulates, the virtual impactor will require a separate fan). In virtually every other type of impact collector incorporating a rotating arm intended to separate particulates from a gaseous fluid as a result of the impact of the particulates against the rotating surface, a separate fan assembly is required to move the gaseous fluid into the vicinity of the rotating arm assembly. In contrast to such prior art devices, the present device includes combined impact collector and fan 420, which both draws air or other gaseous fluid into the cavity and impacts the particulates to separate them from the air or other gaseous fluid in which they are entrained.

While other types of materials can be used, combined impact collector and fan 420 is preferably fabricated from a plastic material or other type of lightweight, low angular momentum or low inertia materials, to facilitate its rotation. Annular plate 426 is preferably adhesively attached to the tops of impeller vanes 424. Plate 422 is attached to a drive shaft 472 with a threaded fastener 473 that extends down through the center of plate 422 into the end of the drive shaft. A mounting plate 430 rests on the top of a plurality of standoffs 432 and includes an annular skirt 430a that depends downwardly from the perimeter of the mounting plate.

A threaded drain port 436 is provided in a bottom 434 of cavity 414 and is disposed adjacent a periphery of the cavity. During usage of particle impactor 410, a receiver 438 is threaded into threaded drain port 436 and is provided with mating threads 440 around its inlet to facilitate its rapid attachment and removal from housing 412. It is alternatively contemplated that the receiver may be held in place with a quick-release fastener (not shown) or by any other suitable mechanism, including a friction fit using an elastomeric fitting that is disposed around the neck of the receiver. Receiver 438 serves as a reservoir and includes a side arm 442 through which part of the air or other gaseous fluid that flows from cavity 414 is exhausted after the particulates entrained therein have been separated by impact with impeller vanes 424 or other surfaces within the cavity. As will be evident from the dash lines shown extending past each side of a motor 470, most of the air or other gaseous fluid flows between annular skirt 430a and a hub 435 formed in the center of the bottom of the cavity, and then exits the cavity around motor 470, thereby providing cooling for the motor.

An outlet port 444 is included in receiver 438, adjacent its bottom, and is connected through a flexible tube 446 to an inlet 448 of a centrifugal pump 450. As will be apparent from the embodiments discussed below, a peristaltic (or other type) pump may be employed instead of the centrifugal pump shown in FIGS. 13 and 14. It has been contemplated (but not shown in the drawing figures) that a Venturi pump might be fitted into an opening 460 so that the velocity of the air or other gaseous fluid drawn into cavity 414 would create a sufficiently low pressure in a Venturi tube to draw liquid from reservoir 438. This liquid would be injected into the air or gaseous fluid entering the cavity, using much the same method that is used for mixing gasoline with the air entering a cylinder in automotive carburetors. Use of such a Venturi device would enable centrifugal pump 450 to be eliminated, but would also eliminate a three-way valve 453, since the flow of liquid from the reservoir induced by a Venturi effect cannot readily be redirected through a three-way valve.

In the embodiment shown in FIGS. 13 and 14, centrifugal (or other type) pump 450 is driven by a separate motor 454. The centrifugal pump includes an outlet 452 that is connected to a flexible conduit 451. The other end of flexible conduit 451 is connected to three-way valve 453, which is controlled with an electrical signal. A flexible conduit 456 connects one outlet port of three-way valve 453 to a nozzle 458, which is disposed above inlet port 460 in cover plate 416. Liquid flowing from nozzle 458 is directed through inlet port 460 toward opening 428 in the combined impact collector and fan that is mounted within cavity 414. Nozzle 458 creates a stream of a liquid 476 that is contained within the reservoir provided by receiver 438. The liquid forms droplets that are carried by air drawn into opening 428 and these droplets wash over the surfaces of impeller vanes 424 and other surfaces within cavity 414, carrying the particulates that have been temporarily retained thereon away. The particulates are carried by the liquid down inner surface 474 toward bottom 434 of cavity 414.

Another outlet port of three-way valve 453 is connected to a flexible conduit 455, which is directed toward a specimen vial or other specimen collection container (not shown). The three-way valve can be selectively actuated by control 936 (see FIG. 1) to direct liquid flowing from centrifugal pump 450 into either flexible conduit 456 for circulation back into cavity 414, or into flexible conduit 455 for withdrawal of a specimen of the particulates being collected. Further options for recovering a specimen of the particulates collected are discussed below.

In addition to clearing particulates from the surfaces on which they have impacted, the liquid directed into cavity 414 through nozzle 458 also serves to entrain submicron particulates carried by the air or gaseous fluid that is drawn into the cavity in droplets. The entraining droplets have substantially greater mass than the submicron particulates alone and are thus more readily separated from the air or other gaseous fluid by impact against surfaces within cavity 414. These submicron particulates are thereafter carried into receiver 438, as described above.

The liquid carrying the particulates that were previously separated from the air or other gaseous fluid drawn into cavity 414 flows through threaded drain port 436 in bottom 434 of the cavity and into receiver 438. Over time, if the particulates separated from the air are solid or semi-solids and if they are denser than the liquid in the reservoir, a residue 478 of the particulates that have been collected will accumulate in the bottom of receiver 438 as the particulates settle out of the liquid. This residue can be readily removed for analysis or other tests. In other instances, where the particulates entering inlet port 460 is liquid aerosol that is miscible in liquid 476 (i.e., the liquid injected to wash the particulates from the impeller vanes), or is less dense than the liquid in the reservoir, the particulates washed from the impeller vanes will continue to increase in concentration within liquid 476, forming a readily collected specimen of the particulates within the reservoir. When this specimen is analyzed, the chemical composition of the aerosols or materials comprising the particulates can readily be determined. It is also noted that the particulates drawn into the impact collector may comprise bacteria or spores, which are also readily analyzed. A sample of liquid 476, with the particulates contained therein comprising a specimen are readily withdrawn from receiver 438 by actuating three-way valve 453 so that it pumps the specimen from the receiver and empties flexible conduit 446 into a specimen vial through flexible conduit 455.

Once the receiver has been emptied, a sterilant or disinfecting solution such as hydrogen peroxide solution, may be circulated through the impact collector from receiver 438, using centrifugal pump 450. Use of the sterilizing solution would then be followed by several rinses to prepare the impact collector to receive another specimen.

It is contemplated that a small heating element (not shown) may be provided either around, adjacent to, or inside the receiver to ensure that liquid 476 does not freeze. Provision of such a heating element should be necessary only if the device is exposed to an ambient temperature that is below the freezing point of the liquid in the receiver.

To rotate the combined impact collector and fan 420, motor 470 is provided. The motor is connected to mounting plate 430 using a plurality of threaded fasteners 475 (only one of which shown in FIG. 14). As noted above, drive shaft 472 of motor 470 is connected to plate 422 using threaded fastener 473. Although not shown, drive shaft 472 may also include a spline, or a flat surface against which a setscrew can be tightened to ensure that the combined impact collector and fan is rotatably driven by drive shaft 472 when motor 470 is energized.

A power supply 462 of generally conventional design provides electrical current for energizing pump motor 454 and motor 470. Note that other components of mail sampling system 900 also require a power supply. It is contemplated that a single power supply, energized by conventional readily available line power service, will preferably be used to provide all the power requirements for mail sampling system 900, rather than requiring each component, such as the triggering sampler and the detecting sampler, to incorporate an individual power supply. The electrical current supplied to motor 470 is conveyed through a power lead 468.

The position of three-way valve 453 is controlled by control 936, electrical current being supplied to three-way valve 453 via a power lead 457. The electrical current supplied to pump motor 454 is conveyed through a power lead 466. Optionally, a speed control 464 is included to enable control 936 to selectively control the speed of motor 470. In a preferred embodiment, motor 470 is a Micromole Inc. brushless DC motor, Series 1628, although other similar types of motors are equally usable for this purpose. Optional speed control 464 can be used to adjust the rotational speed of motor 470, and thus to enable the rotational speed of the combined impact collector and fan to be set within the range of from about 80 to about 50,000 rpm (or greater if a motor capable of higher speed is used). The specified speed range corresponds to a rate of fluid flow through the impact collector of 80 lpm to 540 lpm. Substantially higher flow rates may be required for specific applications of the flow impactor. Generally, it is preferable to operate the impact collector at a higher rotational speed, since it has been determined that the efficacy of particulate collection improves with increased rotational speed of the combined impact collector and fan. While optional speed control 464 may provide for continuously variable speed within the range of motor 470, it is more likely that a multi-position switch would be provided to select the desired speed, for example, from a low, medium, or high-speed option.

Figure 15:
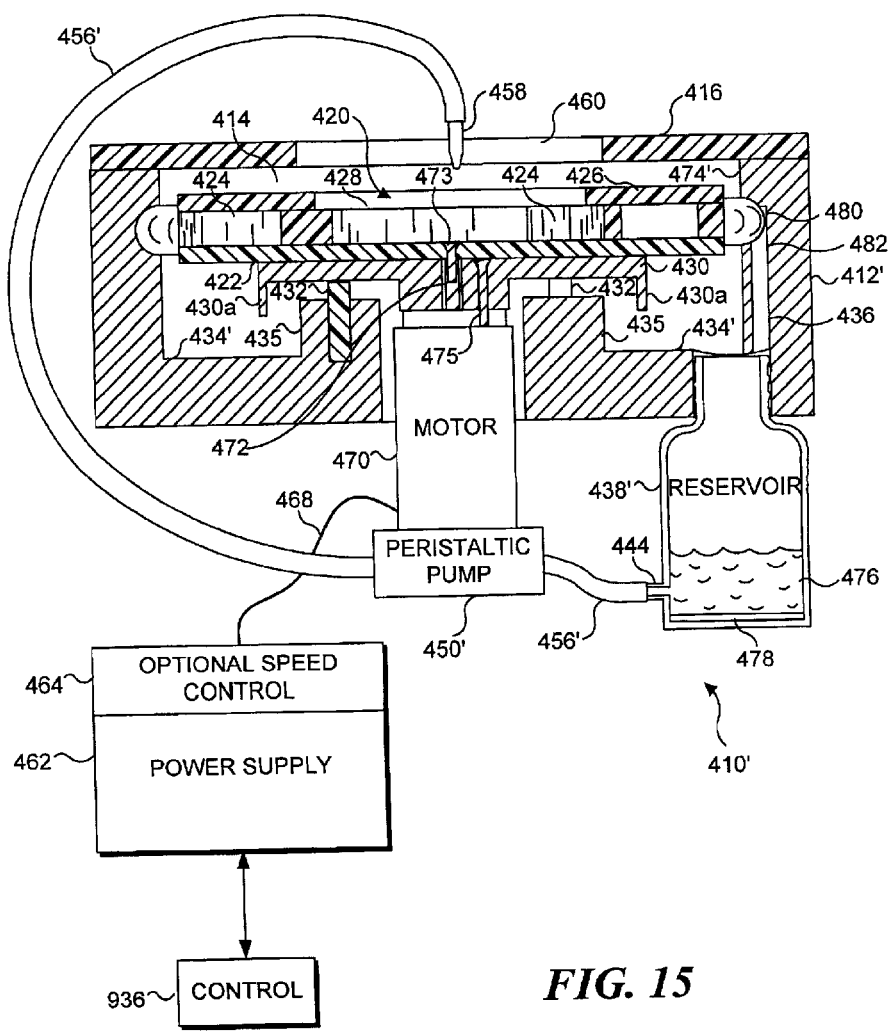
FIG. 15 is a cross-sectional elevational view of a second embodiment of a particle impactor in accord with the present invention.
Figure 16:
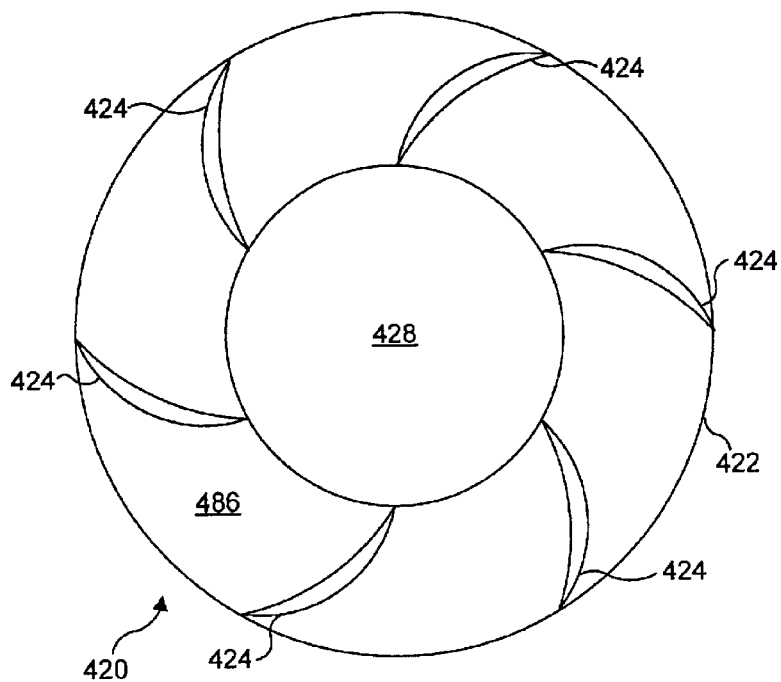
FIG. 16 is a plan view of a combined impact collector and fan used in the present invention.
Figure 17:
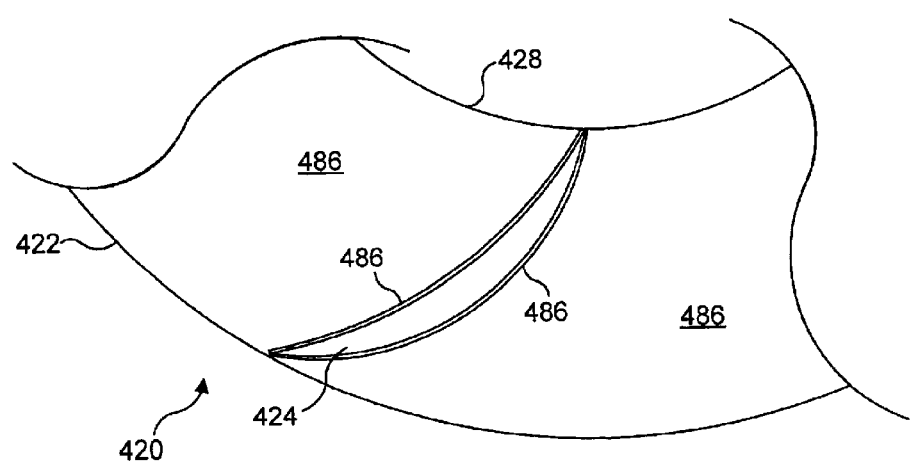
FIG. 17 is a plan view of a portion of the combined impact collector and fan shown in FIG. 16, enlarged sufficiently to illustrate a coating applied to an impeller vane and other surfaces within a cavity of the particles impactor.
Figure 18:
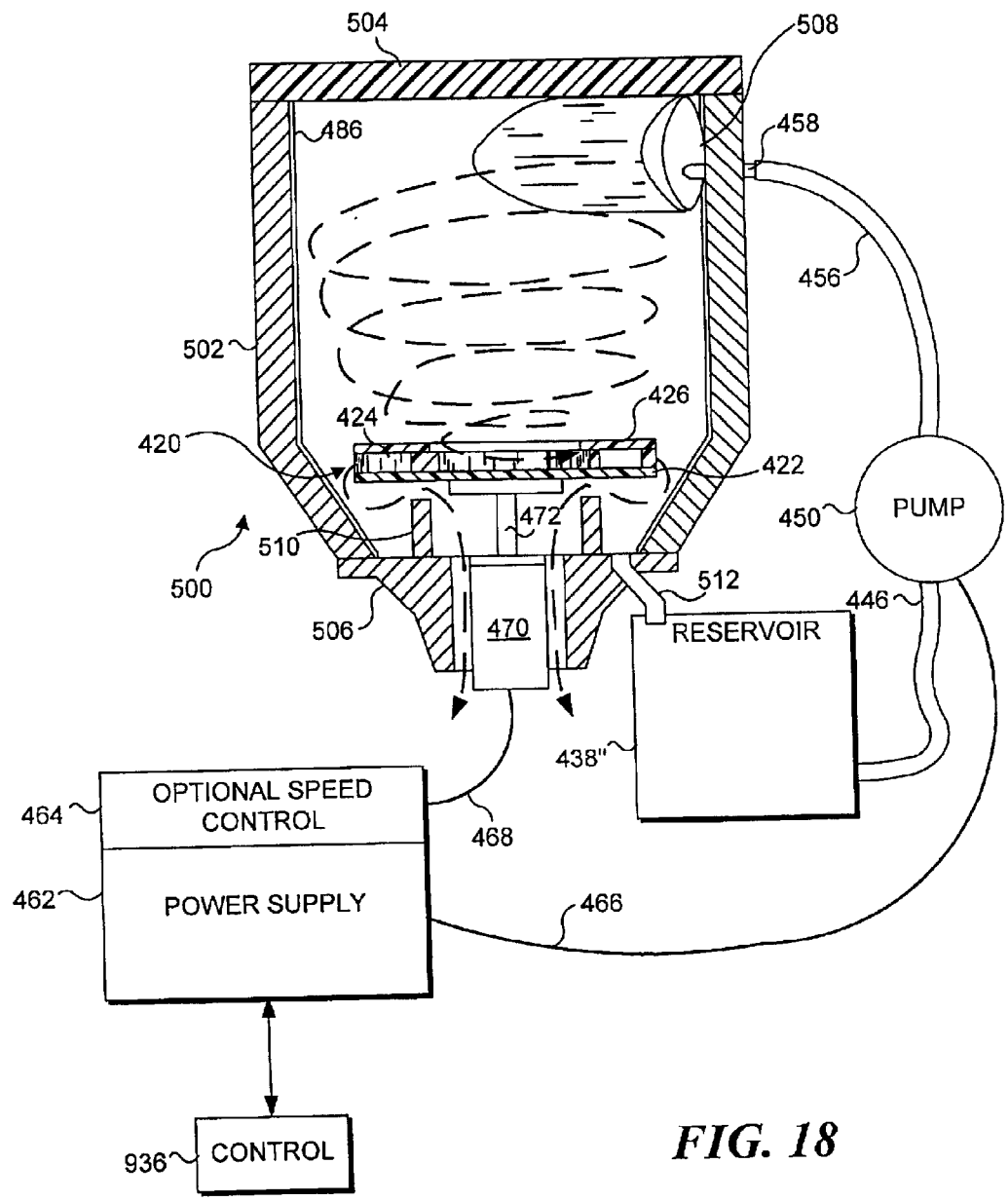
FIG. 18 is a schematic sectional view of another embodiment of a particulate collector used in the present invention, in which a vortex flow of fluid is induced within a cavity.

FIG. 15 illustrates another embodiment of an impact collector 410', which is generally similar in its operation to that of the previous embodiment. Accordingly, identical reference numerals have been used for each of the elements of the embodiment shown in FIG. 15, except where slight differences exist in the configuration or manner of operation discussed above in connection with the previous embodiment. Impact collector 410' includes a housing 412' in which an annular groove 480 is formed around an inner surface 474' of the cavity defined by the housing, immediately adjacent the peripheral edge of combined impact collector and fan 420. At spaced-apart intervals around annular groove 480, vertical passages 482 are provided for conveying liquid carrying particulates washed from impeller vanes 424 downwardly toward a bottom 434' of cavity 414. Bottom 434' includes a depression around its peripheral extent, thereby encouraging the liquid that is carrying the particulates washed from the combined impact collector and fan to flow into a receiver 438', which does not include side arm 442, as was the case with receiver 438 in FIGS. 13 and 14. In the embodiment shown in FIG. 15, all of the air or other gaseous fluid exhausted from cavity 414 flows out around motor 470.

A further difference between these embodiments is that motor 470 also provides the rotational driving force for a peristaltic pump 450' that is coupled to the lower end of the motor. Peristaltic pump 450' draws liquid from the reservoir within receiver 438 and recirculates it through flexible conduit 456 back into cavity 414. By avoiding the need for a separate pump motor for peristaltic pump 450', a relatively lower cost and a more compact configuration is achieved for impact collector 410', compared to impact collector 410. Also, peristaltic pump 450' can be reversed by reversing the direction of rotation of motor 470, so that all of the liquid within flexible conduit 456' can be returned into reservoir 438' before the specimen of particulates collected with the liquid in the reservoir is removed for analysis or other study.

Further details of the combined impact collector and fan are illustrated in FIGS. 16 and 17. As shown in FIG. 17, a coating 486 has been applied to the exposed surfaces of each impeller vane 424 and of plate 422. In addition, coating 486 is preferably applied to all exposed surfaces within the cavity of the impact collector—in all of the embodiments disclosed herein. Two types of coatings 486 are contemplated. The first type of coating is identified as a substance called TETRAGLYME. This substance is hydrophilic until it is exposed to water and when dry, is relatively very sticky, tending to readily retain particulates that impact the surfaces of impeller vanes 424 that are coated with the substance. However, once water is sprayed into opening 428 and wets the TETRAGLYME coating, it becomes hydrophobic, is no longer sticky or tacky, and in fact, readily releases the particulates that previously were retained by it. The water washes the particulates from coating 486 and carries the particulates down into receiver 438, as described above.

A second type of material being considered for coating 486 is PARYLENE, which is a tetrafluoromore manufactured and sold by Dupont Chemical Company under the trademark INSUL-COTE™, Type N, and is characterized by a relatively low coefficient of friction causing it to be extremely slippery and not sticky. Accordingly, particulates impacting against coating 486 comprising PARYLENE are separated from the gaseous fluid in which they are carried and are immediately washed away by water or other liquid injected through opening 428. It is expected that further empirical testing will determine which of these two coatings provides the maximum efficacy for separating particulates from air or other gaseous fluid entering inlet port 460 using combined impact collector and fan 420.

During operation of the rotating arm impact collector, it is contemplated that either of two modes may be employed for circulating liquid from receiver 438 into cavity 414. In a first mode, liquid from the reservoir within receiver 438 is continuously circulated during rotation of the combined impact collector and fan. Impact collector 410' is particularly adapted to employ this mode of operation, since motor 470 rotates both the combined impact collector and fan, and peristaltic pump 450' (see FIG. 15). In the second mode, liquid is periodically injected into cavity 414 after particulates have collected on the surface of impeller vanes 424 and on the other surfaces within cavity 414 to which coating 486 is applied; the liquid washes the particulates from the impeller vanes and other surfaces, such as the inner wall of the cavity. Impact collector 410 is better adapted to employ this mode of operation, since pump motor 454 and motor 470 can be separately controlled. Furthermore, it is apparent that coating made from TETRAGLYME is preferable for use in connection with the second mode of operation, since the coating needs to dry out to become sticky and better retain particulates that have impacted the coating on the rotating impeller vanes. After being thus separated from the air or other gaseous fluid, the particulates should then be washed from the coating, which when wetted by water, readily release the particulates so that they flow with the water into the reservoir.

Another embodiment of an impact collector is shown in a schematic representation in FIG. 18. An impact collector 500 includes an upper housing 502, formed in a shape that encourages a vortex to be created in the air or other gaseous fluid entering the cavity of the housing. A cover 504 closes one open end of the upper housing, and a lower housing 506 is sealingly attached to the lower depending end of upper housing 502.

Adjacent cover 504 is formed a tangential opening 508 through upper housing 502. Air or other gaseous fluid is drawn into the cavity of impact collector 500 through this tangential opening by rotation of combined impact collector and fan 420, which is mounted on drive shaft 472 of motor 470. As in the previous embodiments, rotation of drive shaft 472 causes combined impact collector and fan 420 to rotate, which draws the air or other gaseous fluid into the cavity of the upper housing. However, this embodiment provides a much greater wetted surface area on the inner surface of upper housing 502 against which particulates impact as the gaseous fluid rotates in a vortex. The inner surface of the upper housing and other surfaces within the cavity are coated with coating 486 to promote the separation and collection of particulates from the air or gaseous fluid, generally as discussed above. Particulates also impact on vanes 424 of the combined impact collector and fan and are retained there until washed away by liquid pumped from a reservoir 438" by pump 450. A dam 510 tends to retain the liquid carrying the particulates that have been washed from the surfaces so that the liquid flows into reservoir 438" through a conduit 512. While not illustrated in this embodiment, it will be apparent that the three-way valve can also be used to facilitate taking a specimen from the liquid in reservoir 438". Air or other gaseous fluid exhausts from the interior of impact collector 500 past motor 470, as indicated by the dash arrows.

Figure 19:
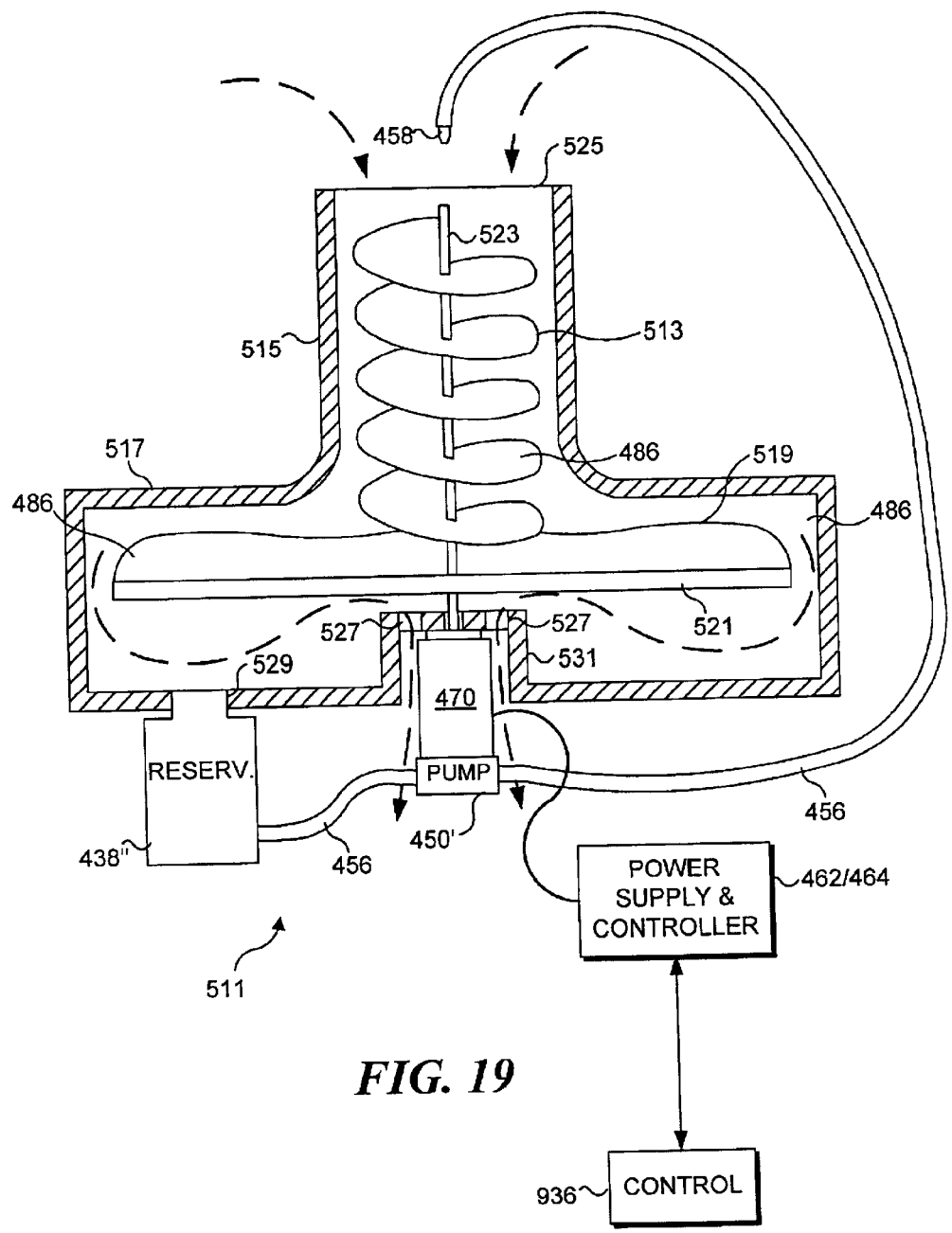
FIG. 19 is a schematic cut-away view of yet another embodiment of a particulate collector in which a combined helical vane impact collector and an impeller are included.

Yet another embodiment of an impact collector is illustrated in FIG. 19. This embodiment is also represented in a schematic manner and is included to provide yet another example of a different configuration for the combined impact collector and fan. In an impact collector 511, a helical vane portion 513 of the combined impact collector and fan extends upwardly within a housing throat 515. The housing throat has a substantially smaller diameter than a lower housing 517 in which a plurality of impeller vanes 519 are disposed. The impeller vanes are mounted on a round plate 521, which is rotatably driven by a drive shaft 523 of motor 470. Air or other gaseous fluid in which particulates are entrained enters through an opening 525 at the top of housing throat 515, drawn by the rotation of helical vanes 513 and impeller vanes 519. The particulates impacting upon the surfaces of these vanes and on the interior surfaces of the throat housing and the lower housing are separated from air or other gaseous fluid. This air or other gaseous fluid exhausts through ports 527 and flows past motor 470, cooling it.

As in the embodiment of FIG. 15, motor 470 drives a peristaltic (or other type) pump 450', which circulates water or other liquid from reservoir 438" through flexible conduit 456 and into opening 525 through nozzle 458. The liquid washes the particulates from coating 486, which covers the surfaces of the helical vanes and impeller vanes and other surfaces, including the inner surfaces of housing throat 515 and lower housing 517. The liquid carrying the particulates washed from these surfaces flows into reservoir 438" through an opening 529 formed in the bottom of lower housing 517. A hub 531 around motor 470 prevents the liquid inside the cavity from flowing through ports 527 with the air or other gaseous fluid.

Impact Collector Coating Technology

Figure 20:
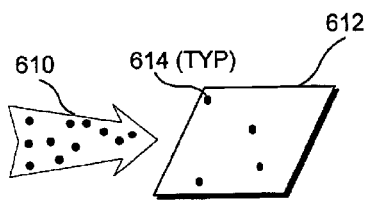
FIG. 20 (Prior Art) is a schematic view of a fluid in which particulates are entrained, impacting an uncoated impact collection surface.
Figure 21:
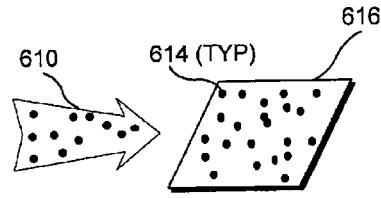
FIG. 21 is a schematic view of a fluid in which particulates are entrained, impacting a coated impact collection surface in accord with the present invention.

FIGS. 20 and 21 schematically illustrate how coating an impact collection surface with a material can substantially enhance the efficiency of that surface. FIG. 20 shows a fluid 610 in which particulates 614 are entrained, moving relative to a (prior art) impact collection surface 612 that is not coated. Particulates 614 are separated from the fluid by striking against impact collection surface 612. FIG. 21 shows fluid 610 moving toward a coated impact collection surface 616, which has been coated with a material that retains substantially more of the particulates entrained in fluid 610. By comparing FIGS. 20 and 21 it will be apparent that significantly more particulates 614 are collected on coated impact collection surface 616 than on impact collection surface 612.

The relatively greater density of particulates 614 evident on coated impact collection surface 616 compared to impact collection surface 612 is due to a characteristic of the coating to better retain particulates and thus more efficiently separate the particulates from the fluid in which they are entrained, compared to the prior art impact collection surface that is not coated. In this first embodiment of the present invention shown in FIG. 21, the geometry of impact collection surface 616 is generally irrelevant. The coating of the present invention can be applied to the impact collection surfaces in virtually any impact collector. Simply by coating the impact collection surfaces of an impact collector with one of the materials described below, a substantial increase in the efficiency with which particulates are separated from a fluid and collected is achieved.

Figure 22:
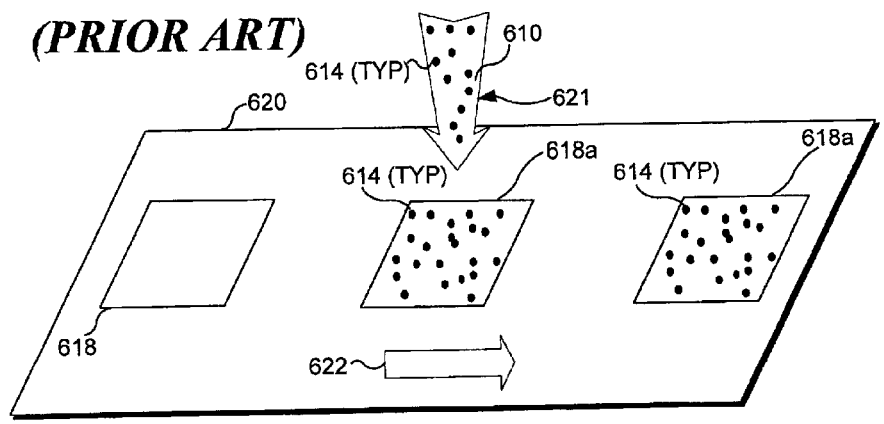
FIG. 22 is a schematic view of a flexible tape having a coated impact collection surface.

FIG. 22 schematically illustrates how such a coating can be incorporated onto a collection surface. While a preferred embodiment employs a rotating arm collector, as opposed to the tape reel collector of FIG. 22, those of ordinary skill will realize that the coating shown in FIG. 22 could also be incorporated into a rotating arm collector as described above. In FIG. 22, a plurality of coated areas 618 are applied to an upper exposed surface of an elongate tape 620. As illustrated in this figure, tape 620 is advanced from left to right, i.e., in the direction indicated by an arrow 622. Tape 620 thus moves past a stream 621 of fluid 610 in which particulates 614 are entrained. Stream 621 is directed toward the upper surface of the tape. As the tape advances, fresh-coated areas 618 are exposed to impact by particulates 614. The particulates that impact on these coated areas are at least initially retained thereon, as shown in coated areas 618*a*. In the embodiment illustrated in FIG. 22, coated areas 618 and 618*a* are not contiguous; but instead are discrete patches disposed in spaced-apart array along the longitudinal axis of tape 620. Various types of material described below can be used to produce coated areas 618.

Figure 23:
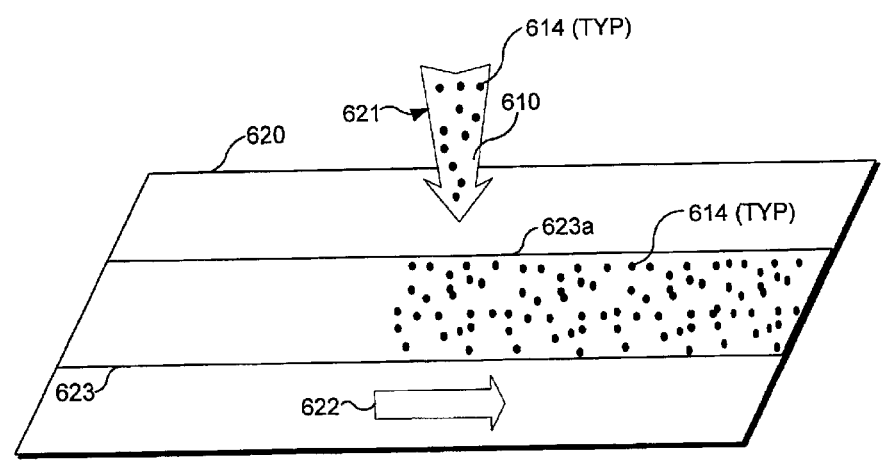
FIG. 23 is a schematic view of a flexible tape having a coated impact collection surface and advanced past a collection point by a rotating take-up reel.

In an alternative embodiment shown in FIG. 23, a continuous coated impact collection surface 623 extends longitudinally along the center of a tape 620'. As tape 620' advances in the direction indicated by arrow 622, stream 621 of fluid 610 with entrained particulates 614 is directed toward the upper surface of the tape. Particulates 614 are retained by the coating, as shown in a coated impact collection surface 623*a*. As tape 620' advances in direction 622, coated impact collection surface 623 is exposed to impact by particulates 614 carried in stream 621. In the embodiment that is illustrated, the coating does not cover the entire upper surface of tape 620'. However, it should be understood that any portion or the entire upper surface of tape 620' could be covered with the coating. The various types of material contemplated for the coating are discussed below.

Figure 24:
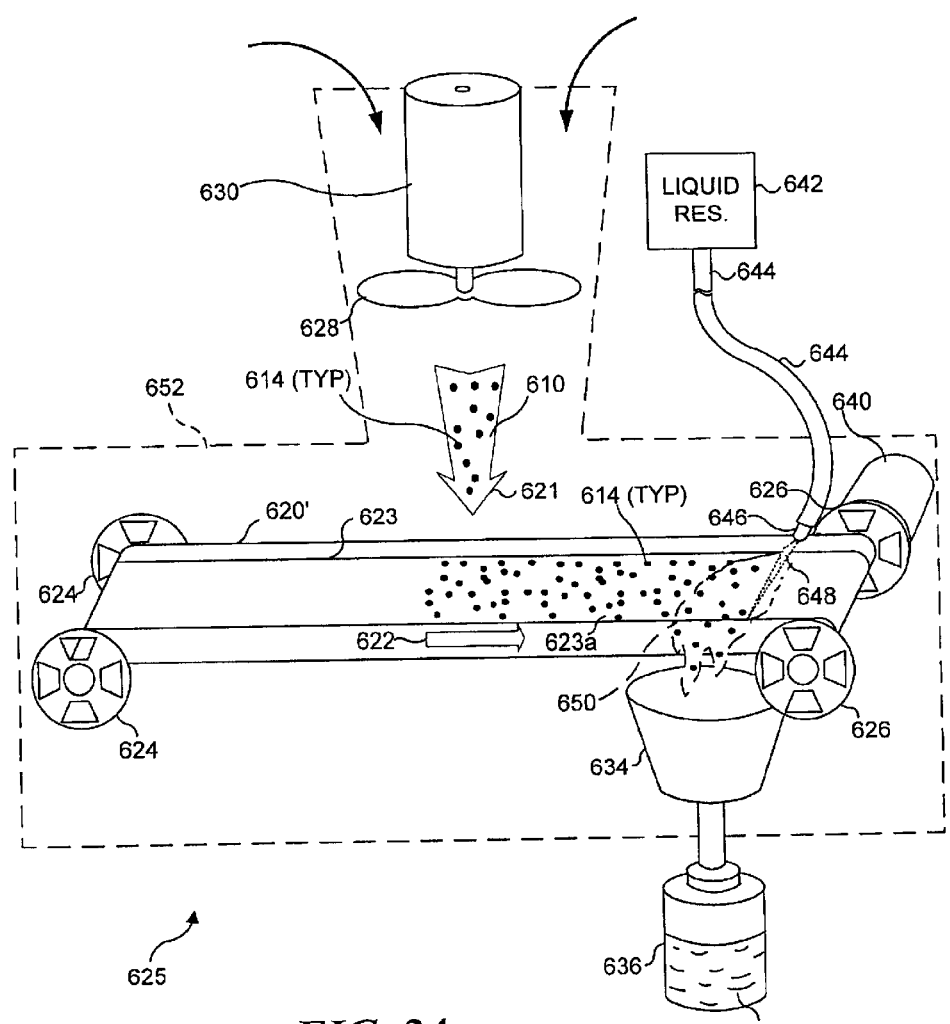
FIG. 24 is a schematic view of a particle impact collector using a flexible tape having a coated impact collection surface.
Figure 25:
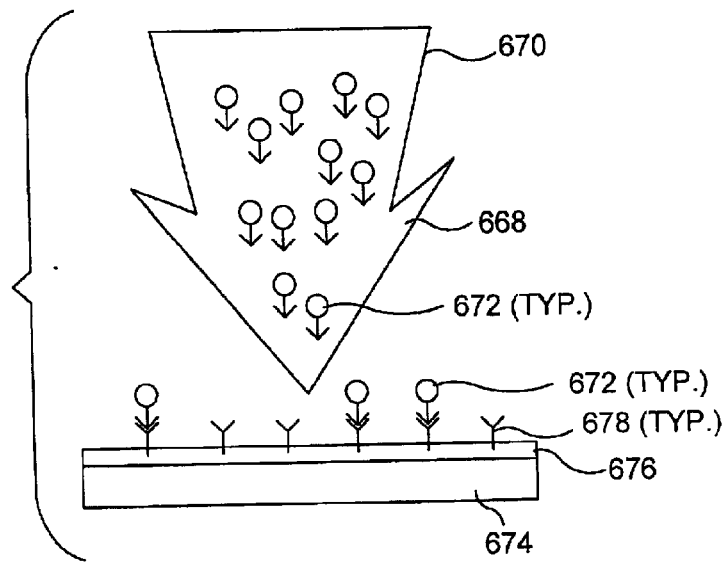
FIG. 25 is a schematic illustration illustrating an impact collection surface coated with a material that includes antibodies selected to link with an antigen on a specific biological particulate.
Figure 26A:
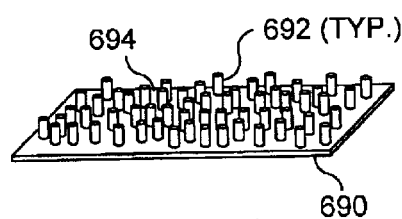
FIGS. 26A and 26B illustrate two embodiments in which outwardly projecting structures are provided on an impact collection surface to enhance particulate collection.
Figure 26B:
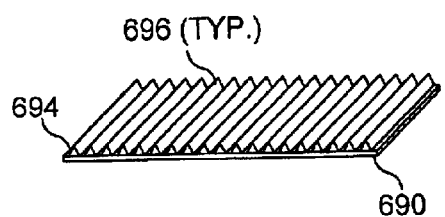

FIG. 24 schematically illustrates a particle impact collector 625 that includes tape 620' with coated impact collection surface 623. Other elements of the collector include a fan 628, which is rotatably driven by an electric motor 630. Fan 628 impels fluid 610 in stream 621 toward coated impact collection surface 623. A housing 652 is optional. Other types of fans or impellers can alternatively be used. For example, a centrifugal fan (not shown) can be employed to move the fluid. If the fluid in which the particulates are entrained were a liquid, a pump (not shown) would be used instead of fan 628 to move fluid 610 toward coated impact collection surface 623. The tape 620' advances from a supply reel 624 onto a take-up reel 626. An electric motor 640 coupled to take-up reel 626 rotates the take-up reel at a selected speed so that the tape passes under stream 621 of fluid 610. Particulates 614 impact on the coated impact collection surface of the tape and are carried toward the take-up reel by the moving tape.

To collect a concentrated sample of particulates 614 from those retained on coated impact collection surface 623*a*, particle impact collector 621 may include a specimen container 636 that is coupled with a funnel 634. A liquid 638 that is rich in the particulates previously retained on the coated impact collection surface partially fills specimen container 636. Liquid 638 is obtained by washing the particulates from the tape. A reservoir 642 is included to supply the liquid for this purpose. The liquid from the reservoir is conveyed through a fluid line 644 and sprayed toward tape 610 through a nozzle 646, which creates a fan-shaped spray 648. If necessary, a pump, e.g., a centrifugal or a peristaltic pump (not shown) may be used to force the liquid through nozzle 646 under sufficient pressure to wash away the particulates retained by the coated impact collection surface. These particulates are carried by a stream 650 of the liquid into funnel 634 and thus, into specimen container 636.

The material used for producing coated impact collection surface 623 and other coated areas or surfaces employed in this description for collecting particulates in accord with the present invention is selected because of certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in particle impact collector 621, TETRAGLYME, as noted above, can be used for the coating. TETRAGLYME is hydrophilic until it is exposed to water and when dry, it is relatively sticky, tending to readily retain particulates that impact upon surfaces coated with it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface, as described above. TETRAGLYME, which is available from chemical supply houses, is bis(2-[methoxyethoxy] ethyl) ether tetraethylene glycol dimethyl ether dimethoxy tetraethylene glycol and has the formula: $CH_3OCH_2(CH_2OCH_2)_3CH_2OCH_3CH_3—O—CH_2—CH_2—O—CH_2—CH_2—O—CH_2—CH_2—O—CH_2—CH_2—O—CH_3$. Tests have shown that TETRAGLYME coating can collect more than three times as many particulates as an uncoated surface. Water molecules are retained by the molecule by links to the oxygen atoms, as shown below.

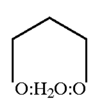

A second type of material usable for the coated impact collection surface is PARYLENE, which is a tetrafluoromore manufactured and sold by Dupont Chemical Company under the trademark INSUL-COTE™, Type N. The PARYLENE material is characterized by a relatively low coefficient of friction, causing it to be extremely slippery and not sticky. Accordingly, particulates impacting against a coated surface comprising PARYLENE are initially separated from the fluid in which they are carried by the impact with the coated surface and are initially retained by the coated surface. However, these particulates are readily washed away from the PARYLENE coated surface by water or other liquid sprayed onto the coating. It will be apparent that PARYLENE is also usable as a coating for the coated impact collection surface in particle impact collector 621. The particulates retained by a PARYLENE coated surface on tape 620' are readily washed away from the coating by water or other liquid comprising spray 648.

The TETRAGLYME material is an example of a class of materials that have two distinct states related to particulate collection. When dry and hydrophilic, the TETRAGLYME material is in a first state, in which it is sticky or tacky and is very efficient at separating particulates from the fluid in which they are entrained, compared to an uncoated surface. However, when wetted, the TETRAGLYME material changes to its second state, in which it readily releases the particulates.

As shown in FIG. 25, a mono-layer material 676 can be applied to a surface 674 of a particle impact collector of other device, to separate specific biological particulates 672 from a fluid 668 such as air or a liquid in which they are entrained. A stream 670 of the biological particulates is directed at material 676, so that the biological particulates impact thereon. Mono-layer material 676 comprises a plurality of antibodies 678 that are selected to link with the antigens on biological particulates 672. Thus, for example, if biological particulates 672 comprise anthrax spores, and antibodies 678 are selected that are specific to anthrax spores, the anthrax spores will be readily separated and retained by linking with the antibodies on the coating. These anthrax spores may then be identified based upon analyses that are outside the scope of this disclosure.

It is also contemplated that the coated impact collection surface need not be planar. Indeed, it is likely that an enhanced particulate collection efficiency can be achieved by using a non-planar coated surface to collect particulates. FIG. 26A illustrates an enlarged view of a portion of one preferred embodiment for an impact collection surface 690 having a plurality of outwardly projecting rods 692 distributed thereon. The outwardly projecting rods increase the surface area of impact collection surface 690, which is provided with a coating 694 of one of the coating materials discussed above, and also increase the "roughness" of the surface to further enhance the collection efficiency of the coating. Coating 694 may be applied over rods 692 or applied before the rods are attached or formed on the impact collection surface. Alternatively, other projecting structures such as ribs 696 may be employed on impact collection surface 690, as shown in FIG. 26B.

Disposable Radial Arm Collectors and Rinsing Stations

The following section provides details of a disposable radial arm impact collector, and a rinsing station used to obtain a wet sample from the disposable radial arm impact collector. Such a disposable radial arm impact collector can be incorporated into the detecting sampler described above. In such an embodiment, once the triggering sampler determines that the detecting sampler should be activated, the disposable radial arm impact collector is energized and employed to collect a sample. The disposable radial arm impact collector is then preferably removed from the mail sampling system unit, rinsed in a rinsing station, and the sample collected is analyzed to determine the type of particles that has been collected.

Referring now to FIG. 4B, once a detecting sampler 920*a* receives a signal from the triggering sampler, fan/blower 953 servicing the detecting sampler is energized, and particulate laden air begins to flow through virtual impactor 954. As above, the major flow 958 is directed to HEPA filter 926, and the minor flow 986 is directed toward disposable rotating arm collector 957*a*, which is rotated by a prime mover 961. As will be described in greater detail below, prime mover 961 is preferably drivingly coupled to disposable rotating arm collector 957*a* via a magnetic coupling, that facilitates easy replacement of a spent disposable rotating arm collector with a fresh unit.

Generally, prime mover 961 will be energized at the same time fan/blower 953 is, to rotate disposable rotating arm collector 957*a* as the minor flow is directed into the disposable radial arm collector. Particulates impact on the radial arm, and a significant number of the impacted particulates are deposited on the radial arm. After a defined sampling period elapses, prime mover 961 will be deenergized, and alarm 934 will sound to notify an operator that disposable rotating arm collector 957*a* is to be removed for analysis. As discussed above, disposable rotating arm collector 957a can be coated with different materials to enhance the radial arm collector's ability to collect particles. Also as discussed above, prime mover 961 will preferably be energized by conventional line power servicing mail sampling system 900, or from a suitable power supply that is energized with line power.

The following description discusses a disposable radial arm impact collector as a component of a personal air-monitoring unit. However, it should be understood that disposable radial arm impact collector described below (referred to as a disposable sample collection cartridge) could be readily incorporated into the detecting sampler described above, as long as a suitable (nondisposable) prime mover is provided. Of course, the battery portion of the personal air-monitoring unit would not be required when incorporating the disposable radial arm impact collector into mail sampling system 900. Control of the disposable radial arm impact collector would preferably be provided by control 936 (see FIG. 1), so the on/off controls and the control unit described below in conjunction with a personal air-monitoring unit would also not be required. The critical components of the personal air-monitoring unit described below that would preferably be included in an embodiment of the mail sampling system of the present invention that included a disposable radial arm impact collector would be the prime mover and the disposable radial arm impact collector itself (referred to below as a disposable sample collection cartridge). Those critical components are detailed in FIGS. 29A and 29B.

Figure 27:
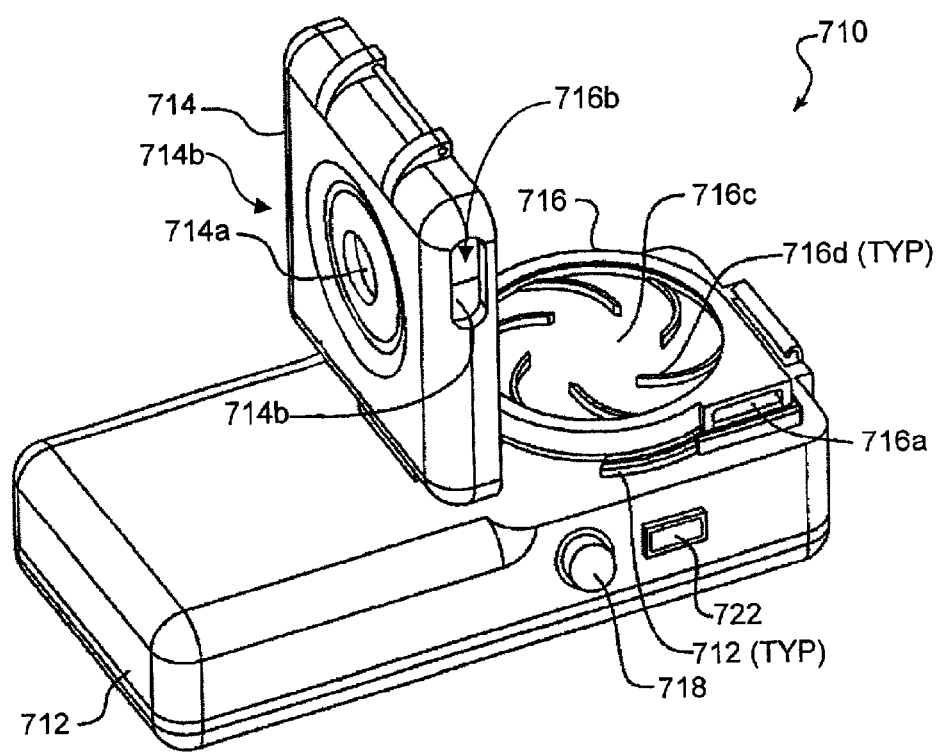
FIG. 27 is an isometric view of a portable sampler in accord with a first embodiment of the present invention.

Personal air-monitoring unit 710 of FIG. 27 includes a primary housing 712, a secondary housing 714, a power switch 718, a battery charge indicator 722, and a disposable sample collection cartridge 716. Note that primary housing 712 includes a plurality of surface features 724 that help to correctly position disposable sample collection cartridge 716 on the primary housing. Secondary housing 714 includes an inlet air port 714a and an outlet air ports 714b. Inlet air port 714a overlies the center of a combined impact collector and fan 716c, while outlet air ports 714b correspond to outlet air ports 716a and 716b (see FIG. 28) on disposable sample collection cartridge 716. Combined impact collector and fan 716c (as configured in this embodiment) rotates in a clockwise direction, as viewed from above, and includes a plurality of arcuate vanes 716d that serve as impellers and provide rotating impact surfaces that collect particulates entrained within the air. Note that the direction of rotation is not critical, and that combined impact collector and fan 716c can also be rotated in a counterclockwise direction. As the combined impact collector fan rotates, typically at speeds in excess of 5,000 RPM, it draws ambient air through inlet air port 714a so that particulates can be separated from the air by impact with the surfaces of arcuate vanes 716d. It should be noted that the orientation of the outlet air ports 716a and 716b directs the exhaust air from which most of the particulates have been removed, to the sides of the unit. When incorporated into the mail sampling system of the present invention, the exhaust is preferably directed to the HEPA filter of the containment chamber. If a virtual impactor is installed upstream of the disposable radial arm impact collector, the minor flow of that virtual impactor is directed to inlet air port 714a.

Figure 28:
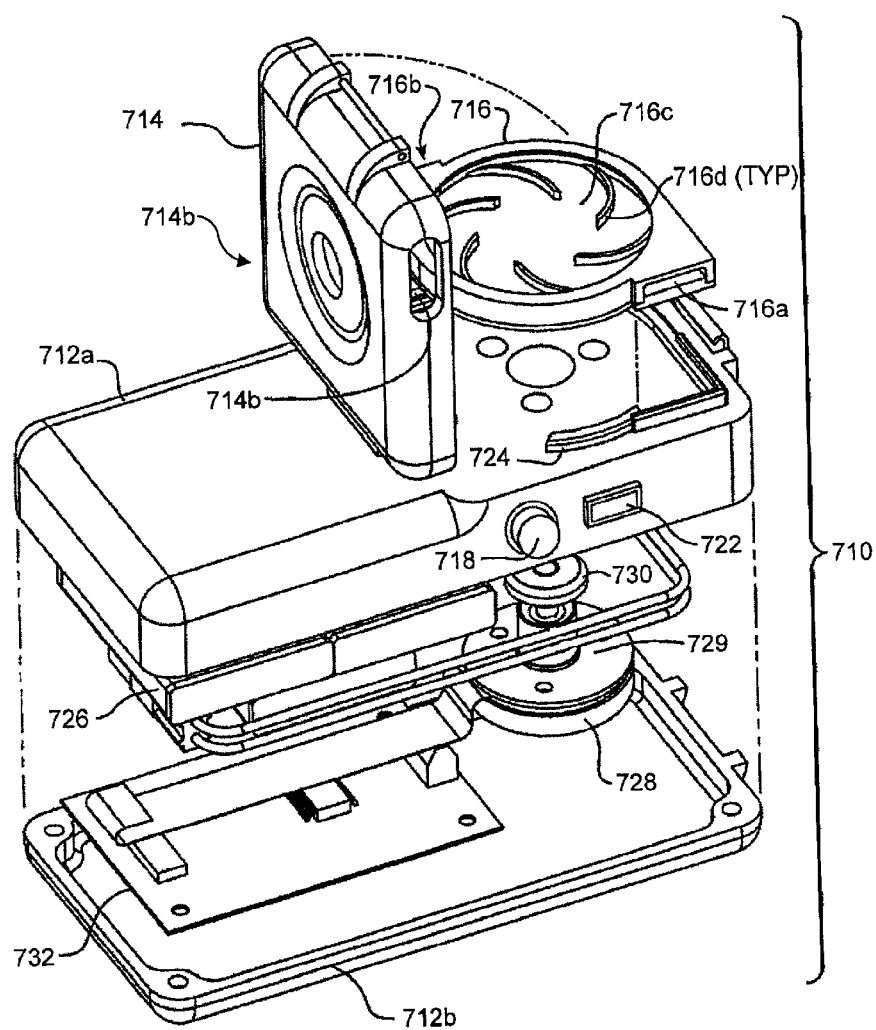
FIG. 28 is an exploded isometric view of the embodiment of FIG. 27.

While personal air-monitoring unit 710 illustrated in FIGS. 27 and 28 was specifically designed to be lightweight and portable, such parameters are less critical for including a disposable radial arm impact collector in a mail sampling system. Thus the battery, power switch 718, and battery charge indicator 722 are not likely to be included in the mail sampling system. A functional prototype of the personal air-monitoring unit has been developed, having an overall size of 4.5"×2.5"×1.3", and the weight of disposable sample collection cartridge 716 being less than 20 grams. For incorporation into the mail sampling system of the present invention, a larger disposable sample collection cartridge 716 may be preferred.

A different disposable sample collection cartridge 716 is needed for each sampling period. The combined impact collector and fan is contained within each disposable sample collection cartridge. It is contemplated that each disposable sample collection cartridge will have a unique identifier (such as a barcode or RF tag (not shown)), which specifically identifies each use. Preferably, once used, the disposable sample collection cartridge will be sealed in sterile packaging until opened for analysis. When the desired collection period has been completed (for example, the disposable radial arm impact collector will function for a predetermined, generally short time when the triggering sampler determines that a sample needs to be obtained for analysis), an operator will retrieve the disposable sample collection cartridge 716 containing the sample, and install a fresh disposable sample collection cartridge 716 into the detecting sampler. The removed disposable sample collection cartridge 716 is then subjected to an analysis to detect biological or chemically hazardous particulates that may have been collected therein.

To facilitate analysis, a liquid sample must be obtained that includes particulates collected on the surfaces of arcuate vanes 716d. Thus, the disposable sample collection cartridge must be rinsed under controlled conditions to provide the liquid sample used in the analysis. The resulting particulate-laden rinse fluid will then be analyzed, and the sample collection cartridge safely discarded. The results, including information from the barcode (lot number, user, etc.) will preferably be displayed, documented, and transferred to a database for archival storage. With insertion of a new disposable cartridge the mail sampling system is ready to collect a new sample. Use of a disposable cartridge has the advantage of avoiding sample cross contamination without the need for decontamination of the cartridge and related components. A disposable cartridge also eliminates concerns of damage or reduced sample collection effectiveness that can be caused by decontamination procedures.

Referring now to the exploded view in FIG. 28, additional details of personal air-monitoring unit 710 are visible. Primary housing 712 includes an upper section 712a and a lower section 712b. These housing sections are preferably removably connected together so that internal components can be changed when required (for example, to replace a malfunctioning electric motor 728). Batteries 726 are not required when disposable radial arm impact collector is incorporated into a mail sampling system. Preferably, electric motor 728 is a brushless, direct current type.

A drive shaft 729 terminates in a magnetic coupler 730. Magnetic coupler 730 is magnetically coupled to a ferromagnetic element (see FIG. 29B) included in combined impact collector and fan 716c. This magnetic coupling enables disposable sample collection cartridge 716 to be readily removed and replaced with a new cartridge, and enables combined impact collector and fan 716c to be drivingly coupled to drive shaft 729.

While an electronic controller 732 and power switch are shown, such elements are not necessary in the mail sampling system. Preferably, control 936 (see FIG. 1) will control electric motor 728. It is contemplated that empirical data will be developed to determine a relationship between specific particulates and an optimal rotational speed for combined impact collector and fan 716c, so that control 936 can be programmed to maintain different optimum speed ranges for a variety of different particulates of interest.

Figure 29A:
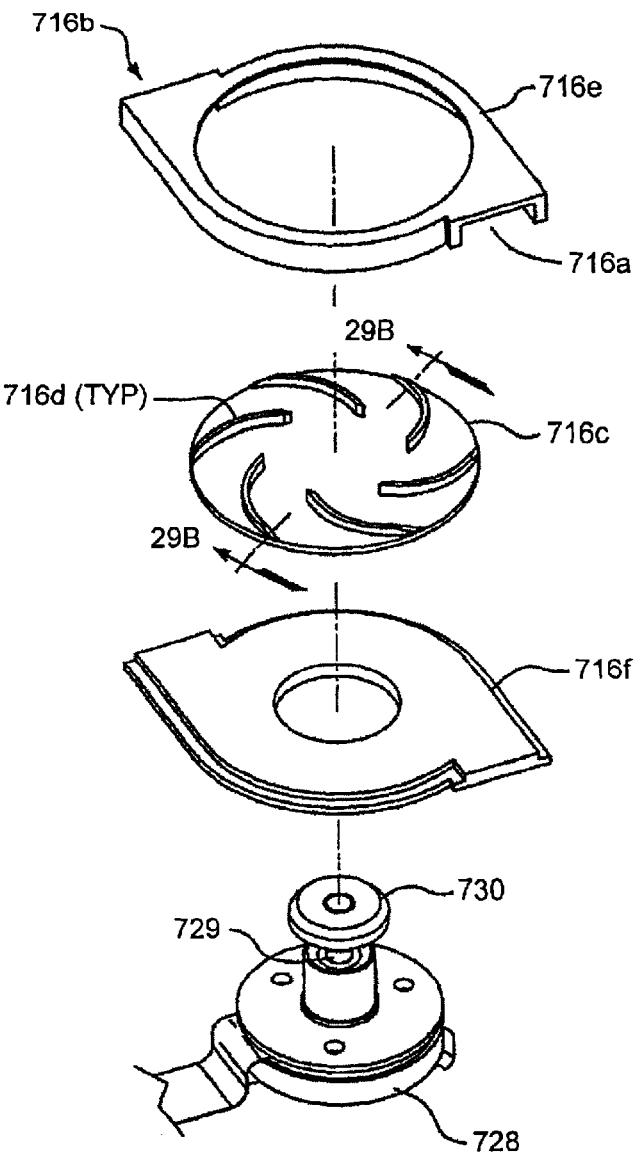
FIG. 29A is an exploded isometric view of a disposable sampling cartridge for use in the embodiment of FIG. 27.

FIG. 29A provides a more detailed view of the components of disposable sample collection cartridge 716 and shows how combined impact collector and fan 716c is coupled to drive shaft 729. Disposable sample collection cartridge 716 comprises an upper shell 716e, a lower shell 716f, and combined impact collector and fan 716c, which is disposed between the upper and lower shells. When assembled, upper shell 716e and lower shell 716f form a fluid passage having outlet air ports 716a and 716b. As combined impact collector and fan 716c is rotated by electric motor 728 (via drive shaft 729 and magnetic coupler 730), particulate-laden air is drawn into the central opening formed in upper shell 716e, so that the particulates entrained in the air impact on and adhere to arcuate vanes 716d, until removed by rinsing.

Figure 29B:
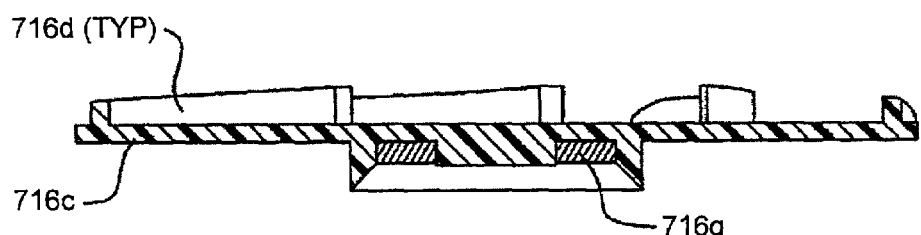
FIG. 29B is a cross-sectional view of a combined impact collector and fan, taken along section line 29B—29B of FIG. 29A.

As shown in FIG. 29B and noted above, combined impact collector and fan 716c includes a ferromagnetic element 716g, which is magnetically coupled to magnetic coupler 730. Preferably, ferromagnetic element 716g is of a relatively low mass, so that it imposes very little additional load on electric motor 728; the smallest mass ferromagnetic element capable of ensuring positive magnetic coupling is employed. Of course, ferromagnetic element 716g must be carefully placed in the center of the combined impact collector and fan 716c so that rotation efficiency of combined impact collector and fan 716c is not adversely effected. In a prototype collector unit, a small iron washer was effectively employed for ferromagnetic element 716g.

Preferably upper shell 716e, lower shell 716f, and combined impact collector and fan 716c are fabricated from a plastic material. Injection molded components of suitable quality can be inexpensively produced in large quantities. Preferably, lower shell 716f and/or combined impact collector and fan 716c are fabricated from a plastic material that exhibits good self-lubricating properties so that neither bearings nor additional lubricants are required to enable combined impact collector and fan 716c to freely rotate between the upper and lower shells.

Once disposable sample collection cartridge 716 has been collecting particulates for a desired period of time, the particulates need to be removed from combined impact collector and fan 716c for analysis. Preferably, a liquid sample that includes particulates, which were collected on the internal surfaces of the sample collection cartridge, will be prepared, as most analytical techniques are adapted to process liquid samples. While many techniques are known for preparing a liquid sample, the present invention preferably employs a rinse station specifically designed to prepare a liquid sample from a disposable sample collection cartridge 716.

In the most generic embodiment, the rinse station will use a known volume of rinse solution to extract a liquid sample from a disposable sample collection cartridge 716. To enhance rinsing, a wetting agent or surfactant can optionally be added to the rinse solution. It is anticipated that a heated rinse fluid will be particularly useful in cold environments. As the rinse station is to be field portable, it is likely that the rinse station will be employed in unheated conditions in cold climates. If the analytical technique to be employed is based on culturing biological organisms, then a rinse solution that is nontoxic to such organisms must be employed. Preferably, a phosphate buffer rinse solution will be used when applying such culturing techniques. Other contemplated rinsing enhancements that can be incorporated into the rinse station include an ultrasonic transducer that applies an ultrasonic pulse to the disposable sample collection cartridge during rinsing, or a vibration unit that vibrates the disposable sample collection cartridge during rinsing, or an electric motor that rotates the combined impact collector and fan in the disposable sample collection cartridge during rinsing.

Figure 30A:
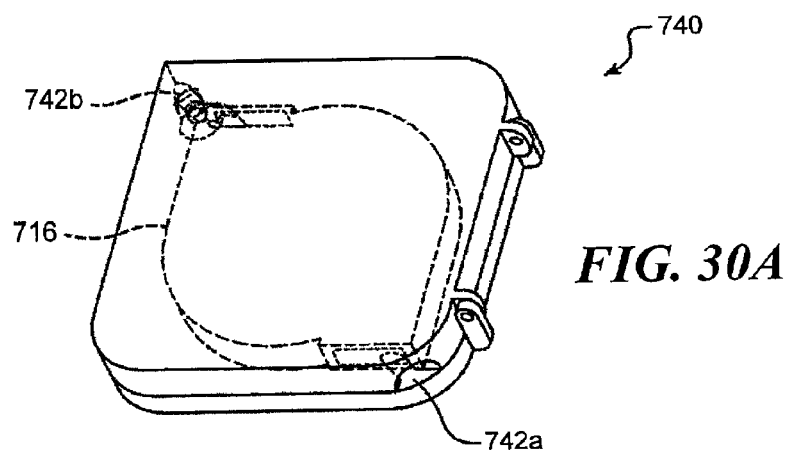
FIG. 30A is an isometric view of a disposable rinse cassette employed when extracting a sample from the sampling cartridge of FIG. 29A.
Figure 30B:
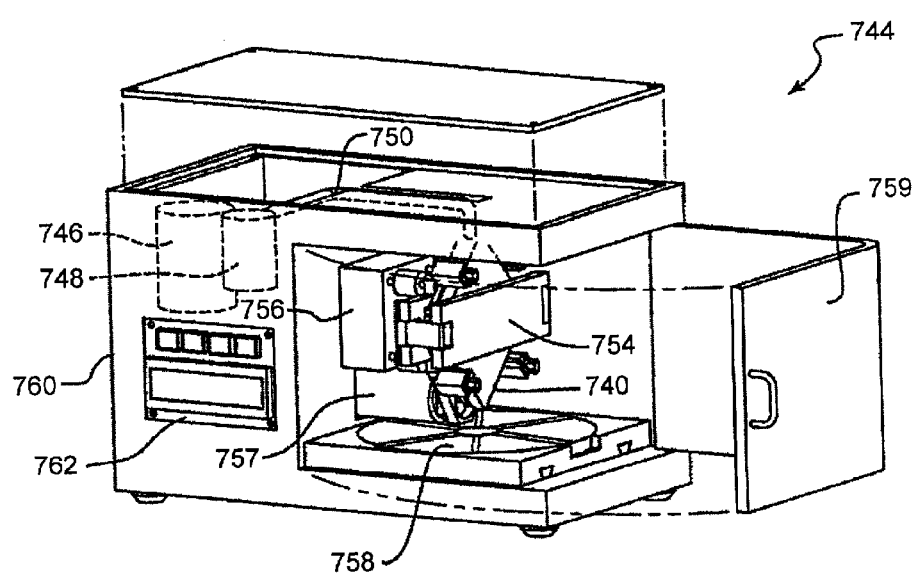
FIG. 30B is an isometric view of a preferred embodiment of a rinse station employed to extract a sample from a sampling cartridge that is inserted into the rinse cassette of FIG. 30A.

FIGS. 30A and 30B illustrate elements of a preferred rinsing station. In FIG. 30A, a rinse cassette 740 is shown, with a disposable sample collection cartridge 716 held inside the rinse cassette. Preferably an interior surface of rinse cassette 740 is contoured to approximately match the shape of disposable sample collection cartridge 716, thereby minimizing a volume of rinse fluid that will be injected into rinse cassette 740 during rinsing. Rinse cassette 740 includes a fluid port 742a through which the rinse fluid is injected into rinse cassette 740, and a fluid port 742b that includes an integral pinch valve. When the pinch valve is actuated after the rinsing step is complete, a sample of the rinse fluid containing particulates that have been rinsed from combined impact collector and fan 716c is removed from rinse cassette 740.

After the disposable sample collection cartridge 716 is inserted into rinse cassette 740, the rinse cassette is then inserted into a rinse station 744, illustrated in FIG. 30B. Rinse station 744 includes a rinse fluid reservoir 746, a fluid pump 748 that enables a precisely metered volume of rinse fluid to be injected into the rinse cassette, and a fluid line 750 in fluid communication with fluid pump 748, rinse fluid reservoir 746, and rinse cassette 740 that is held in place by a bracket 754. When rinse cassette 740 is properly positioned and latched in place by bracket 754, fluid port 742a of rinse cassette 740 is in fluid communication with fluid line 750. Thus, a precisely metered volume of rinse fluid can be injected into rinse cassette 740. Because the pinch valve associated with fluid port 742b is not actuated, rinse fluid injected into rinse cassette 740 will be retained within the rinse cassette until a sample is withdrawn by actuating the pinch valve.

Rinse station 744 also includes a vibration unit 756. When a rinse cassette has been placed into rinse cassette bracket 754 and filled with a precisely metered volume of fluid, vibration unit 756 is energized to vibrate the combined impact collector and fan disposed within rinse cassette 740. This vibration aids in removing adhered particulates from the surfaces of the combined impact collector and fan. It is contemplated that an ultrasonic transducer unit can alternatively replace vibration unit 756 to provide ultrasonic pulses that loosen the particulates from the surfaces of the collector.

When a rinse cassette is properly positioned and held in place by bracket 754, fluid port 742b and its pinch valve are disposed immediately adjacent to a solenoid unit 757. Once the rinse cycle is complete, solenoid unit 757 is energized, and the pinch valve associated with fluid port 742b is actuated. Fluid port 742b of rinse cassette 740 is disposed immediately above a lateral flow disk 758. The rinse liquid injected into rinse cassette (carrying particulates removed from the combined impact collector) drains onto the lateral flow disk, where it is collected for analysis. It is contemplated that another type of sample collector, such as a vial or ampoule (not shown), will be placed under fluid port 742b to collect the sample.

Finally, rinse station 744 includes a housing 760 that substantially encloses rinse fluid reservoir 746. Pump 748 and solenoid unit 757 are also enclosed by housing 760, and lateral flow disk 758 and rinse cassette bracket 754 are enclosed by a removable screen or door 759. A control panel 762 enables an operator to control pump 748, vibration unit 756, and solenoid unit 757 during the rinse cycle.

Alternative embodiments of rinse cassette 740 and rinse station 744 are contemplated. It may be desirable to enable a sealed rinse cassette or the combined impact collector and fan to be rotated by an electric motor (not separately shown) during the rinse cycle, to further aid in the removal of attached particulates. Rinse cassette 740 could not be rotated in this fashion, as the rinse fluid would leak out of fluid port 742*a* during the rotation. A pinch valve (not separately shown) could be included in fluid port 742*a*, so that rinse fluid cannot enter or exit the rinse cassette unless the pinch valve is actuated. This modification would require either an additional solenoid (also not shown) to be included in rinse station 744 to actuate the added pinch valve associated with fluid port 742*a*. Alternatively, a fluid line in fluid communication with fluid port 742*b*, pump 748, and rinse fluid reservoir 746 could be added to rinse station 744, so that fluid port 742*b* would be used to both fill and drain the rinse cassette, eliminating the need for fluid port 742*a*, or an additional solenoid unit and pinch valve.

To minimize the volume of reagents required, and to minimize the amount of waste generated, it is preferred that small volumes of rinse fluid be employed. It is anticipated that from about 1 to about 5 ml of rinse fluid represents a preferred range. However, it should be understood that more or less rinse fluid can be employed, depending on the nature of the particulates collected, the size of the disposable sample collection cartridge, and other factors.

Exemplary Identification Units

The specific identification unit (or units) that are employed in a mail sampling system in accord with the present invention depend upon the contaminant that is to be detected. Unfortunately, systems that can accurately identify any potentially threatening material are not readily available. Gas chromatography coupled with either mass spectrophotometers or infrared spectrophotometers can provide at least qualitative data aiding to identify a collected particulate; however, such units are generally quite expensive. Much less expensive and more compact systems can be employed if one wishes to detect a specific substance. For example, determining if a sample is anthrax can be done relatively easily.

Thus, inclusion of an appropriate identification unit 924 in the mail sampling system first requires a decision regarding the potentially harmful substances that may be introduced into the mail system. Currently, the list of potentially threatening agents is relatively short. The list includes radioactive materials (which can be easily detected using readily available instruments before mail is introduced into the mail sampling system), a relatively small number of biological agents (such as anthrax, smallpox, botulism, and plague), and a relatively small number of chemical agents (such as ricin, cyanide, and explosives) are the most likely threats to be included in a parcel. Providing an identification unit specifically adapted to detect the presence of any one of the above listed chemical or biological agents is a relatively straightforward task.

For example, anthrax spores can readily be detected by employing polymerase chain reaction (PCR) technology, implemented by Idaho Technology Inc.'s (Salt Lake City, Utah) RAPID PCR thermocycler. Empirical studies have confirmed that a radial arm collector can be employed to collect a wet sample that can be analyzed with excellent sensitivity using PCR technology (the sample in question utilized *Bacillus globigii* (BG) spores, which is often employed in place of actual anthrax spores, due to its low toxicity and similar particle size). It is expected that PCR technology could be optimized to identify other biological pathogens as well.

A second technology specifically adapted to identify anthrax, which is commercially available and can be readily integrated into a mail sampling system, employs immunoassay strips from Tetracore, Inc. While not as sensitive as PCR technology, the immunoassay strips are very simple to use (requiring only a few drops of a liquid sample) and are well suited to rapid detection of a significant biological presence, such as a medically significant quantity of anthrax spores placed in an envelope. Both of these technologies can provide a test result in less than 20 minutes.

Other identification units currently under development by a variety of vendors, are also expected to be useful in the mail sampling system. One technology developed by Micronics, Inc., which promises to be able to provide a plurality of different identification units, each capable of specifically identifying a target compound, uses microfluidic cards. Such cards could readily be employed in the mail sampling system to serve as the detection units.

Figure 31:
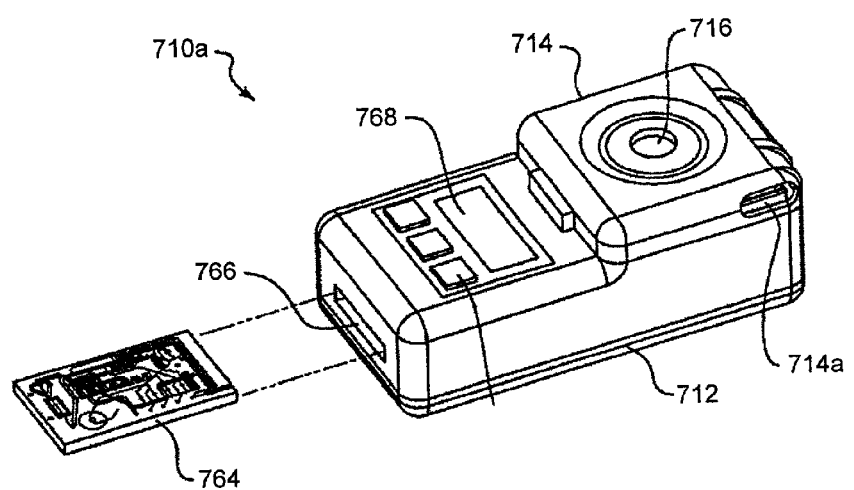
FIG. 31 is an isometric view of a portable sampler and integrated sensor unit in accord with another embodiment of the present invention.
Figure 32:
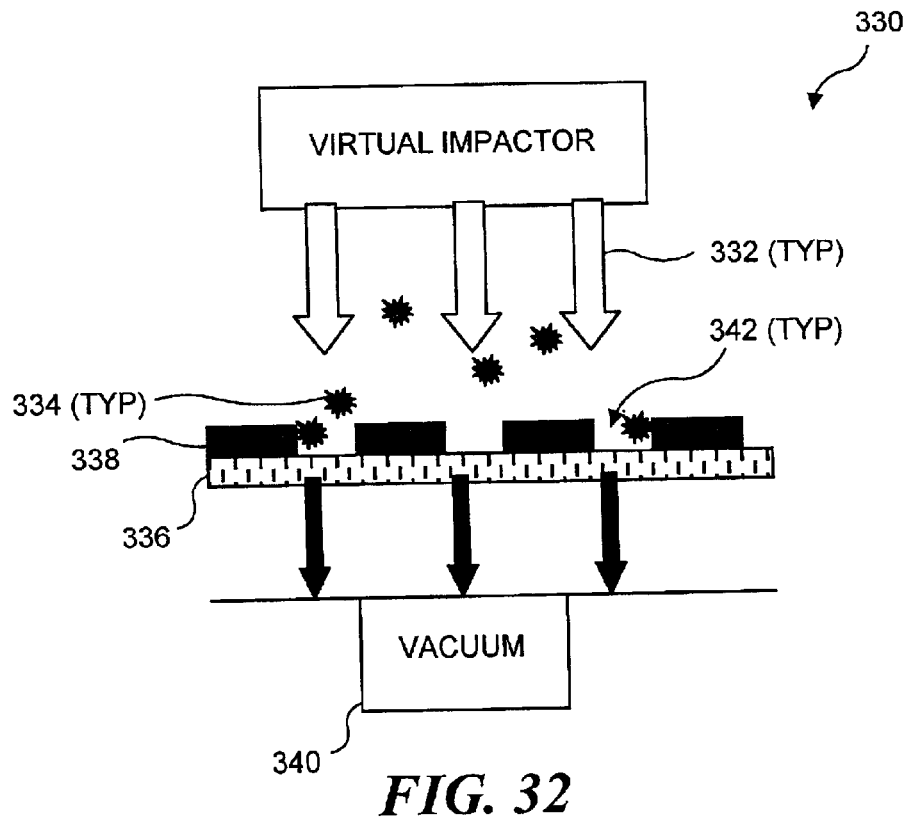
FIG. 32 is a schematic view of a porous archival impaction surface for use in the present invention.

FIG. 31 illustrates a personal air-monitoring unit 710*a*. This embodiment incorporates a detection unit 764, which is capable of identifying a specific particulate of interest. Detection unit 764 is intended to be disposable and to be replaced at the same time as disposable sample collection cartridge 716, following its use in attempting to detect substances in the sample that was collected by the personal air-monitoring unit. Note that such a disposable detection unit 764 can be readily incorporated, along with disposable sample collection cartridge 716, into the detecting sampler of the mail sampling system of the present invention.

Note that detection unit 764 is specifically designed to detect a particular chemical or microorganism (or a class of chemicals or pathogens), and will not be sensitive to non-target agents. Thus, if anthrax spores have been collected, but detection unit 764 is designed to detect nerve gas agents, the presence of anthrax will not be reported. While it would be preferable for detection unit 764 to be capable of detecting all types of particulates of interest, i.e., all harmful chemical/biological agents, the state of the art of detection technology is not yet capable of implementing such a wide spectrum detector at a reasonable cost and complexity. However, a wide variety of detectors for specific substances can be employed. Preferably, detection unit 764 is adapted to detect either a chemical, a biological pathogen, a biological toxin, an allergen, a mold, or a fungi. Multiple detection units, each specific to a chemical or pathogen of interest, can be included in the mail sampling system.

Preferably, detection unit 764 is configured in an elongate, relatively thin card shape and includes a plurality of microfluidic channels. Detection unit 764 includes all of the reagents required to perform the desired analysis. The use of microfluidic architecture enables relatively small quantities of reagents to detect a substance in a relatively small quantity sample.

Micronics has developed several lab-on-a-chip technologies that are implemented as low-cost plastic, disposable, integrated microfluidic circuits, typically in credit card-sized cartridges. These microfluidic channels were originally developed using microfabrication techniques established within the semiconductor manufacturing industry. Microfluidic channels, on the order of hundreds of microns in diameter, are now easily fabricated on silicon chips and other substrates. Fluids flowing in these small channels have unique characteristics that can be applied to different detection methodologies, including cell separation without centrifugation or filtration. The miniaturization of these processes ensures that minimal volumes of reagents will be needed, minimal volumes of samples will be required, and minimal volumes of waste will be generated.

These microfluidic systems are ideal for detecting a substance in the same instrument in which a sample has been collected, eliminating the need to transport the sample to a centralized laboratory, and providing immediate or real time results. The O.R.C.A. μFluidics™ product line of Micronics, Inc. is particularly well suited for this use. The card-based detection system used in this product usually includes a standard sample input port, one or more reagent introduction ports, sample storage structures, and waste compartments, and may also contain various microfluidic separation and detection channels, incubation areas, microfluidic reactors, and valves, details of which are not specifically illustrated.

With respect to FIG. 31, detection unit 764 is exemplary of the O.R.C.A. μFluidics™ product line. It should be noted that the specific internal layout of a detection unit adapted to detect nerve gas might be quite different than that of a detection unit intended to detect another type of chemical or biological agent, and the internal design of detection unit 764 is for illustrative purposes only. Regardless of the specific internal design used in the detection unit, each different type of detection unit will include standard interface port to enable samples to be introduced into the detection unit, as well as to enable a result to be displayed It is expected that when the target particulate is a biological organism or pathogen, flow cytometry (the counting and characterization of biological cells) will be a preferred detection methodology employed in detection unit 764. It is further expected that immunoassay and nucleic acid base detection methods can be employed in a microfluidic detection unit.

Referring once again to FIG. 31, detection unit 764 is a compact and disposable device that can be readily utilized in conjunction with any impact collector. As shown in FIG. 31, detection unit 764 is inserted into a slot 766 in primary housing 712 of personal air-monitoring unit 710*a*. While personal air-monitoring unit 710*a* includes a disposable radial arm impact collector (disposable sample collection cartridge 716, as described above), detection unit 764 is in no way limited to being employed with only that type of impact collector. In fact, detection unit 764 can be employed with any type of sampling system that can provide a liquid sample. It is contemplated that both the disposable and non-disposable radial arm collectors described above can be beneficially incorporated into mail sampling system 900. As described above, the detecting sampler that includes a non-disposable radial arm collector also includes a wash rinse fluid and collection reservoir. Such a triggering sampler is easily modified to provide the liquid sample collected to detection unit 764, rather than to a sample collection reservoir that is removed and taken to an off-site lab for analysis. If a disposable radial arm collector and detection unit 764 are both incorporated into mail sampling system 900, then an additional subsystem will be required to provide a liquid sample (from the particles collected by the disposable radial arm collector) to detection unit 764. Those of ordinary skill in the art will recognize that elements from the rinsing station described above could be included in mail sampling system 900 to facilitate the provision of such a liquid sample.

While the incorporation of the rinsing station elements would likely result in a somewhat more complicated mail sampling system, it should be noted that the use of disposable radial arm collectors have an inherent advantage over the use of a non-disposable radial arm collector. Specifically, the nondisposable radial arm collector requires cleaning and/or disinfecting after each sample is collected to prevent any cross contamination from occurring between samples. Thus, a disinfecting rinse fluid reservoir and a spent disinfecting rinse fluid reservoir would also preferably be included (similar to the elements of FIG. 37 but directed toward the radial arm collector of the detecting sampler). Once a sample has been collected by a disposable radial arm collector and analyzed by a disposable detection unit, each disposable item can be replaced with a fresh unit, without requiring the disinfecting rinse.

Detection unit 764 generally requires very little power, because of the very small volumes of fluid being manipulated. That power can either be provided by an disposable button cell type battery, or detection unit 764 can be adapted to obtain the required electrical power from the power supply included in mail sampling system 900. Results from detection unit 764 can be provided to a operator in several different ways. A display can be included in the mail sampling system enabling the results to be displayed. Because detection unit 764 is disposable, and will be removed from the mail sampling system after each use, a separate portable reader with a display can be provided. An operator would remove detection unit 764 from the mail sampling system, place it into a slot in the portable reader, enabling the results to be displayed on the reader. The portable reader can be generally configured like personal air-monitoring unit 710*a* of FIG. 31, but without disposable sample collection cartridge 716, and the prime mover used to rotate disposable sample collection cartridge 716. A display 768 is included on personal air-monitoring unit 710*a* so that the results of the analysis and detection process carried out by detection unit 764 is displayed to an operator. It is also contemplated that display 768 could be included with detection unit 764, although the result would likely increase the cost of each disposable detection unit 764.

While not separately shown, it should be understood that disposable sample collection cartridge 716 will include a fluid port through which the rinse fluid that has removed particulates from the impact collector will flow. Furthermore, fluid lines (not shown) enable detection unit 764 to be connected to one of the detecting sampler systems, as described above, to receive the liquid sample in sample input port 765 of detection unit 764.

Detecting sampler systems in accord with the present invention could also be integrated with other types of detector units. The microfluidic based detectors discussed above are merely exemplary, and should not be considered limiting in regards to the present invention. Other suitable detection units are likely to include color change-based test strips, such as those available from Tetracore, Inc. for detecting the presence of anthrax, and sensor-on-a-chip technologies that are available from a number of different companies (for example, see http://www.taosinc.com/pressrelease_sensor.htm). It is expected that immuno-assay based-detection systems, such as flow cytometry and fluorescence-based systems, and nucleic acid-based detection systems will be particularly useful.

Archiving Sampler

As noted above with respect to FIG. 1, an optional element of mail sampling system 900 is archiving sampler 922. If included at the same time that a sample is collected for identification by the detecting sampler, another virtual impactor can be employed to collect another sample of concentrated particles for deposition onto an archival surface. By carefully controlling and documenting a position of the sample deposited on the archival surface during each sampling event, a time/date stamped record for the sample is generated. The archiving sampler can periodically deposit spots of particles on an archival surface, and can produce a spot with any desired frequency, such as once per minute or once per month, or alternatively, only when triggered to do so by the triggering sampler. Preferably, when incorporated into a mail sampling system, the archiving sampler automatically generates a spot whenever the detecting sampler collects a sample in response to the signal from the triggering sampler.

The ability to create an environmental archive is of great utility in a forensic analysis of contaminated mail. For example, upon discovery that a number of contaminated pieces of mail have passed through a particular post office in the United States, it would be extremely useful to consult a permanent record of archived samples from that post office. An archive, which would consist of a small piece of material (a few square inches) with thousands of small spots, could allow an operator to pinpoint the precise time when the contaminated mail was introduced into the system. If used in conjunction with electronic mail sorting records, the archive could enable determination of the source of the contaminated mail. In some instances, such a method could be the only viable means for determining the party responsible for the contamination.

The archiving sampler works by collecting an additional sample with a virtual impactor, and directing the resulting concentrated particle flow onto an archival quality surface. After a single spot is created, the surface is moved relative to the virtual impactor so that a plurality of non-overlapping spots are produced, one or more for each sample taken. Simultaneously, control 936 (see FIG. 1) records the time that each spot was created. Because of this integrated control, e.g., using a programmed microprocessor in control 936, the archiver can use advanced logic in determining when to sample. The sampling frequency can be increased or decreased based on environmental factors that include particle count, biological particle count, temperature, humidity, and pressure.

Once the particulate concentration of the fluid stream has been enhanced by the use of a virtual impactor as described above, collection of the concentrated particulates can readily be effected. It should be noted that impact based collectors (as opposed to the virtual impact collectors described above) can also achieve significant particulate concentrations. However, the impact surface portion of such impact collectors is generally an integral portion of the impact collector, and it is not practical to archive the impact collector itself. The collection surface of impact collectors is generally rinsed with a fluid to obtain the collected particulates for analysis. While particulates collected in that manner could also be archived, the volume of fluid required to rinse the collected particulates from the impact collector significantly increases the volume of material that must be handled. Furthermore, the steps of rinsing, collecting, and storing the rinsate add significant time and effort (and thus cost) to archiving the particulates. In contrast, the use of a virtual impactor enables an archival surface to be employed that is a separate component and can readily be removed from the virtual impactor and replaced with a fresh surface for collecting particulate samples. The archival surface on which the samples have been collected can then be stored without significant additional processing until needed.

Any surface material amenable to spot deposition can be used, and one of several different deposition methods can be employed. For example, the minor flow can be directed toward a filter through which the fluid in the minor flow can pass and upon which the particulates are deposited. Alternatively, the particulates in the minor flow can be directed toward an impaction surface behind which is disposed a vacuum that draws the particles onto the surface. The archival (impaction) surface can also be coated with a material that aids in the deposition and retention of particulates that have impacted on the surface, as discussed above.

Referring now to FIG. 5, once the archiving sampler receives a signal from control 936, a fan/blower 953 servicing the archiving sampler is energized, and particulate laden air begins to flow through a virtual impactor 954. As described above, the major flow 958 is directed to HEPA filter 926, and the minor flow 956 is directed toward archival surface 963. The position of archival surface 963 relative to virtual impactor 954 is controlled by a prime mover 965. Prime mover 965 is controlled by control 936, which records the time and position of archival surface 963, so that a specific spot deposited on archival surface 963 can be correlated to a specific time (and most preferably, to a specific parcel). Archival surface 963 can be coated with different materials to enhance the archival surface's ability to collect particles, and even to sustain biological particulates.

The following description discusses an archiving sampler in a context not necessarily associated with mail sampling system 900. However, it should be understood that the archiving sampler described could readily be included in the mail sampling system.

FIG. 32 schematically illustrates an archival collection system 330 that uses a porous hydrophilic filter medium 336 as the deposition surface. Preferably a hydrophobic material 338 is deposited on a porous hydrophilic filter medium 336. Openings 342 in hydrophobic material 338 direct particulates 334 entrained in a minor flow 332 toward locations on porous hydrophilic filter medium 336 upon which the particulates are collected. The fluid in which the particulates are entrained passes through the porous hydrophilic filter medium 336, leaving the particulates deposited on the surface. A vacuum source 340 can be beneficially employed to ensure that the minor flow fluid passes through the porous filter, rather than being diverted around the sides of the porous filter.

Preferably, the area between virtual impactor outlet for the minor flow and the filter is sealed, so the particulates will not be lost prior to impact on the surface of the filter medium The sealing preferably extends between the bottom of the porous filter and vacuum source 340. While not readily apparent from FIG. 32, it should be understood that porous hydrophilic filter medium 336 is moved relative to the position of the minor flow, so that particulates collected from the minor flow at different times are deposited at different (and known) locations on the porous filter medium. In general, it is anticipated that it will be simpler to move the archival surface than the virtual impactor, although movement of either the virtual impactor or the archival surface will enable particulates to be deposited on specific spaced-apart portions of the archival surface, at different times.

As shown in FIGS. 32 and 33, the minor flow is directed toward the archival surface as three separate streams. It should be understood that either fewer or more than three minor flow streams could instead be employed. The benefit of employing multiple minor flows is that, as described above, individual virtual impactors can be fabricated to selectively direct particulates of a desired size into the minor flow. Thus, by employing a plurality of virtual impactors, each concentrating a different particulate size into their respective minor flows, particulates of different sizes can be directed onto different locations of one or more archival surfaces. Alternately, particulates of the same size can be deposited in different locations, permitting duplicate samples to be taken to facilitate multiple testing, perhaps at different times or at different locations.

Figure 33:
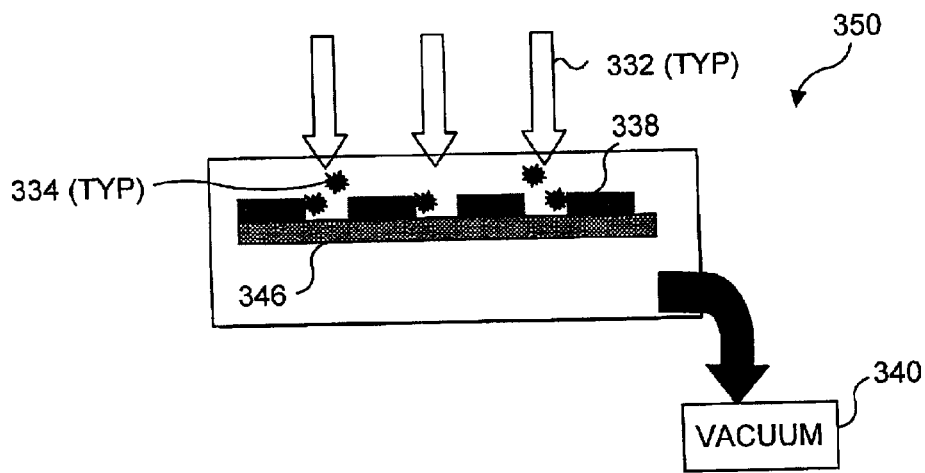
FIG. 33 is a schematic view of a nonporous archival impaction surface for use in the present invention.
Figure 34:
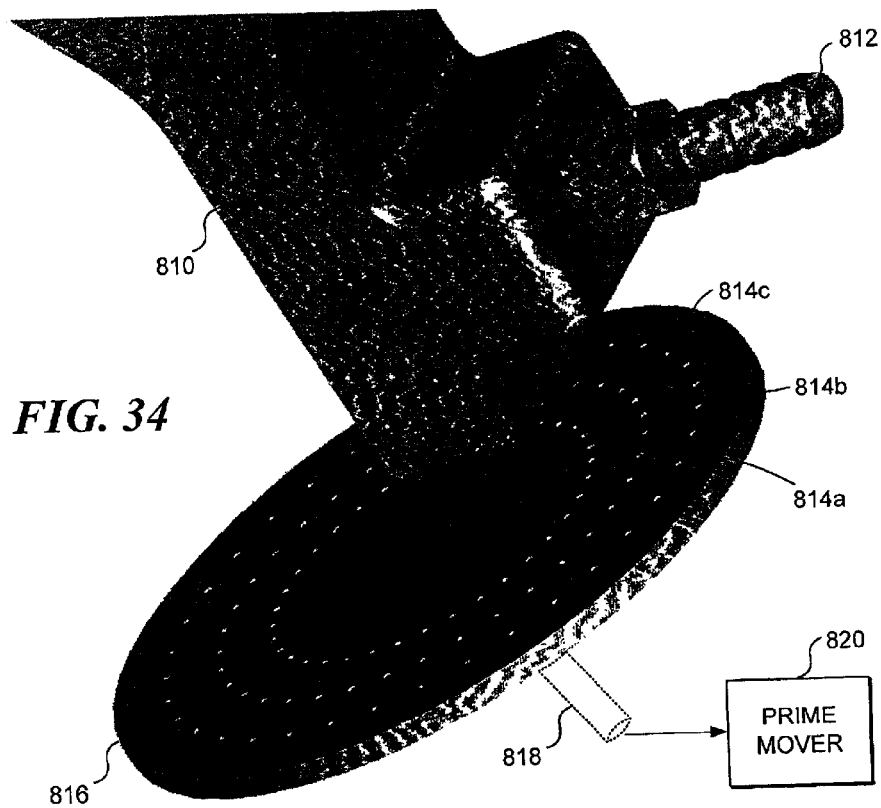
FIG. 34 is an isometric view of a virtual impactor and an archival surface for use in the present invention.
Figure 35A:
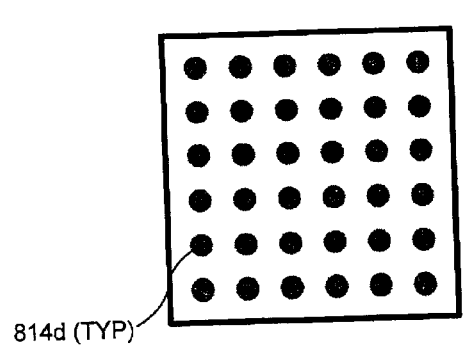
FIGS. 35A and 35B illustrate two embodiments of archival surfaces, each having a different pattern of archival spots.
Figure 35B:
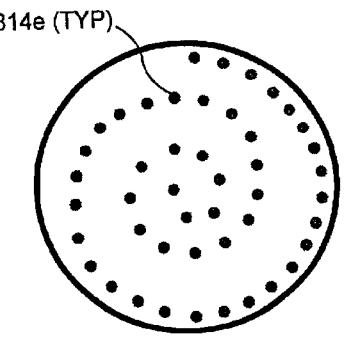

FIG. 33 schematically illustrates an archival collection system 350 that uses a nonporous archival surface 346 as the deposition surface. In archival collection system 350, the particulate-laden fluid is accelerated through a minor flow outlet nozzle of a virtual impactor to impact the surface. Preventing particulates from bouncing off of nonporous archival surface 346 is a key aspect of this approach.

In both FIGS. 32 and 33, a surface coating or layer has been applied to the archival surface, to define receptacles for spots of particles. Such a coating (hydrophobic material 338) is not required, but is a useful addition. Regardless of whether a porous or nonporous archival surface is employed, several different surface treatments may be useful in increasing the efficiency of spot formation. For example, a common problem with surface impaction is that particles bounce off the surface, return to the fluid stream, and are swept away. It is preferable to coat the surface to promote particle adhesion. Such surface coatings include, but are not limited to, charged chemical species, proteins, and viscous substances that reduce the likelihood that the particulates will bounce away from the archival surface. A person skilled in the art will recognize that many other coatings, having other physical and chemical properties, can be beneficially employed to aid in the collection of specific types of particulates. In at least one embodiment, the coating is on the order of 100 microns thick, while the archival surface itself is on the order of 100 mm thick.

It should be noted that the archival surface, with or without a coating, need not be flat. Preferentially, a surface with portions raised significantly above the bulk of the surface can also be used to collect spots of particulates. For example, a textured surface having portions raised substantially above a background surface can be used to collect spots of particulates. Such textured surfaces are disclosed in commonly assigned U.S. Pat. No. 6,110,247, the disclosure and drawings of which are hereby specifically incorporated herein by reference. Such surfaces reduce the tendency of particles to bounce and therefore increase spot formation efficiency.

The archival surface preferably includes a material that helps maintain the particulates deposited on the archival surface in good condition, without substantial degradation. For some particles, such as living cells, this material may be a liquid that contains nutrients. Applying a hydrogel or equivalent coating on the archival surface enables localization of water. The water can be used to deliver salts, sugars, proteins, and other nutrients to enable the cells to survive on the archival surface during the time interval between their deposition on the archival surface and subsequent analysis of the collected samples.

The coatings discussed above in regard to an impact surface can be also can be used on an archival surface. Also, some portion of the analysis/detection scheme can be included as part of the surface. For example, if the analysis employed to detect a specific particulate involves incubating the collected particulates (some of which may be bioparticles) with a reagent, the reagent can be incorporated onto the surface so that the incubation period is initiated upon deposition of a sample on the surface.

Orientation of Archival Surface Relative to Virtual Impactor

Because the location of a "spot" of particulates deposited on the archival surface is indicative of a time at which the particulates were collected, it is preferable to move the archival surface relative to the virtual impactor, at least at defined spaced-apart times, to form spots of particulates (or continually to form streaks of particulates). Moving the archival surface at successive time intervals permits multiple sample spots to be deposited on a single archival surface without commingling the spots. The time at which each spot is deposited is associated with the spot. Alternatively, the particulates can be continually deposited on the archival surface, yielding a streak of particles.

One embodiment for providing intermittent relative motion between the archival surface and the stream of particulates is shown in FIG. 34, in which a virtual impactor 810 is fixedly mounted over a movable archival surface that is formed in the shape of a disk 816. The minor flow of particulates is directed at the disk. A major flow 812 containing particulates of nontarget size exits virtual impactor 810 orthogonally with respect to the minor flow, to prevent particulates entrained in the major flow from being deposited on disk 816. While not shown, it should be understood that disk 816 could be further separated from major flow 812 by a protective housing.

The nozzles directing the minor flow toward disk 816 cannot be seen in FIG. 35, but virtual impactor 810 includes three minor flow outlets, all of which are oriented to direct particulates towards spot deposition areas 814*a*–814*c*. As disk 816 rotates beneath virtual impactor 810, the minor flow nozzles of virtual impactor 810 direct particulates to a new deposition area. Note that disk 816 shows three concentric rings of spaced-apart spots in three different annular deposition areas; area 814*a* defining the inner ring of spots, area 814*b* defining a middle ring of spots, and area 814*c* defining an outer ring of spots. Disk 816 is preferably indexed (not shown) so that the spots are defined at discrete predetermined positions around the deposition areas, to enable the position of each spot to be associated with a specific time, and to enable the particulates to be accurately directed toward the disposition of each spot on the disk. It should be understood from FIG. 34, and the preceding description, that deposition areas 814*a*–814*c* preferably each include a plurality of depressions formed into disk 816, either as openings in a coating on disk 816, or depressions formed on the surface of disk 816, where each spot of particulates is to be deposited. However, while such openings/depressions are expected to increase collection efficiency, they are not required.

Disk 816 can be moved using an appropriate prime mover 820, such as a stepping motor. As shown, one such means includes a shaft 818 detachably coupled to disk 816 and driven by prime mover 820. It is expected that disk 816 will remain stationary for a desired time interval, and then will be rotated a sufficient amount to align another set of depressions in the deposition areas with the minor flow nozzles of virtual impactor 810, so that the spots of particulates can be deposited within the depressions, if depressions are indeed provided. The virtual impactor can be cycled on and off during the movement, if desired.

As noted above, it is also possible to deposit streaks of particulates instead of spots. In a more elaborate embodiment, the archival surface is continually moved at a fixed rate, resulting in annular rings defined by streaks of particles on the archival surface, instead of discrete spots. The use of streaks somewhat simplifies the operation of the collector, in that it can operate continuously, rather than being cycled on and off.

It will be understood that different configurations of archival surfaces can be employed (i.e., shapes other than disks), and that different configurations of spots can be deposited on archival surfaces (i.e., configurations other than streaks or concentric rings of spots). FIG. 35A shows a quadrilateral shaped archival surface on which deposition areas 814*d* are oriented in an array extending orthogonally in two directions. FIG. 35B shows a second disk-shaped archival surface, on which deposition areas 814*e* are oriented in a spiral array. It will also be appreciated that any of deposition array 814*a*–814*e* illustrated and discussed above can be one or more of: (1) a depression on the archival surface; (2) an opening in a coating on an archival surface; (3) an aggregate of particulates deposited in a spot; and (4) an area in which an aggregate of particulates are to be deposited without regard to the shape of the deposit.

Figure 5:
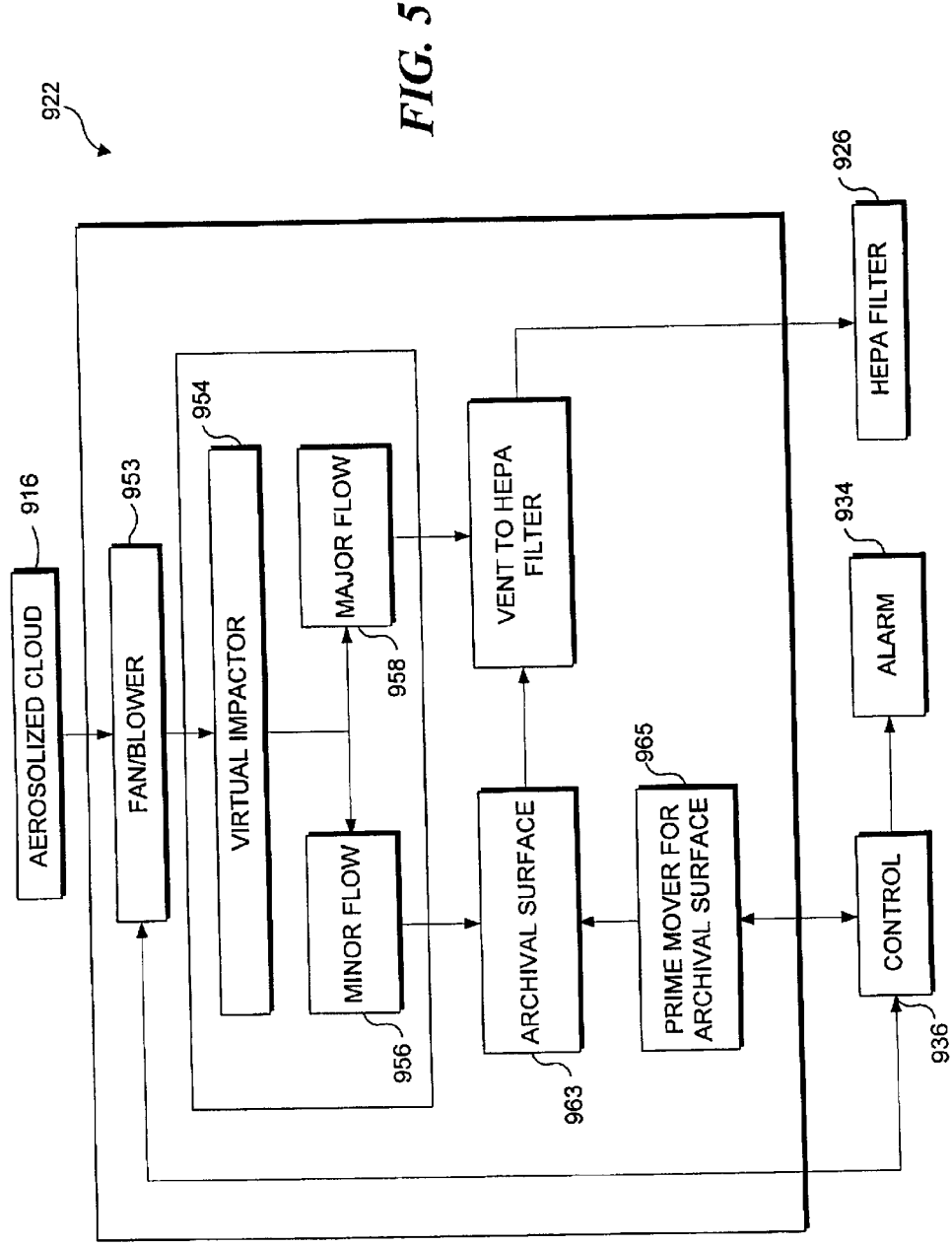
Figure 36:
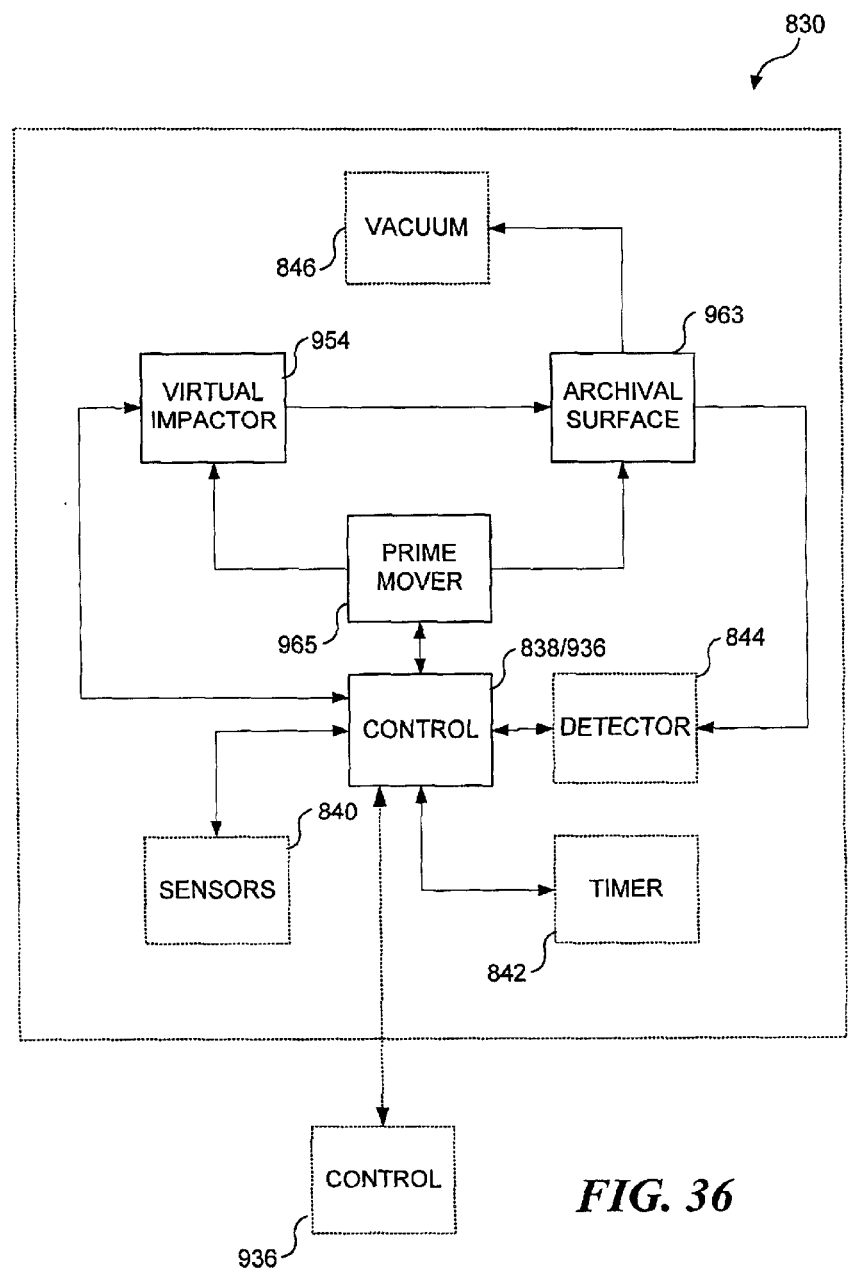
FIG. 36 is a block diagram illustrating the components of an exemplary archival spot collection system.

FIG. 36 illustrates an archival system 830, which is another embodiment for collecting and archiving particulates entrained in a flow of fluid. A fan, such as fan/blower 953 (see FIG. 5), which can be centrifugal fan or an axial fan driven by a motor or other prime mover, is normally required to force fluid through system 830. The virtual impactors used in the present invention to separate a flow of fluid into minor and major flows function best when the fluid passes through the virtual impactor at about a predefined velocity. While a source of some fluid streams may have sufficient velocity to pass through a virtual impactor without requiring a fan to drive them, it is contemplated that many applications of system 830 (such as collecting particulates within the containment chamber of the mail sampling system of the present invention) will require a fan. While as shown in FIG. 5, fan/blower 953 forces a fluid into an archiving sampler, those of ordinary skill in the art will recognize that the fan could alternatively be positioned to draw fluid through archiving sampler 922 or system 830.

System 830 also includes virtual impactor 954 and archival surface 963. Archival surface 963 can incorporate any of the coating discussed above, or no coating. The configuration of archival surface 963 can include, but is not limited to a plate, a disk, or an elongate tape. Preferably, archival surface 963 can be readily removed and replaced with a new archival surface either when the original archival surface is full, or particulates deposited on the archival surface require analysis. A vacuum source 846 is optionally in fluid communication with archival surface, also as described above, to assist in the deposition of the particulates thereon. Archival surface 963 is coupled to prime mover 965 that moves the archival surface relative to virtual impactor 954 over time, so that particulates collected at different times are deposited on different portions of archival surface 963. It should be noted that prime mover 965 can instead optionally move virtual impactor 954, instead of, or in addition to, moving archival surface 963.

With respect to embodiments in which prime mover 965 is drivingly coupled to archival surface 963, several different types of motion are contemplated. If archival surface 963 is a disk, prime mover 965 will likely be used to rotate the disk. If archival surface 963 is an elongate tape, then prime mover 965 will likely be used to cause one or both of a take-up wheel or a drive wheel (not shown) to be moved, to cause a corresponding movement in the elongate tape. Note that archival surface 963 is a consumable component, which when full, will be replaced with a fresh archival surface.

As shown in FIG. 36, prime mover 965 is controllably coupled to a control 838. Note that the embodiment of FIG. 5 shows archiving sampler 922 controllably coupled to control 936. It should be understood that control 936 and control 838 could either be separate units, or the same unit. If separate units, then control 838 should be coupled to control 936, so that system 830 can be activated whenever the triggering sampler or the detecting sampler indicates that an archival sample is also required. The purpose of control 838 is to control the movement of prime mover 965 to achieve the desired movement at least one of virtual impactor 954 and archival surface 963. It is anticipated that if a separate control 838 is employed, it can be one of a computing device, an application specific integrated circuit (ASIC), a hard-wired logic circuit, or a simple timing circuit. In at least one embodiment, software is executed to control the operation of the device, and the control includes memory and a microprocessor. This software preferably includes a program that determines the positioning of the archival surface relative to the minor flow. The software may also include a program that controls the schedule for taking environmental samples at predetermined times, thereby producing a spot on the surface at specific spaced-apart times. In addition, the control may execute logic that modifies the sampling schedule in accordance with algorithms that are responsive to onboard sensors 840. Finally, the software can monitor the particulate collection, generating a log of the actual time when each samples is taken in association with the disposition of the spot deposited on an archival surface at that time. This log facilitates correlating a specific sample (i.e., a specific spot) with a particular time at which the spot was deposited.

Empirical tests of a prototype device, functionally similar to system 830, and employing a polymeric tape as an archival surface, have confirmed the ability of a virtual impactor to deposit spots of particulates on a movable archival surface.

System 830 may beneficially include sensors 840, which communicate with control 838 to cause a sample to be collected in response to an event that is detected by one or more sensors. Such a system might be equipped with temperature and pressure sensors, and when predetermined levels of temperature and pressure are achieved, controller 838 (based on sensor data from sensors 840) can be programmed to initiate a sampling event, to deposit particulates on the archival surface for later analysis in response to the sensor readings. Based on the detection of a specific environmental factor by such a sensor, or in accord with a sampling protocol programmed into control 838, one or more of the following functions can be executed by control 838:

Generate a record of the environmental conditions at the time of spotting

Control the operation of any system components whose performance depends on a measured environmental parameters Manipulate a programmed sampling protocol based on measured environmental factors Produce an alert signal (by means such as radio transmission or hard-wired signal transmission) to notify an operator of an important change in the environmental conditions (as determined by programmed control parameters).

Referring once again to FIG. 36, a timer 842 is optionally included to provide a timing signal to control 838. Depending on the type of computing device (or logical circuit) employed for control 838, timer 842 may not be required. Many computing devices do not require a separate timer, and in its simplest form, control 838 may itself comprise a timer or timing integrated circuit.

One or more optional detectors 844 can be included, to analyze particulates deposited on the archival surface. It is expected however, that the archival surface will most often be removed from the system before any of the particulates (i.e. spots) are analyzed. By using a separate detector, the cost of system 830 can be reduced, as detectors are often sophisticated and expensive. Furthermore, many detection methods require particulates comprising the spots to be removed from the archival surface before being analyzed. If detector 844 requires the particulates comprising the spots to be removed from the archival surface prior to analysis, a particulate removal system (generally a liquid rinse directed at a specific spot) must also be incorporated. Particulates comprising the spots can also be removed by scraping, and other means.

Means for Removing Non Target Fiber Particles from the Samplers

Yet another optional subsystem prevents small paper and non-target fiber particles which pass through the prefilter from interfering with the collection of the target particles (i.e. the suspected chemical and biological contaminants). For example, the above mentioned prefilter will remove larger size paper fibers and particulates, but non-target fiber particles smaller than a pore or cut size of the prefilter will be present, along with any biological or chemical contaminants smaller than the cut size. It is not possible to pre-filter these very small paper fibers without also filtering out the target particles. Note that such non-target fiber particles are often present at significantly higher concentrations than the target particles themselves. Such non-target fiber particles can stick to surfaces and generate an undesirable build up. It has been empirically determined that such non-target fiber particles are particularly problematic with respect to impact collection surfaces, especially radial arm collectors. Such buildup can be readily removed by employing an enzyme, such as cellulase, in the rinse fluid. In embodiments in which a rinse fluid is continually flushed over the collection surface, the presence of cellulase in the rinse fluid will tend to catalyze paper fibers deposited on its surfaces, producing glucose, a soluble product of the enzymatic reaction, which is readily solubilized and rinsed away. While a cellulase enzyme is not explicitly illustrated in any of the drawings, a rinse fluid used for rinsing the collection surfaces is illustrated in FIGS. 3A and 4A, and it should be understood that such an enzyme can readily be incorporated into such rinse fluid.

It should be noted that such means for removing non target fiber particles will generally not be employed with an archiving sampler, as the archival collection surface of the archiving sampler is continually refreshed, and the fiber particle buildup is thus avoided, or at least minimized. Further, rinsing the archival surface will likely also remove the very particles that are to be archived, obviating any benefit provided by the incorporation of an archival sampler.

The enzyme cleaning process would preferably be regularly performed when the system is not screening parcels. A typical method for employing such an enzymatic rinse solution would be to apply the enzyme to the collection surfaces of the triggering and detecting samplers after a defined period of use. As described above, it is anticipated that a rinse fluid will be incorporated into some embodiments of the triggering and detecting samplers (see rinse fluid reservoir 959 in FIGS. 3A and 4A). While an additional rinse fluid supply dedicated to enzymatic rinsing for periodic cleaning can be provided, it is anticipated that incorporating the cellulase enzyme into rinse fluid reservoir 959 will be adequate. It should be noted that it is conceivable that the enzyme could be incompatible with the detection method employed to analyze a sample rinsed off of a collection surface, in either the triggering or detecting sampler. If so, then a separate rinse fluid reservoir should be employed; one dedicated to a rinse fluid not containing the enzyme for rinsing particles off of the collection surface to obtain a sample, and an additional rinse fluid reservoir dedicated to a rinse fluid containing the enzyme, for periodically removing accumulated paper fibers from the collection surface.

For cleaning using the enzymatic rinse fluid, the collection surface will be thoroughly moistened with the enzyme rinse. The enzyme rinse is allowed to coat the collection surface for a pre-defined period of time, to enable the enzyme rinse to saturate and degrade any accumulated buildup. The system is then energized, so that either a radial arm collector is rotated, or a jet of air is directed to a stationary collection surface, thereby dislodging fiber contaminants that have been loosened by the enzyme rinse cleaning fluid. Additional enzyme rinse fluid is directed at the collection surface. For stubborn build-ups, the process can be repeated. However, as it is anticipated that such buildups will negatively effect performance, it is preferred that such a cleaning cycle be performed regularly, to avoid allowing such build-ups to form.

Decontamination Means

As shown in FIG. 1, another optional element of mail sampling system 900 is decontamination means 932. It is contemplated that for mail sampling systems that include identification units, when an identification unit positively identifies the presence of a harmful chemical or biological agent, decontamination means 932 will be activated. This decontamination will reduce the risk of exposing operators who must access the containment chamber to remove the contaminated parcel, as well as reducing the risk of spreading the contaminant beyond the containment chamber. For mail sampling systems that do not include identification units, decontamination means 932 can automatically be activated whenever the detecting sampler is activated (i.e., whenever the triggering sampler indicates the presence of biological particles, or a particle count that exceeds a predefined threshold value).

Cecure™, which is available from Safe Foods Corporation, is a cetylpyridinium chloride (CPC)-based anti-microbial product that is highly effective against biological pathogens and has primarily been marketed as a food safety product because of its significant effectiveness against food-borne pathogens, including Listeria, *E. coli, Salmonella*, and *Campylobacter*. Not only does the Cecure™ product kill pathogens, but it also reduces the chance of recontamination because of the compound's ability to inhibit the attachment and regrowth of pathogens to treated surfaces, providing a continuing antimicrobial efficacy beyond the point of application.

An empirical study has been conducted to determine how effective a one percent (1%) CPC solution is likely to be in treating anthrax contaminated surfaces. The test employed *Bacillus globigii* spores, rather than actual anthrax, due to the serious exposure hazards of working with *Bacillus anthracis*. However, *Bacillus globigii* is commonly employed as a nonpathogenic surrogate for anthrax research. Used as a biocide, very low CPC concentrations (1%) have been demonstrated to accomplish over a 99% reduction of the spores of *Bacillus globigii* after only one minute of exposure.

As a biocide, CPC has been shown to kill spores of *Clostridium perfringens, Clostridium sporogenes, Clostridium tetani, Bacillus subtilis*, and *Bacillus athracis*. CPC offers the distinct and critical advantages of being immediately deployable, as well as being nontoxic in humans. In fact, CPC is so safe that it has been consumed in commonly available, over-the-counter oral hygiene products such as Scope™ mouth rinse and Cepacol™ lozenges, for more than 50 years. CPC is nonmutagenic and noncarcinogenic. It can, in some individuals, cause temporary skin irritations and can irritate mucous membranes when inhaled. All of these side effects are temporary. It has also been shown to have no deleterious effects on equipment in the food processing industry. Thus, it should have no ill effects when used in mail processing equipment.

Figure 37:
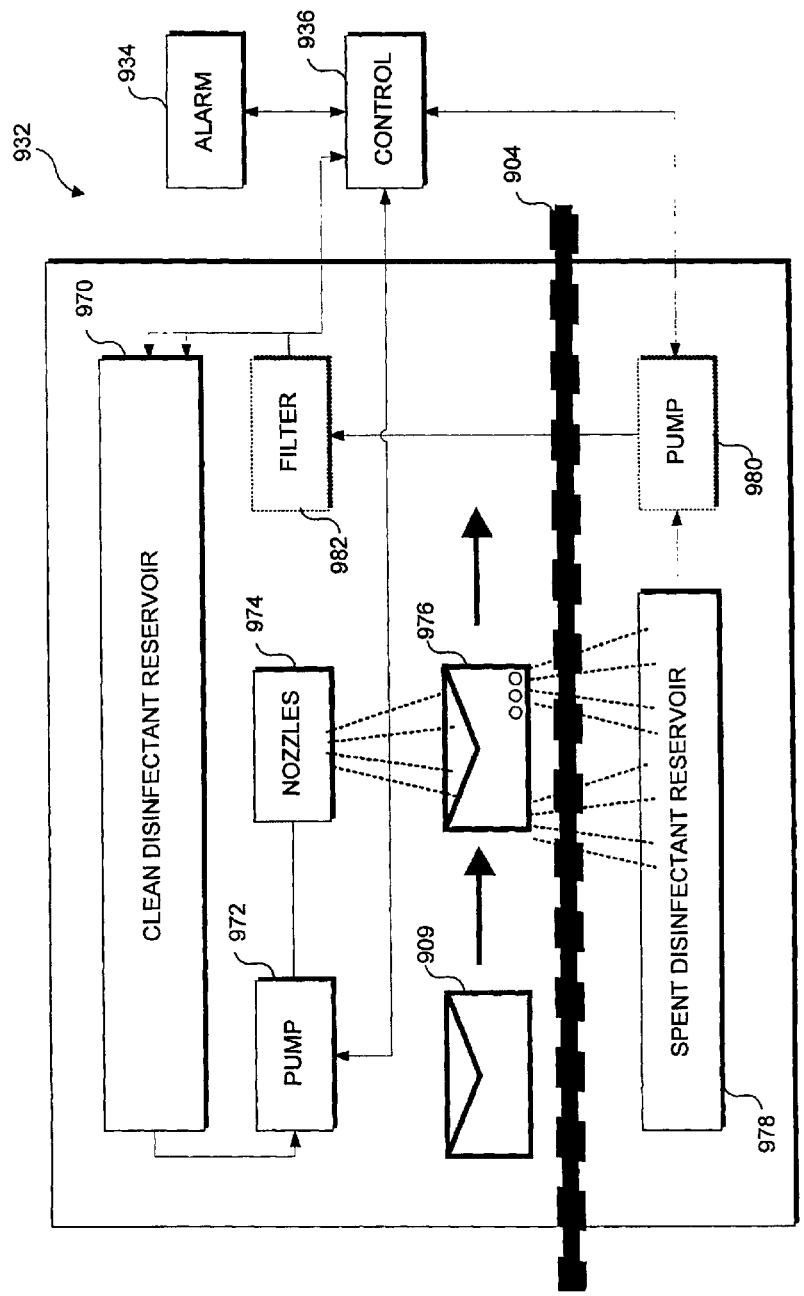
FIG. 37 is a block diagram of the components of an exemplary decontamination system for use in the present invention.

FIG. 37 illustrates the preferred components of decontamination means 932. A disinfectant reservoir 970 stores a disinfectant fluid, such as CPC, to be used to decontaminate items of mail. A pump 972, when actuated by control 936, sends a measured volume of the disinfectant fluid to nozzles 974, which directs a spray of the fluid toward a contaminated parcel 976 (and optionally to portions of the mail sampling system that are to be decontaminated). Note that the mail is positioned on feeder 904, and as discussed earlier the speed of feeder 904 is known, so that control 936 is able to track the location of each parcel within the containment chamber. Control 936 will be able to accurately determine when to spray the disinfectant fluid to ensure decontamination of a specific parcel. It is contemplated that feeder 904 will be deactivated when the contaminated parcel is adjacent to nozzles 974, so that the contaminated parcel remains in the spray of disinfectant fluid for a time sufficiently long to complete the decontamination.

The disinfectant fluid is collected in a spent disinfectant fluid reservoir 978. If desired, an optional pump 980 and filter 982 can be provided, so that used disinfectant fluid can be filtered and returned to disinfectant fluid reservoir 970. Whether such reuse of the disinfectant fluid is appropriate is a function of the specific disinfectant fluid selected. Some fluids may be more suitable for reuse than others.

In one embodiment, control 936 is coupled to a fluid level sensor (not separately shown) within disinfectant fluid reservoir 970, so that alarm 934 can be activated any time the level of disinfectant fluid within disinfectant fluid reservoir 970 drops to an unacceptably low level.

While the CPC disinfectant discussed above represents a preferred disinfectant fluid, it should be noted that other disinfectants could be beneficially employed. For example, a sterilizing gas, such as ethylene oxide (widely used in the medical industry) could also be employed. Other potential disinfectants include radiation and chlorine based disinfectants. If it is possible that high value items of mail could be damaged by a particular disinfectant, then a less damaging disinfectant could be selected. Finally, it should be noted that disinfectants are not likely to be effective against non-biological agents. If a parcel is contaminated with a chemical agent, such as cyanide, then the only effect of a disinfectant fluid will be to rinse surface contamination from the parcel. Particularly with respect to items of mail where cyanide is a suspected contaminant, care must be taken with respect to the pH level of any liquid disinfectant fluid used. Low pH liquids (i.e., acids) can react with cyanide salts to generate extremely toxic hydrogen cyanide gas, which cannot be removed by a HEPA filter.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for detecting hazardous particles associated with a parcel, comprising:
   (a) a housing into which a parcel to be analyzed can be placed, so that a parcel can be isolated from an environment outside the housing;
   (b) a triggering sampler in fluid communication with a volume of air within said housing, said triggering sampler capable of detecting particles associated with a parcel that are entrained within the volume of air in said housing, said triggering sampler generating a detection signal in response to the detection of such particles; and
   (c) a detecting sampler in fluid communication with said volume of air and electrically coupled to respond to the detection signal from said triggering sampler, said detecting sampler, in response to said detection signal, removing particles entrained within said volume of air, thereby obtaining a sample of particles, to enable an analysis to determine if particles associated with a parcel that are collected by the detecting sampler are hazardous.

2. The system of claim 1, wherein said system can accommodate parcels that include at least one of a postcard, an envelope, a flat, and a box.

3. The system of claim 1, wherein particles associated with a parcel comprise at least one of particles adhered to an outer surface of a parcel, particles adhered to an inner surface of a parcel, particles entrained in a volume of air contained within a parcel, and particles contained within an inner volume of a parcel.

4. The system of claim 1, wherein said triggering sampler is further adapted to respond to biological particles, distinguishing between biological and non-biological particles.

5. The system of claim 1, wherein said housing is maintained at a negative pressure when the system is operational.

6. The system of claim 1, wherein said housing comprises a high efficiency particulate air (HEPA) filter in fluid communication with said volume of air, said HEPA filter being adapted to filter air exhausted from said housing, to remove any particles from the air.

7. The system of claim 1, further comprising a parcel feed system that conveys a plurality of parcels through said housing, said parcel feed system introducing a plurality of parcels into said housing so that each parcel is separated from other parcels.

8. The system of claim 1, further comprising means for entraining particles associated with a parcel contained in said housing into said volume of air.

9. The system of claim 8, wherein said means comprises a laser adapted to form at least one opening in a parcel.

10. The system of claim 8, wherein said means comprise a mechanical perforator adapted to form at least one opening in a parcel.

11. The system of claim 8, wherein said means comprises a splitting blade adapted to slice open a parcel.

12. The system of claim 8, wherein said means comprises a device adapted to apply pressure to a parcel, thereby causing particles associated with a parcel to be dispersed into said volume of air contained within said housing.

13. The system of claim 8, wherein said means comprises a blower disposed within said housing, said blower directing a jet of fluid toward a parcel, said jet of fluid enhancing an aerosolization of particles associated with a parcel.

14. The system of claim 1, wherein said triggering sampler comprises a particle counter.

15. The system of claim 14, wherein said particle counter comprises means for distinguishing between biological particles and non-biological particles.

16. The system of claim 15, wherein the detection signal is generated only in response to a substantial increase in a number of biological particles being detected by the triggering sampler.

17. The system of claim 15, wherein said particle counter comprises:
   (a) a laser producing light in a waveband selected to produce auto-fluorescence in nicotinamide adenine dinucleotide (NAD); and
   (b) at least one photon sensor that detects auto-fluorescence light emitted from laser excited NAD, producing a particle count signal in response thereto.

18. The system of claim 17, further comprising a processor electrically coupled to said at least one photon sensor, said processor producing a detection signal in response to a biological particle count based on said particle count signal.

19. The system of claim 18, wherein said processor prevents said detection signal from being generated until a predefined number of biological particles are detected.

20. The system of claim 17, wherein said laser comprises a diode laser that emits light having a wavelength of between about 355 nanometers and about 370 nanometers.

21. The system of claim 1, wherein said triggering sampler comprises a virtual impactor in fluid communication with said volume of air, said virtual impactor separating a fluid stream into a major flow and a minor flow, the major flow including a minor portion of particles that are above a predetermined size and the minor flow including a major portion of the particles that are above the predetermined size, said virtual impactor including a minor flow outlet through which the minor flow exits the virtual impactor, said detection signal being produced in response to particles detected in the minor flow.

22. The system of claim 1, wherein said triggering sampler comprises:
   (a) a radial arm collector in fluid communication with said volume of air, said radial arm collector collecting any particles that were entrained in said volume of air and retaining said particles upon a surface of said radial arm collector;
   (b) a rinse fluid supply;
   (c) a rinse fluid line in fluid communication with said rinse fluid supply, said rinse fluid line conveying a rinse fluid onto the surface so that any particles adhering to said surface are carried away with the rinse fluid;
   (d) a collection volume disposed adjacent to said surface, such that particles rinsed from said surface are carried by the rinse fluid into the collection volume; and
   (e) a particle counter disposed adjacent to said collection volume, and said particle counter counting particles carried into said collection volume.

23. The system of claim 22, wherein said triggering sampler further comprises a virtual impactor in fluid communication with said volume of air, said virtual impactor separating a fluid stream into a major flow and a minor flow, the major flow including a minor portion of particles that are above a predetermined size and the minor flow including a major portion of the particles that are above the predetermined size, said virtual impactor including a minor flow outlet through which the minor flow exits the virtual impactor, said minor flow outlet being in fluid communication with said radial arm collector.

24. The system of claim 22, wherein said rinse fluid supply comprises a rinse fluid that includes an enzyme that degrades cellulose.

25. The system of claim 1, wherein said triggering sampler comprises a prefilter that removes particles above a predetermined size from said volume of air.

26. The system of claim 1, further comprising a prefilter that removes particles above a predetermined size from said volume of air.

27. The system of claim 1, wherein said detecting sampler comprises a prefilter that removes particles above a predetermined size from said volume of air.

28. The system of claim 1, wherein said detecting sampler comprises:
   (a) a radial arm collector in fluid communication with said volume of air, said radial arm collector collecting particles entrained in said volume of air and retaining said particles upon a surface of said radial arm collector;
   (b) a rinse fluid supply,
   (c) a rinse fluid line in fluid communication with said rinse fluid supply, said rinse fluid line conveying a rinse fluid onto the surface so that any particles adhering to said surface are carried away with the rinse fluid; and
   (d) a collection volume disposed adjacent to said surface, such that particles rinsed from said surface are carried by the rinse fluid into the collection volume for analysis to determine if the particles comprise a harmful substance.

29. The system of claim 28, wherein said rinse fluid supply comprises a rinse fluid that includes an enzyme that degrades cellulose.

30. The system of claim 28, wherein said detecting sampler further comprises a virtual impactor in fluid communication with said volume of air, said virtual impactor separating a fluid stream into a major flow and a minor flow, the major flow including a minor portion of particles that are above a predetermined size and the minor flow including a major portion of the particles that are above the predetermined size, said virtual impactor including a minor flow outlet through which the minor flow exits the virtual impactor, said minor flow outlet being in fluid communication with said radial arm collector.

31. The system of claim 1, wherein said detecting sampler comprises:
   (a) a disposable radial arm collector in fluid communication with said volume of air, said radial arm collector collecting any particles that were entrained in said volume of air and retaining such particles upon a surface of said disposable radial arm collector; and
   (b) a prime mover drivingly coupled to rotate a collector arm of said disposable radial arm collector, so that the collector arm impacts particles entrained in the fluid as the collector arm is rotated, said particles being retained on the surface of the collector arm.

32. The system of claim 31, wherein said disposable radial arm collector is magnetically coupled to said prime mover.

33. The system of claim 1, further comprising an archiving sampler in fluid communication with said volume of air, said archiving sampler obtaining an archival sample of particles entrained within said volume of air.

34. The system of claim 33, wherein said archiving sampler comprises:
   (a) a virtual impactor in fluid communication with said volume of air, said virtual impactor separating a fluid stream into a major flow and a minor flow, the major flow including a minor portion of particles that are above a predetermined size and the minor flow including a major portion of the particles that are above the predetermined size, said virtual impactor including a minor flow outlet through which the minor flow exits the virtual impactor;

(b) an archival surface disposed adjacent to said virtual impactor, such that the minor flow of fluid exiting said minor flow outlet is directed toward said archival surface; and (c) a prime mover drivingly coupled to one of said virtual impactor and said archival surface, causing a relative position of said virtual impactor and said archival surface to be selectively changed over time, so that the minor flow of fluid exiting through said minor flow outlet is directed toward a different portion of said archival surface over time.

35. The system of claim 1, further comprising a virtual impactor in fluid communication with said volume of air, a virtual impactor in fluid communication with said volume of air, said virtual impactor separating a fluid stream into a major flow and a minor flow, the major flow including a minor portion of particles that are above a predetermined size and the minor flow including a major portion of the particles that are above the predetermined size, said virtual impactor including a minor flow outlet through which the minor flow exits the virtual impactor, said minor flow outlet being in fluid communication with at least one of said triggering sampler and said detecting sampler.

36. The system of claim 35, wherein the virtual impactor comprises a separation plate for separating particles from a fluid stream produced with fluid drawn from the volume of air, said separation plate having a first surface and an opposing second surface, the first surface including plural pairs of a nozzle and a virtual impactor, the nozzle having an inlet end and an outlet end and tapering from the inlet end to the outlet end, the virtual impactor further comprising a pair of fin-shaped projections, each fin-shaped projection having a convex outer wall and an inner wall, the inner walls of the pair of fin-shaped projections facing each other and being spaced apart to define an upstream minor flow passage therebetween, the convex outer walls of the pair of fin-shaped projections cooperatively presenting a convex surface defining a virtual impact void therethrough, the virtual impact void defining an inlet end of the upstream minor flow passage, the convex surface facing the outlet end of each nozzle such that the nozzle and the upstream minor flow passage are generally aligned with each other.

37. The system of claim 35, wherein the virtual impactor comprises a separation plate for separating particles from a fluid stream produced with fluid from the volume of air, said separation plate having a first surface and an opposing second surface, the first surface including plural pairs of a nozzle and a virtual impactor, the nozzle having an inlet end and an outlet end and tapering from the inlet end to the outlet end, the virtual impactor is generally haystack-shaped having a convex surface facing the outlet end of each nozzle, the convex surface defining a virtual impact void therethrough, the virtual impact void defining a terminal end of a minor flow passage that communicates between the first and second surfaces.

38. The system of claim 35, wherein the virtual impactor comprises a separation plate employed for separating a fluid stream produced with fluid from the volume of air into a major flow and a minor flow, the major flow including a minor portion of particles that are above a predetermined size and the minor flow including a major portion of the particles that are above the predetermined size, said separation plate comprising:

(a) a block in which is defined a laterally extending passage having an inlet disposed on one edge of the block and an outlet disposed on an opposite edge of the block, said passage having a length extending between said inlet and said outlet, a lateral dimension extending along opposed surfaces of the passage in a direction that is orthogonal to the length and to a transverse dimension extending between the opposed surfaces, said lateral dimension being substantially greater than the transverse dimension of the passage, the opposed surfaces of said passage between which the transverse dimension of the passage is defined generally converging toward each other within the block so that said outlet has a substantially smaller cross-sectional area than said inlet;

(b) a transverse, laterally extending slot defined within said block, in fluid communication with a portion of the passage that has the substantially smaller cross-sectional area; and (c) a major flow outlet port defined in the block, in fluid communication with the transverse, laterally extending slot, the major flow entering the slot and exiting the block through the major flow outlet port, while the minor flow exits the block through the outlet of the passage, said major flow carrying the minor portion of the particles and said minor flow carrying the major portion of the particles that are above the predetermined size.

39. The system of claim 35, wherein the virtual impactor comprises:

(a) a block having a front and a rear;

(b) a laterally extending passage defined within the block and extending between an inlet at the front and an outlet at the rear of the block, said passage converging to a receiving nozzle between the inlet and the outlet, the inlet having a substantially greater height than the outlet, but the height of the inlet to the passage being substantially less than a width of the passage;

(c) an elongate slot extending transverse to the passage and disposed distally of the receiving nozzle; and (d) a major flow orifice formed within the block and intersecting the slot, said major flow orifice providing a fluid path for the major flow to exit the block after changing direction, the minor flow continuing on and out of the outlet of the passage, so that the major portion of the particles above the predetermined size are carried with the minor flow through the outlet of the passage, while the minor portion of the particles above the predetermined size are carried with the major flow through the major flow orifice.

40. The system of claim 1, further comprising a radial arm collector in fluid communication with said volume of air, said radial arm collector capturing particles entrained in a volume of fluid upon a surface of the radial arm collector, to enable at least one of the triggering sampler and the detecting sampler to obtain a sample of particles entrained in said volume of air.

41. The system of claim 40, wherein the radial arm collector comprises:

(a) a prime mover having a drive shaft that is drivingly rotated;

(b) an impeller that is mechanically coupled to the drive shaft and rotated thereby; and (c) a housing for the impeller, said housing defining a fluid passage for conveying the fluid in which the particles are entrained to the impeller, said impeller including vanes that draw the fluid into the housing so that the particles entrained in the fluid impact upon the impeller, being thereby separated from the fluid when impacted by the vanes of the impeller.

42. The system of claim 40, wherein the radial arm collector comprises:
  (a) a housing defining a port through which passes the fluid in which the particles are entrained;
  (b) an electrically energizable motor that rotates a drive shaft; and
  (c) a combined impact collector and fan mechanically coupled to the drive shah and rotated thereby, said combined impact collector and fan being disposed within a cavity defined by the housing, rotation of the combined impact collector and fan drawing the fluid into the cavity of the housing through the port, the particles in the fluid impacting the combined impact collector and fan and being retained thereon and being thus separated from the fluid.

43. The system of claim 1, further comprising an alarm electrically coupled to said triggering sampler, said alarm being activated in response to receiving said detection signal from said triggering sampler.

44. The system of claim 1, wherein the detecting sampler includes an identification unit to analyze a sample of particles obtained from said volume of air by said detecting sampler to determine if a target substance is present in said sample of particles.

45. The system of claim 44, wherein said identification unit comprises a polymerase chain reaction analyzer.

46. The system of claim 44, wherein said target substance comprises one of a biological agent and a chemical agent.

47. The system of claim 44, wherein said identification unit produces a target detection signal in response to detection of the target substance, further comprising an alarm electrically coupled to the identification unit, said alarm being activated in response to said target detection signal.

48. The system of claim 44, further comprising a control unit electrically coupled to said triggering sampler and said detecting sampler, said control unit producing a target detection signal in response to the detection of the target substance by said identification unit.

49. The system of claim 47, further comprising a decontamination system in fluid communication with said volume of air, said decontamination system being electrically coupled to said identification unit and operative to introduce a decontamination agent into said volume of air in response to receiving said target detection signal from said identification unit.

50. The system of claim 49, wherein said decontamination agent comprises a disinfectant solution selected to destroy a biological contaminant that has been carried into the housing by a parcel.

51. The system of claim 1, further comprising a decontamination system in fluid communication with said volume of air and electrically coupled to said triggering sampler, said decontamination system being operative to introduce a decontamination agent into said volume of air in response to receiving said detection signal from said triggering sampler.

52. The system of claim 51, wherein said decontamination agent comprises a disinfectant solution selected to destroy biological contaminant that has been carried into the housing by a parcel.

53. A system for detecting harmful contaminants during mail processing, wherein said contaminates are associated with an item of mail, comprising:
  (a) a housing through which mail is conveyed to detect an item of mail that is contaminated, so that a harmful substance contaminating an item of mail is isolated from the environment outside the housing;
  (b) a triggering sampler in fluid communication with a volume of air within said housing, said triggering sampler being adapted to obtain particles from an item of mail, said particles being entrained within the volume of air in said housing, said triggering sampler generating a detection signal in response to the particles;
  (c) a detecting sampler in fluid communication with said volume of air and responsive to the detection signal, said detecting sampler being adapted to obtain a sample of particles within said volume of air in response to receiving said detection signal, to enable an analysis to detect particles of a contaminant that is harmful; and
  (d) a control unit electrically coupled to the triggering sampler and to the detecting sampler to control the operation of said system, said control unit conveying said detection signal to said detecting sampler.

54. A system for detecting a harmful contaminant that is associated with a parcel, comprising:
  (a) a housing into which a parcel to be analyzed is placed, so that so any contaminant carried by the parcel is isolated from an environment outside the housing;
  (b) means for distributing particles associated with a parcel into a volume of air within said housing;
  (c) a triggering sampler in fluid communication with said volume of air within said housing and operative to detect trace amounts of particles within said volume of air, said triggering sampler generating a detection signal in response detection of such particles; and
  (d) a detecting sampler in fluid communication with said volume of air and electrically coupled to respond to the detection signal, said detecting sampler obtaining a sample of particles within said volume of air in response to said detection signal, to enable an analysis of such particles to determine if a harmful contaminant is present.

55. A method for detecting the presence of a chemical or a biological agent in association with a parcel, comprising the steps of:
  (a) obtaining a first sample of particles associated with said parcel using a first sampling system;
  (b) determining at least one of a quantitative and a qualitative measure of the first sample of particles;
  (c) in response to said at least one of the qualitative and the quantitative measure, automatically obtaining a second sample of particles associated with said parcel using a second sampling system; and
  (d) analyzing the second sample of particles, to determine if at least one of a chemical agent and a biological agent is associated with said parcel.

56. The method of claim 55, further comprising the step of isolating said parcel from an ambient environment before obtaining said first sample of particles.

57. The method of claim 55, wherein the step of isolating said parcel from the ambient environment comprises the step of introducing the parcel into a containment chamber kept under a negative pressure relative to an atmospheric pressure of the ambient environment.

58. The method of claim 57, wherein the step of introducing the parcel into a containment chamber kept under negative pressure comprises the step of utilizing conventional mail processing equipment to convey a plurality of parcels into the containment chamber so that each parcel is individually accessible in the containment chamber.

59. The method of claim 57, wherein the step of introducing the parcel comprises the step of conveying a plurality of parcels on a conveyor into the containment chamber.

60. The method of claim 55, wherein the step of obtaining the first sample of particles comprises the step of forming at least one opening in the parcel using a laser to enable particles contained within the parcel to be sampled.

61. The method of claim 55, wherein the step of obtaining the first sample of particles comprises the step of forming at least one opening in the parcel using a mechanical perforator to enable particles from within the parcel to be sampled.

62. The method of claim 55, wherein the step of obtaining the first sample of particles comprises the step of using an envelope splitter to open the parcel to enable particles from within the parcel to be sampled.

63. The method of claim 55, wherein the step of obtaining the first sample of particles comprises the step of compressing the parcel to expel particles from within the parcel, to enable such particles to be sampled.

64. The method of claim 55, wherein the step of obtaining a first sample of particles further comprises the step of using a blower to direct a jet of air toward the parcel, thereby enhancing an aerosolization of any particles associated with the parcel.

65. The method of claim 55, wherein the step of determining at least one of a quantitative and a qualitative measure of the first sample of particles associated with the parcel comprises the step of counting a number of particles present in the first sample.

66. The method of claim 65, wherein the step of determining at least one of a quantitative and a qualitative measure of the first sample of particles comprises the steps of separating the first sample into a major flow and a minor flow, such that the majority of particles are entrained in the minor flow, and counting the particles in the minor flow.

67. The method of claim 65, wherein the step of determining at least one of a quantitative and a qualitative measure of the first sample of particles comprises the steps of:
(a) using a rotating arm collector to collect particles entrained in the first sample of particles;
(b) rinsing the collected particles from the rotating arm collector with a rinse fluid; and
(c) counting the particles in the rinse fluid.

68. The method of claim 67, wherein the step of rinsing the collected particles from the rotating arm collector with a rinse fluid comprises the steps of using a rinse fluid that includes an enzyme that causes cellulose to degrade, thereby reducing a build up of paper fibers on said rotating arm collector.

69. The method of claim 65, wherein the step of counting the number of particles in the first sample comprises at least one of the steps of:
(a) determining a total number of particles in the first sample; and
(b) determining a total number of biological particles in the first sample.

70. The method of claim 69, further comprising the step of determining whether the parcel is potentially contaminated with a harmful agent by determining if the total number of particles in the first sample exceeds a predetermined threshold value.

71. The method of claim 69, further comprising the step of determining whether the parcel is potentially contaminated by determining if the total number of biological particles in the first sample exceeds a predetermined threshold value.

72. The method of claim 69, further comprising the step of determining whether the parcel is potentially contaminated by determining if any biological particles are present in the first sample.

73. The method of claim 55, further comprising the step of determining whether the parcel is potentially contaminated by determining if at least one of the following conditions exist:
(a) the total number of particles in the first sample exceeds a predetermined threshold value;
(b) the total number of biological particles in the first sample exceeds a predetermined threshold value; and
(c) any biological particles are present in the first sample.

74. The method of claim 55, wherein the step of obtaining a second sample of particles associated with the parcel comprises the step obtaining a sample from a location proximate to where the first sample was obtained.

75. The method of claim 55, wherein the step of obtaining a second sample of particles associated with the parcel comprises the steps of separating the second sample into a major flow and a minor flow, such that the majority of particles are entrained in the minor flow; and, directing the minor flow toward a particle collector.

76. The method of claim 55, wherein the step of obtaining a second sample of particles associated with the parcel comprises the step of using a rotating arm collector to collect particles entrained in the second sample.

77. The method of claim 76, wherein the step of obtaining a second sample of particles associated with the parcel further comprises the steps of:
(a) rinsing the collected particles from the rotating arm collector with a rinse fluid, and
(b) collecting the rinse fluid containing the particles rinsed from the rotating arm collector to obtain the second sample.

78. The method of claim 55, wherein the step of analyzing the second sample comprises the steps of analyzing any particulates obtained from the second sample to detect a specific one of a chemical agent and a biological agent.

79. The method of claim 55, further comprising the step of decontaminating the parcel after obtaining the second sample if it is determined that the parcel is contaminated with one of a biological and a chemical agent.

80. The method of claim 55, further comprising the step of activating an alarm if it is determined that the parcel is contaminated with one of a biological and a chemical agent.

81. The method of claim 55, further comprising the step of decontaminating the parcel after obtaining the second sample if it is determined that the parcel is contaminated with one of a biological and a chemical agent.

82. The method of claim 55, further comprising the step of decontaminating the parcel and the area proximate to the parcel after obtaining the second sample if it is determined that the parcel is contaminated with one of a biological and a chemical agent.

83. The method of claim 55, further comprising the step of temporarily stopping processing of additional parcels to detect contamination in such additional parcels if it is determined that the parcel is contaminated with one of a biological and a chemical agent.

84. The method of claim 55, further comprising the step of obtaining an archival sample if it is determined that the parcel is potentially contaminated with one of a biological and a chemical agent.

85. The method of claim 84, wherein the step of obtaining the archival sample comprises the step of directing particles associated with the parcel toward a specific location on an archival surface, to deposit a spot of particles on the archival surface, such that each spot of particles deposited on the archival surface represents an archival sampled from a different parcel.

86. The method of claim 84, wherein the step of obtaining the archival sample comprises the steps of separating a flow of fluid containing particles associated with the parcel into a major flow and a minor flow, such that the majority of particles from the flow of fluid are entrained in the minor flow, and directing the minor flow toward an archival surface, to deposit a spot of particles on the archival surface, such that each spot of particles deposited on the archival surface represents an archival sampled from a different parcel.

87. The method of claim 55, further comprising the step of obtaining an archival sample if it is determined that the parcel is contaminated with one of biological and a chemical agent.

88. A system for detecting hazardous particles associated with a parcel, comprising:

(a) a housing into which a parcel to be analyzed can be placed, so that a parcel can be isolated from an environment outside the housing;

(b) a triggering sampler in fluid communication with a volume of air within said housing, said triggering sampler being capable of detecting particles associated with a parcel that are entrained within the volume of air in said housing, said triggering sampler regularly sampling the air in said housing and generating a detection signal in response to detecting such particles; and (c) a detecting sampler in fluid communication with said volume of air and electrically coupled to the triggering sampler to respond to the detection signal from said triggering sampler, said detecting sampler, in response to said detection signal, removing particles entrained within said volume of air, thereby obtaining a sample of particles, to enable an analysis to determine if particles associated with a parcel that are collected by the detecting sampler are hazardous.

* * * * *